(12) United States Patent
Harvey et al.

(10) Patent No.: US 10,405,892 B2
(45) Date of Patent: *Sep. 10, 2019

(54) UNI-PLANER BONE FIXATION ASSEMBLY

(71) Applicant: DePuy Synthes Products, Inc., Raynham, MA (US)

(72) Inventors: Dustin M. Harvey, Pottstown, PA (US); Brian Dec, Exton, PA (US); Tom Keyer, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 37 days.

This patent is subject to a terminal disclaimer.

(21) Appl. No.: 15/090,752

(22) Filed: Apr. 5, 2016

(65) Prior Publication Data
US 2016/0220284 A1 Aug. 4, 2016

Related U.S. Application Data

(63) Continuation of application No. 14/143,489, filed on Dec. 30, 2013, now Pat. No. 9,326,796, which is a continuation of application No. 12/611,286, filed on Nov. 3, 2009, now Pat. No. 8,628,558.

(60) Provisional application No. 61/110,704, filed on Nov. 3, 2008.

(51) Int. Cl.
*A61B 17/70* (2006.01)
*A61B 17/86* (2006.01)

(52) U.S. Cl.
CPC ...... *A61B 17/7038* (2013.01); *A61B 17/7032* (2013.01); *A61B 17/7037* (2013.01); *A61B 17/7049* (2013.01); *A61B 17/8685* (2013.01)

(58) Field of Classification Search
CPC ............ A61B 17/7032; A61B 17/7037; A61B 17/7038
See application file for complete search history.

(56) References Cited

U.S. PATENT DOCUMENTS

| 405,546 A | 6/1889 | Frist |
| 513,630 A | 1/1894 | Beard |
| 527,678 A | 10/1894 | Francis |
| 802,896 A | 10/1905 | Webb |

(Continued)

FOREIGN PATENT DOCUMENTS

| CA | 2289629 | 11/1998 |
| CN | 102368967 A | 3/2012 |

(Continued)

OTHER PUBLICATIONS

International Patent Application No. PCT/US2010/031178: International Search Report dated Jun. 22, 2010, 8 pages.

(Continued)

*Primary Examiner* — Ellen C Hammond
(74) *Attorney, Agent, or Firm* — BakerHostetler

(57) ABSTRACT

A bone fixation assembly includes a plurality of bone fixation elements that each include a bone anchor configured to be implanted into underlying bone, such as a vertebra. Each bone anchor is received in an anchor seat, and the anchor seats are joined by a fixation rod so as to operatively couple and fix the position and orientation of the vertebrae relative to each other. The bone anchor is free to rotate relative to the anchor seat, and is also free to pivot in a desired direction relative to the anchor seat.

17 Claims, 30 Drawing Sheets

(56) References Cited

U.S. PATENT DOCUMENTS

| | | |
|---|---|---|
| 2,005,348 A | 6/1935 | Michell |
| 2,338,659 A | 1/1944 | Morehouse |
| 2,396,925 A | 3/1946 | Morehouse |
| 3,173,987 A | 3/1965 | Potruch |
| 3,463,427 A | 8/1969 | Fisher |
| 4,447,934 A | 5/1984 | Anscher |
| 4,601,491 A | 7/1986 | Bell, Jr. et al. |
| 4,719,905 A | 1/1988 | Steffee |
| 4,805,602 A | 2/1989 | Puno et al. |
| 4,846,614 A | 7/1989 | Steinbock |
| 4,863,383 A | 9/1989 | Grafelmann |
| 4,936,851 A | 6/1990 | Fox |
| 4,944,475 A | 7/1990 | Ono et al. |
| 4,946,458 A | 8/1990 | Harms et al. |
| 5,005,562 A | 4/1991 | Cotrel |
| 5,116,337 A | 5/1992 | Johnson |
| 5,129,388 A | 7/1992 | Lapresle |
| 5,207,678 A | 5/1993 | Harms et al. |
| 5,242,446 A | 9/1993 | Steffee et al. |
| 5,270,678 A | 12/1993 | Gambut et al. |
| 5,282,825 A | 2/1994 | Muck et al. |
| 5,304,178 A | 4/1994 | Stahurski |
| 5,306,275 A | 4/1994 | Bryan |
| 5,306,285 A | 4/1994 | Bryan |
| 5,312,410 A | 5/1994 | Miller et al. |
| 5,360,431 A | 11/1994 | Puno et al. |
| 5,383,882 A | 1/1995 | Buess et al. |
| 5,395,374 A | 3/1995 | Miller et al. |
| 5,413,576 A | 5/1995 | Rivard |
| 5,413,602 A | 5/1995 | Metz-Stavenhagen |
| 5,417,684 A | 5/1995 | Jackson et al. |
| 5,443,467 A | 8/1995 | Biedermann |
| 5,449,361 A | 9/1995 | Preissman |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,476,464 A | 12/1995 | Metz-Stavenhagen et al. |
| 5,486,174 A | 1/1996 | Fournet-Fayard et al. |
| 5,496,321 A | 3/1996 | Puno et al. |
| 5,498,262 A | 3/1996 | Bryan |
| 5,501,684 A | 3/1996 | Schlapfer et al. |
| 5,520,689 A | 5/1996 | Schlaepfer et al. |
| 5,520,690 A | 5/1996 | Errico et al. |
| 5,527,183 A | 6/1996 | O'Brien |
| 5,531,746 A | 7/1996 | Errico et al. |
| 5,534,001 A | 7/1996 | Schlapfer et al. |
| 5,536,268 A | 7/1996 | Griss |
| 5,536,270 A | 7/1996 | Songer et al. |
| 5,540,698 A | 7/1996 | Preissman et al. |
| 5,549,608 A | 8/1996 | Errico et al. |
| 5,549,677 A | 8/1996 | Durr |
| 5,554,157 A | 9/1996 | Errico et al. |
| 5,562,661 A | 10/1996 | Yoshimi et al. |
| 5,575,792 A | 11/1996 | Errico et al. |
| 5,578,033 A | 11/1996 | Errico et al. |
| 5,584,832 A | 12/1996 | Schlaepfer |
| 5,584,834 A | 12/1996 | Errico et al. |
| 5,586,984 A | 12/1996 | Errico et al. |
| 5,601,261 A | 2/1997 | Koike |
| 5,601,429 A | 2/1997 | Blacklock |
| 5,605,457 A | 2/1997 | Bailey et al. |
| 5,605,458 A | 2/1997 | Bailey et al. |
| 5,607,304 A | 3/1997 | Bailey et al. |
| 5,607,426 A | 3/1997 | Ralph et al. |
| 5,609,593 A | 3/1997 | Errico et al. |
| 5,609,594 A | 3/1997 | Errico et al. |
| 5,624,442 A | 4/1997 | Mellinger et al. |
| 5,643,262 A | 7/1997 | Metz-Stavenhagen et al. |
| 5,643,265 A | 7/1997 | Errico et al. |
| 5,645,544 A | 7/1997 | Tai et al. |
| 5,647,873 A | 7/1997 | Errico et al. |
| 5,662,651 A | 9/1997 | Tornier et al. |
| 5,667,508 A | 9/1997 | Errico et al. |
| 5,669,911 A | 9/1997 | Errico et al. |
| 5,672,175 A | 9/1997 | Martin |
| 5,683,390 A | 11/1997 | Metz-Stavenhagen et al. |
| 5,683,392 A | 11/1997 | Richelsoph et al. |
| 5,683,404 A | 11/1997 | Johnson |
| 5,688,273 A | 11/1997 | Errico et al. |
| 5,690,630 A | 11/1997 | Errico et al. |
| 5,694,760 A | 12/1997 | Baxter |
| 5,704,939 A | 1/1998 | Justin |
| 5,725,582 A | 3/1998 | Bevan et al. |
| 5,725,588 A | 3/1998 | Errico et al. |
| 5,728,098 A | 3/1998 | Sherman et al. |
| 5,733,285 A | 3/1998 | Errico et al. |
| 5,738,685 A | 4/1998 | Halm et al. |
| 5,772,663 A | 6/1998 | Whiteside et al. |
| 5,782,831 A | 7/1998 | Sherman et al. |
| 5,782,833 A | 7/1998 | Haider |
| 5,797,911 A | 8/1998 | Sherman et al. |
| 5,810,818 A | 9/1998 | Errico et al. |
| 5,817,094 A | 10/1998 | Errico et al. |
| 5,860,987 A | 1/1999 | Ratcliff et al. |
| 5,863,293 A | 1/1999 | Richelsoph |
| 5,868,748 A | 2/1999 | Burke |
| 5,876,402 A | 3/1999 | Errico et al. |
| 5,879,350 A | 3/1999 | Sherman et al. |
| 5,882,350 A | 3/1999 | Ralph et al. |
| 5,885,286 A | 3/1999 | Sherman et al. |
| 5,888,204 A | 3/1999 | Ralph et al. |
| 5,891,145 A | 4/1999 | Morrison et al. |
| 5,899,940 A | 5/1999 | Carchidi |
| 5,902,305 A | 5/1999 | Beger |
| 5,938,663 A | 8/1999 | Petreto |
| 5,951,287 A | 9/1999 | Hawkinson |
| 5,961,329 A | 10/1999 | Stucki-McCormick |
| 5,964,760 A | 10/1999 | Richelsoph |
| 6,001,098 A | 12/1999 | Metz-Stavenhagen et al. |
| 6,010,503 A | 1/2000 | Richelsoph et al. |
| 6,015,409 A | 1/2000 | Jackson |
| 6,017,177 A | 1/2000 | Lanham |
| 6,019,760 A | 2/2000 | Metz-Stavenhagen et al. |
| 6,022,350 A | 2/2000 | Ganem |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlaepfer et al. |
| 6,077,263 A | 6/2000 | Ameil et al. |
| 6,083,224 A | 7/2000 | Gertzbein et al. |
| 6,090,110 A | 7/2000 | Metz-Stavenhagen |
| 6,126,662 A | 10/2000 | Carmichael |
| 6,132,432 A | 10/2000 | Richelsoph |
| 6,183,472 B1 | 2/2001 | Lutz |
| 6,214,006 B1 | 4/2001 | Metz-Stavenhagen |
| 6,217,331 B1 | 4/2001 | Rogers |
| 6,224,598 B1 | 5/2001 | Jackson |
| 6,248,105 B1 | 6/2001 | Schlapfer et al. |
| 6,261,287 B1 | 7/2001 | Metz-Stavenhagen |
| 6,273,914 B1 | 8/2001 | Papas |
| 6,280,442 B1 | 8/2001 | Barker et al. |
| 6,296,642 B1 | 10/2001 | Morrison et al. |
| 6,325,802 B1 | 12/2001 | Frigg |
| 6,355,040 B1 | 3/2002 | Richelsoph et al. |
| 6,361,535 B2 | 3/2002 | Jackson |
| RE37,665 E | 4/2002 | Ralph et al. |
| 6,368,321 B1 | 4/2002 | Jackson |
| 6,402,752 B2 | 6/2002 | Schaffler-Wachter et al. |
| 6,440,132 B1 | 8/2002 | Jackson |
| 6,443,953 B1 | 9/2002 | Perra et al. |
| 6,451,021 B1 | 9/2002 | Ralph et al. |
| 6,454,768 B1 | 9/2002 | Jackson |
| 6,454,772 B1 | 9/2002 | Jackson |
| 6,471,705 B1 | 10/2002 | Biedermann et al. |
| 6,482,207 B1 | 11/2002 | Errico |
| 6,485,491 B1 | 11/2002 | Farris et al. |
| 6,491,696 B1 | 12/2002 | Kunkel |
| 6,508,820 B2 | 1/2003 | Bales |
| 6,514,255 B1 | 2/2003 | Ferree |
| 6,520,963 B1 | 2/2003 | McKinley |
| 6,533,226 B2 | 3/2003 | Geiger |
| 6,537,070 B1 | 3/2003 | Stucki-McCormick |
| 6,537,276 B2 | 3/2003 | Metz-Stavenhagen |
| 6,554,831 B1 | 4/2003 | Rivard et al. |

(56) References Cited

U.S. PATENT DOCUMENTS

| | | |
|---|---|---|
| 6,558,387 B2 | 5/2003 | Errico et al. |
| 6,565,565 B1 | 5/2003 | Yuan et al. |
| 6,585,740 B2 | 7/2003 | Schlapfer et al. |
| 6,616,667 B1 | 9/2003 | Steiger et al. |
| 6,626,908 B2 | 9/2003 | Cooper et al. |
| 6,641,586 B2 | 11/2003 | Varieur |
| 6,641,588 B2 | 11/2003 | Citron et al. |
| 6,660,004 B2 | 12/2003 | Barker et al. |
| 6,689,140 B2 | 2/2004 | Cohen |
| 6,695,852 B2 | 2/2004 | Gleason |
| 6,716,214 B1 | 4/2004 | Jackson |
| 6,726,687 B2 | 4/2004 | Jackson |
| 6,736,820 B2 | 5/2004 | Biedermann et al. |
| 6,738,527 B2 | 5/2004 | Kuwata et al. |
| 6,740,086 B2 | 5/2004 | Richelsoph |
| 6,749,613 B1 | 6/2004 | Conchy et al. |
| 6,755,829 B1 | 6/2004 | Bono et al. |
| 6,770,075 B2 | 8/2004 | Howland |
| 6,780,186 B2 | 8/2004 | Errico et al. |
| 6,783,527 B2 | 8/2004 | Drewry et al. |
| 6,802,844 B2 | 10/2004 | Ferree |
| 6,827,719 B2 | 12/2004 | Ralph et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,869,433 B2 | 3/2005 | Glascott |
| 6,887,275 B2 | 5/2005 | Carchidi |
| 6,933,440 B2 | 8/2005 | Ichikawa et al. |
| 6,964,666 B2 | 11/2005 | Jackson |
| 6,974,460 B2 | 12/2005 | Carbone et al. |
| 6,981,973 B2 | 1/2006 | McKinley |
| 7,008,227 B2 | 3/2006 | Carmichael |
| 7,018,378 B2 | 3/2006 | Biedermann et al. |
| RE39,089 E | 5/2006 | Ralph et al. |
| 7,073,415 B2 | 7/2006 | Casutt et al. |
| 7,081,117 B2 | 7/2006 | Bono et al. |
| 7,087,057 B2 | 8/2006 | Konieczynski et al. |
| D527,678 S | 9/2006 | Warner |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,131,467 B2 | 11/2006 | Gao et al. |
| 7,144,396 B2 | 12/2006 | Shluzas |
| 7,163,539 B2 | 1/2007 | Abdelgany et al. |
| 7,175,622 B2 | 2/2007 | Farris |
| 7,186,255 B2 | 3/2007 | Baynham et al. |
| 7,211,086 B2 | 5/2007 | Biedermann et al. |
| 7,223,268 B2 | 5/2007 | Biedermann |
| 7,250,052 B2 | 7/2007 | Landry et al. |
| 7,270,665 B2 | 9/2007 | Morrison et al. |
| 7,316,684 B1 | 1/2008 | Baccelli et al. |
| 7,322,548 B2 | 1/2008 | Mielke et al. |
| 7,330,490 B2 | 2/2008 | Furukawa et al. |
| 7,338,490 B2 | 3/2008 | Ogilvie et al. |
| 7,445,627 B2 | 11/2008 | Hawkes et al. |
| 7,452,360 B2 | 11/2008 | Trudeau et al. |
| 7,476,239 B2 | 1/2009 | Jackson |
| 7,547,319 B2 | 6/2009 | Segal et al. |
| 7,591,839 B2 | 9/2009 | Biedermann |
| 7,592,546 B2 | 9/2009 | Johansson |
| 7,645,282 B2 | 1/2010 | Huxel et al. |
| 7,648,520 B2 | 1/2010 | Markworth |
| 7,691,131 B2 | 4/2010 | Graf |
| 7,708,762 B2 | 5/2010 | McCarthy et al. |
| 7,766,944 B2 | 8/2010 | Metz-Stavenhagen |
| 7,780,706 B2 * | 8/2010 | Marino .............. A61B 17/7037 606/264 |
| 7,785,352 B2 | 8/2010 | Snyder et al. |
| 7,785,354 B2 | 8/2010 | Biedermann |
| 7,799,054 B2 | 9/2010 | Kwak et al. |
| 7,803,174 B2 | 9/2010 | Francis et al. |
| 7,806,895 B2 | 10/2010 | Weier et al. |
| 7,819,902 B2 | 10/2010 | Abdelgany et al. |
| 7,951,172 B2 | 5/2011 | Chao et al. |
| 7,967,849 B2 | 6/2011 | Carson et al. |
| 8,001,946 B2 | 8/2011 | Leitl |
| 8,002,806 B2 * | 8/2011 | Justis ................ A61B 17/7038 606/246 |
| 8,029,513 B2 | 10/2011 | Konno et al. |
| 8,029,546 B2 | 10/2011 | Capote et al. |
| 8,038,701 B2 | 10/2011 | Rock et al. |
| 8,096,998 B2 | 1/2012 | Cresina |
| 8,100,946 B2 | 1/2012 | Strausbaugh et al. |
| 8,137,356 B2 | 3/2012 | Hestad et al. |
| 8,172,772 B2 | 5/2012 | Zwolinski et al. |
| 8,197,517 B1 | 6/2012 | Lab et al. |
| 8,216,245 B2 | 7/2012 | Gil et al. |
| 8,221,464 B2 | 7/2012 | Belliard et al. |
| 8,231,626 B2 | 7/2012 | Hulliger et al. |
| 8,241,333 B2 | 8/2012 | Jackson |
| 8,246,659 B2 | 8/2012 | Vonwiller et al. |
| 8,257,367 B2 | 9/2012 | Bryant et al. |
| 8,308,782 B2 | 11/2012 | Jackson |
| 8,317,836 B2 * | 11/2012 | Zucherman ........ A61B 17/7035 606/267 |
| 8,323,318 B2 | 12/2012 | Baccelli et al. |
| 8,444,681 B2 | 5/2013 | Surber |
| 8,469,960 B2 | 6/2013 | Hutton et al. |
| 8,469,966 B2 | 6/2013 | Allen et al. |
| 8,556,938 B2 | 10/2013 | Surber |
| 8,632,572 B2 | 1/2014 | Darst Rice et al. |
| 8,663,298 B2 | 3/2014 | Keyer et al. |
| 8,814,910 B2 | 8/2014 | Baccelli et al. |
| 8,840,652 B2 | 9/2014 | Jackson |
| 8,870,869 B2 | 10/2014 | Meunier et al. |
| 8,870,870 B2 | 10/2014 | Baccelli et al. |
| 8,882,803 B2 | 11/2014 | Iott et al. |
| 8,911,478 B2 | 12/2014 | Surber |
| 8,911,479 B2 | 12/2014 | Surber |
| 8,926,672 B2 | 1/2015 | Surber |
| 8,979,904 B2 | 3/2015 | Surber |
| 8,998,959 B2 | 4/2015 | Surber |
| 8,998,961 B1 | 4/2015 | Ziemek et al. |
| 9,039,708 B2 | 5/2015 | Larroque-Lahitette |
| 9,168,069 B2 | 10/2015 | Surber |
| 9,216,041 B2 | 12/2015 | Surber |
| 9,320,546 B2 | 4/2016 | Keyer et al. |
| 9,393,047 B2 | 7/2016 | Surber |
| 9,439,681 B2 | 9/2016 | Keyer et al. |
| 9,451,993 B2 | 9/2016 | Jackson |
| 9,480,517 B2 | 11/2016 | Jackson |
| 9,504,496 B2 | 11/2016 | Surber |
| 9,522,021 B2 | 12/2016 | Jackson |
| 9,636,146 B2 | 5/2017 | Jackson |
| 9,717,533 B2 | 8/2017 | Jackson |
| 9,717,534 B2 | 8/2017 | Jackson |
| 2001/0047173 A1 | 11/2001 | Schlapfer et al. |
| 2002/0045899 A1 | 4/2002 | Errico et al. |
| 2002/0068940 A1 | 6/2002 | Gaines |
| 2002/0069537 A1 | 6/2002 | Wenzler |
| 2002/0103487 A1 | 8/2002 | Errico et al. |
| 2002/0117321 A1 | 8/2002 | Beebe et al. |
| 2002/0120272 A1 | 8/2002 | Yuan et al. |
| 2002/0138077 A1 | 9/2002 | Ferree |
| 2002/0143341 A1 | 10/2002 | Biedermann et al. |
| 2002/0151900 A1 | 10/2002 | Glascott |
| 2003/0100896 A1 | 5/2003 | Biedermann et al. |
| 2003/0100904 A1 | 5/2003 | Biedermann |
| 2003/0125741 A1 | 7/2003 | Biedermann et al. |
| 2003/0125742 A1 | 7/2003 | Yuan et al. |
| 2003/0149431 A1 | 8/2003 | Varieur |
| 2003/0153912 A1 | 8/2003 | Graf |
| 2004/0006342 A1 | 1/2004 | Altarac et al. |
| 2004/0024464 A1 | 2/2004 | Errico et al. |
| 2004/0039384 A1 | 2/2004 | Boehm et al. |
| 2004/0111088 A1 | 6/2004 | Picetti et al. |
| 2004/0138660 A1 | 7/2004 | Serhan |
| 2004/0143265 A1 | 7/2004 | Landry et al. |
| 2004/0153077 A1 | 8/2004 | Biedermann et al. |
| 2004/0157186 A1 | 8/2004 | Abels et al. |
| 2004/0162558 A1 | 8/2004 | Hegde et al. |
| 2004/0172022 A1 | 9/2004 | Landry et al. |
| 2004/0181224 A1 | 9/2004 | Biedermann et al. |
| 2004/0186473 A1 | 9/2004 | Cournoyer et al. |

(56) References Cited

U.S. PATENT DOCUMENTS

| | | |
|---|---|---|
| 2004/0186474 A1 | 9/2004 | Matthis et al. |
| 2004/0193160 A1 | 9/2004 | Richelsoph |
| 2004/0199169 A1 | 10/2004 | Koons et al. |
| 2004/0225292 A1 | 11/2004 | Sasso et al. |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0033298 A1 | 2/2005 | Hawkes et al. |
| 2005/0049588 A1 | 3/2005 | Jackson |
| 2005/0049589 A1 | 3/2005 | Jackson |
| 2005/0055026 A1 | 3/2005 | Biederman et al. |
| 2005/0080415 A1 | 4/2005 | Keyer et al. |
| 2005/0080420 A1 | 4/2005 | Farris et al. |
| 2005/0143737 A1 | 6/2005 | Pafford et al. |
| 2005/0154389 A1 | 7/2005 | Selover et al. |
| 2005/0154391 A1 | 7/2005 | Doherty |
| 2005/0171537 A1 | 8/2005 | Mazel et al. |
| 2005/0171542 A1 | 8/2005 | Biedermann et al. |
| 2005/0177154 A1 | 8/2005 | Moumene et al. |
| 2005/0177166 A1 | 8/2005 | Timm et al. |
| 2005/0177179 A1 | 8/2005 | Baynham et al. |
| 2005/0187548 A1 | 8/2005 | Butler et al. |
| 2005/0192571 A1 | 9/2005 | Abdelgany |
| 2005/0203515 A1 | 9/2005 | Doherty et al. |
| 2005/0203516 A1 | 9/2005 | Biedermann et al. |
| 2005/0209592 A1 | 9/2005 | Schlapfer et al. |
| 2005/0216001 A1 | 9/2005 | David |
| 2005/0216003 A1 | 9/2005 | Biedermann et al. |
| 2005/0228378 A1 | 10/2005 | Kalfas et al. |
| 2005/0228385 A1 | 10/2005 | Iott et al. |
| 2005/0234421 A1 | 10/2005 | Markworth |
| 2005/0234451 A1 | 10/2005 | Markworth |
| 2005/0261687 A1 | 11/2005 | Garamszegi et al. |
| 2005/0277928 A1 | 12/2005 | Boschert |
| 2005/0283157 A1 | 12/2005 | Coates et al. |
| 2005/0288671 A1 | 12/2005 | Yuan et al. |
| 2006/0004357 A1 | 1/2006 | Lee et al. |
| 2006/0025767 A1 | 2/2006 | Khalili |
| 2006/0025770 A1 | 2/2006 | Schlapfer et al. |
| 2006/0036252 A1 | 2/2006 | Baynham et al. |
| 2006/0052818 A1 | 3/2006 | Drake et al. |
| 2006/0064091 A1 | 3/2006 | Ludwig et al. |
| 2006/0079892 A1 | 4/2006 | Roychowdhury et al. |
| 2006/0084993 A1 | 4/2006 | Landry et al. |
| 2006/0084995 A1 | 4/2006 | Biedermann et al. |
| 2006/0084996 A1 | 4/2006 | Metz-Stavenhagen |
| 2006/0089634 A1 | 4/2006 | Anderson et al. |
| 2006/0089643 A1 | 4/2006 | Mujwid |
| 2006/0106383 A1 | 5/2006 | Biedermann et al. |
| 2006/0111779 A1 | 5/2006 | Petersen et al. |
| 2006/0129149 A1 | 6/2006 | Iott et al. |
| 2006/0142761 A1 | 6/2006 | Landry et al. |
| 2006/0149232 A1 | 7/2006 | Sasing |
| 2006/0149233 A1 | 7/2006 | Richelsoph |
| 2006/0149241 A1 | 7/2006 | Richelsoph et al. |
| 2006/0149265 A1 | 7/2006 | James |
| 2006/0155277 A1 | 7/2006 | Metz-Stavenhagen |
| 2006/0173456 A1 | 8/2006 | Hawkes et al. |
| 2006/0200131 A1* | 9/2006 | Chao ............... A61B 17/7037 606/278 |
| 2006/0212034 A1 | 9/2006 | Triplett et al. |
| 2006/0217717 A1 | 9/2006 | Whipple |
| 2006/0229611 A1 | 10/2006 | Avery et al. |
| 2006/0235385 A1 | 10/2006 | Whipple |
| 2006/0235393 A1 | 10/2006 | Bono et al. |
| 2006/0241594 A1 | 10/2006 | McCarthy et al. |
| 2006/0241599 A1 | 10/2006 | Konieczynski et al. |
| 2006/0241624 A1 | 10/2006 | Kizuka et al. |
| 2006/0247636 A1 | 11/2006 | Yuan et al. |
| 2006/0247668 A1 | 11/2006 | Park |
| 2006/0271047 A1 | 11/2006 | Jackson |
| 2006/0293659 A1 | 12/2006 | Alvarez |
| 2006/0293664 A1 | 12/2006 | Schumacher |
| 2007/0016200 A1 | 1/2007 | Jackson |
| 2007/0043365 A1 | 2/2007 | Ritland |
| 2007/0049932 A1 | 3/2007 | Richelsoph et al. |
| 2007/0055240 A1 | 3/2007 | Matthis et al. |
| 2007/0088357 A1 | 4/2007 | Johnson |
| 2007/0090238 A1 | 4/2007 | Justis |
| 2007/0118118 A1 | 5/2007 | Kwak et al. |
| 2007/0118121 A1 | 5/2007 | Purcell et al. |
| 2007/0118123 A1 | 5/2007 | Strausbaugh et al. |
| 2007/0123860 A1 | 5/2007 | Francis et al. |
| 2007/0123870 A1 | 5/2007 | Jeon et al. |
| 2007/0135817 A1 | 6/2007 | Ensign |
| 2007/0161987 A1 | 7/2007 | Capote et al. |
| 2007/0161994 A1 | 7/2007 | Lowery et al. |
| 2007/0167949 A1 | 7/2007 | Altarac et al. |
| 2007/0179501 A1 | 8/2007 | Firkins |
| 2007/0191844 A1 | 8/2007 | Carls et al. |
| 2007/0198014 A1 | 8/2007 | Graf et al. |
| 2007/0225711 A1 | 9/2007 | Ensign |
| 2007/0233087 A1 | 10/2007 | Schlapfer |
| 2007/0246614 A1 | 10/2007 | Allmann et al. |
| 2007/0250061 A1 | 10/2007 | Chin et al. |
| 2007/0250064 A1 | 10/2007 | Darois |
| 2007/0270805 A1 | 11/2007 | Miller |
| 2007/0270817 A1 | 11/2007 | Rezach |
| 2007/0270820 A1 | 11/2007 | Dickinson et al. |
| 2007/0270880 A1 | 11/2007 | Lindemann |
| 2007/0282339 A1 | 12/2007 | Schwab |
| 2007/0288004 A1 | 12/2007 | Alvarez |
| 2008/0039843 A1 | 2/2008 | Abdou |
| 2008/0058805 A1 | 3/2008 | Stuart |
| 2008/0058812 A1 | 3/2008 | Zehnder |
| 2008/0086126 A1 | 4/2008 | Miller |
| 2008/0103502 A1 | 5/2008 | Capote et al. |
| 2008/0140075 A1 | 6/2008 | Ensign |
| 2008/0140135 A1 | 6/2008 | Konieczynski et al. |
| 2008/0154308 A1 | 6/2008 | Sherman et al. |
| 2008/0177260 A1 | 7/2008 | McKinley et al. |
| 2008/0177323 A1 | 7/2008 | Null et al. |
| 2008/0188260 A1 | 8/2008 | Xiao et al. |
| 2008/0208257 A1 | 8/2008 | Matthys |
| 2008/0215095 A1 | 9/2008 | Biedermann et al. |
| 2008/0234743 A1 | 9/2008 | Marik |
| 2008/0243185 A1 | 10/2008 | Felix |
| 2008/0249570 A1 | 10/2008 | Carson et al. |
| 2008/0262552 A1 | 10/2008 | Kim |
| 2008/0262553 A1 | 10/2008 | Hawkins et al. |
| 2008/0269810 A1 | 10/2008 | Zhang et al. |
| 2008/0294194 A1 | 11/2008 | Capote et al. |
| 2008/0294202 A1 | 11/2008 | Peterson et al. |
| 2008/0312692 A1 | 12/2008 | Brennan et al. |
| 2009/0088803 A1 | 4/2009 | Justis et al. |
| 2009/0093847 A1 | 4/2009 | Wilcox |
| 2009/0105770 A1 | 4/2009 | Berrevoets |
| 2009/0149887 A1 | 6/2009 | Schlapfer et al. |
| 2009/0187217 A1 | 7/2009 | Weiman et al. |
| 2009/0198280 A1 | 8/2009 | Spratt et al. |
| 2009/0259256 A1 | 10/2009 | Miller |
| 2009/0270916 A1 | 10/2009 | Ramsay et al. |
| 2010/0004694 A1 | 1/2010 | Little |
| 2010/0042165 A1 | 2/2010 | Aflatoon |
| 2010/0057125 A1 | 3/2010 | Viker |
| 2010/0087864 A1 | 4/2010 | Klein et al. |
| 2010/0094345 A1 | 4/2010 | Saidha et al. |
| 2010/0145394 A1 | 6/2010 | Harvey et al. |
| 2010/0168797 A1 | 7/2010 | Graf |
| 2010/0191286 A1 | 7/2010 | Butler |
| 2010/0198272 A1 | 8/2010 | Keyer et al. |
| 2010/0241172 A1 | 9/2010 | Biyani et al. |
| 2010/0276051 A1 | 11/2010 | Kanehira |
| 2010/0298890 A1 | 11/2010 | Marino |
| 2010/0305621 A1 | 12/2010 | Wang |
| 2010/0313428 A1 | 12/2010 | Mocanu |
| 2010/0324599 A1 | 12/2010 | Montello |
| 2011/0106166 A1 | 5/2011 | Keyer et al. |
| 2011/0213424 A1 | 9/2011 | Biedermann et al. |
| 2011/0230917 A1 | 9/2011 | Carson et al. |
| 2011/0270325 A1 | 11/2011 | Keyer et al. |
| 2011/0276051 A1 | 11/2011 | Blakemore et al. |
| 2012/0010629 A1 | 1/2012 | Mire et al. |
| 2012/0089194 A1 | 4/2012 | Wolf |

(56) References Cited

U.S. PATENT DOCUMENTS

| | | |
|---|---|---|
| 2012/0109200 A1 | 5/2012 | Cahill et al. |
| 2012/0265249 A1 | 10/2012 | Fielding et al. |
| 2013/0012955 A1 | 1/2013 | Lin et al. |
| 2013/0012995 A1 | 1/2013 | Butterfield et al. |
| 2013/0079827 A1 | 3/2013 | Neary et al. |
| 2013/0261680 A1 | 10/2013 | Baccelli et al. |
| 2013/0268011 A1 | 10/2013 | Rezach et al. |

FOREIGN PATENT DOCUMENTS

| | | |
|---|---|---|
| CN | 102458279 A | 5/2012 |
| DE | 9314297 U1 | 4/1994 |
| DE | 4329220 A1 | 9/1995 |
| DE | 29903342 U1 | 6/1999 |
| DE | 29810798 U1 | 10/1999 |
| DE | 19912364 A1 | 10/2000 |
| DE | 20207785 U1 | 9/2003 |
| EP | 0408489 A1 | 1/1991 |
| EP | 0 674 880 | 10/1995 |
| EP | 0807420 B1 | 5/1997 |
| EP | 0612507 B1 | 12/1998 |
| EP | 0683644 B1 | 6/2000 |
| EP | 1210914 A1 | 6/2002 |
| EP | 1248573 | 10/2002 |
| EP | 1 269 929 | 1/2003 |
| EP | 1294297 B1 | 3/2003 |
| EP | 1316295 A2 | 6/2003 |
| EP | 1323391 A2 | 7/2003 |
| EP | 0828459 | 9/2003 |
| EP | 0 837 656 | 12/2003 |
| EP | 1637085 | 3/2006 |
| EP | 1313403 B1 | 10/2006 |
| EP | 1 198 205 | 11/2006 |
| EP | 1741396 | 1/2007 |
| EP | 1665994 B1 | 6/2008 |
| EP | 1961392 A1 | 8/2008 |
| EP | 2052690 | 4/2009 |
| GB | 2414674 B | 8/2008 |
| JP | 06-154258 | 6/1994 |
| JP | 08-112291 A | 5/1996 |
| JP | 2005-510286 | 4/2005 |
| JP | 2006-508748 A | 3/2006 |
| JP | 2006-154258 | 6/2006 |
| JP | 2006-525102 | 11/2006 |
| JP | 2009-535114 A | 10/2009 |
| JP | 2012-523927 A | 10/2012 |
| JP | 2012-530550 A | 12/2012 |
| KR | 10-2008-0112851 A | 12/2008 |
| KR | 100896043 B1 | 5/2009 |
| KR | 10-2012-0013312 A | 2/2012 |
| KR | 10-2012-0039622 A | 4/2012 |
| WO | 94/17736 A1 | 8/1994 |
| WO | 96/32071 A1 | 10/1996 |
| WO | WO 97/02786 | 1/1997 |
| WO | WO 1998/052482 A1 | 11/1998 |
| WO | WO 00/21455 | 4/2000 |
| WO | 01/06940 A1 | 2/2001 |
| WO | 01/52758 A1 | 7/2001 |
| WO | WO 02/00124 A1 | 1/2002 |
| WO | 02/17803 A2 | 3/2002 |
| WO | WO 02/076314 A1 | 10/2002 |
| WO | WO 2003/045261 A1 | 6/2003 |
| WO | WO 2004/052218 A1 | 6/2004 |
| WO | WO 2004/089245 | 10/2004 |
| WO | WO 2004/098425 | 11/2004 |
| WO | WO 2005/016161 A1 | 2/2005 |
| WO | WO 2006/088452 A2 | 8/2006 |
| WO | 2006/114437 A1 | 11/2006 |
| WO | WO 2006/116437 | 11/2006 |
| WO | WO 2007/038350 | 4/2007 |
| WO | WO 2007/045892 A1 | 4/2007 |
| WO | WO 2007/047711 A2 | 4/2007 |
| WO | 2007/127632 A2 | 11/2007 |
| WO | WO 2007/146032 | 12/2007 |
| WO | WO 2008/027940 | 3/2008 |
| WO | WO 2008/048953 A2 | 4/2008 |
| WO | 2008/069420 A1 | 6/2008 |
| WO | WO 2008/089096 A2 | 7/2008 |
| WO | WO 2008/146185 A1 | 12/2008 |
| WO | WO 2009/001978 A1 | 12/2008 |
| WO | WO 2009/015100 | 1/2009 |
| WO | WO 2010/030906 | 3/2010 |
| WO | WO 2010/028287 A3 | 6/2010 |
| WO | WO 2010/120989 | 10/2010 |
| WO | WO 2010/148231 A1 | 12/2010 |
| WO | WO 2012/154772 A2 | 11/2012 |

OTHER PUBLICATIONS

International Patent Application No. PCT/US2010/031178: Notification of Transmittal of the International Preliminary Report on Patentability dated Jun. 14, 2011, 12 pages.
International Patent Application No. PCT/US2010/039037: International Search Report dated Jan. 9, 2010, 5 pages.
International Patent Application No. PCT/US2010/039037: International Preliminary Report on Patentability dated Jul. 11, 2011.
International Patent Application No. PCT/US2009/056692: International Search Report and Written Opinion dated Dec. 3, 2009, 14 pages.
International Patent Application No. PCT/US2008/070670: International Search Report dated Feb. 17, 2009, 3 pages.
International Patent Application No. PCT/US2008/070670: International Preliminary Report on Patentability, 6 pages.
Aebi et al., "AO ASIF Principles in Spine Surgery", Springer, 1998, 186-190.
International Patent Application No. PCT/US2006/037120: International Search Report dated Jul. 11, 2007, 4 pages.
International Patent Application No. PCT/US2006/047986: International Search Report dated May 2, 2007, 2 pages.
International Preliminary Report on Patentability dated May 3, 2011 in PCT application PCT/US2009/063056.

* cited by examiner

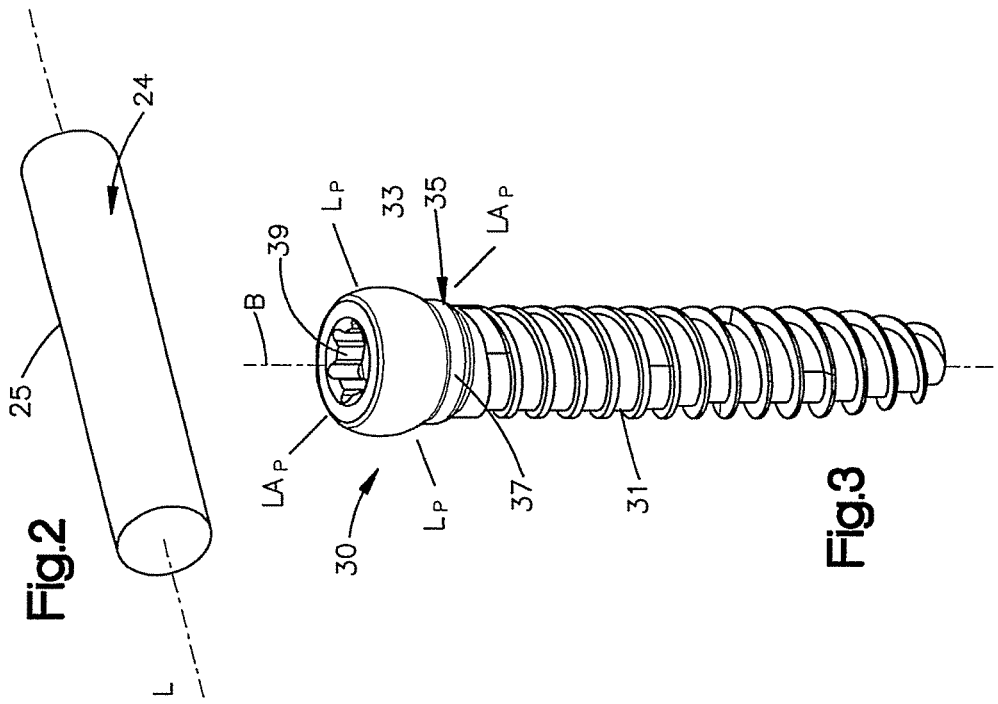
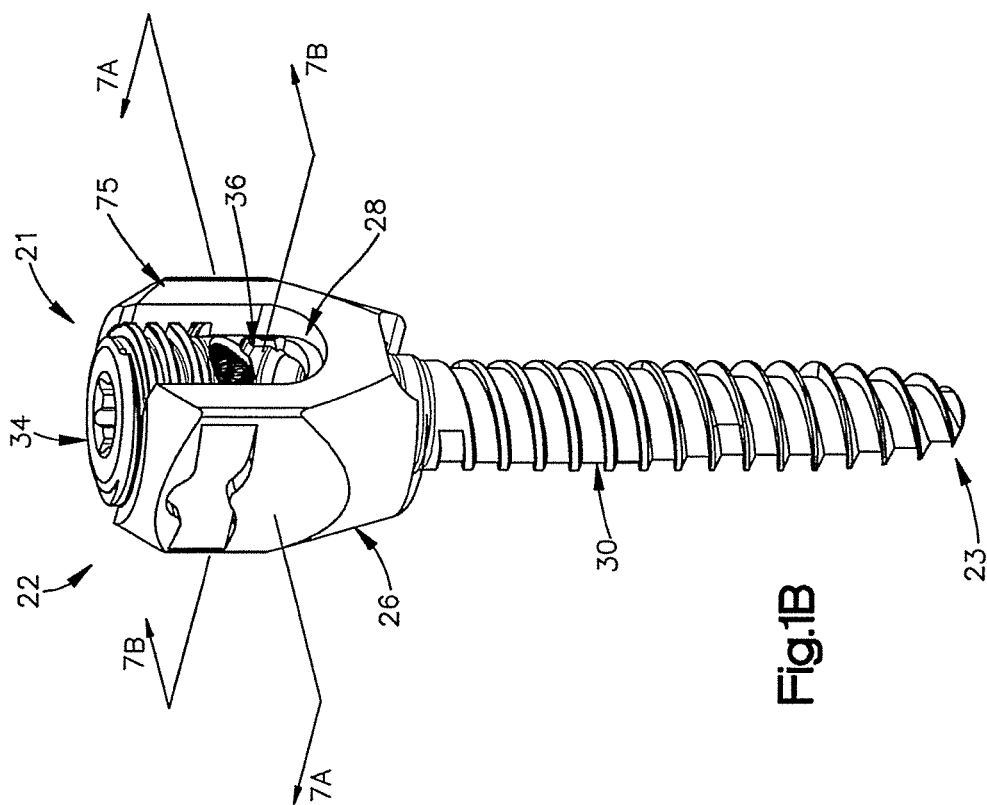

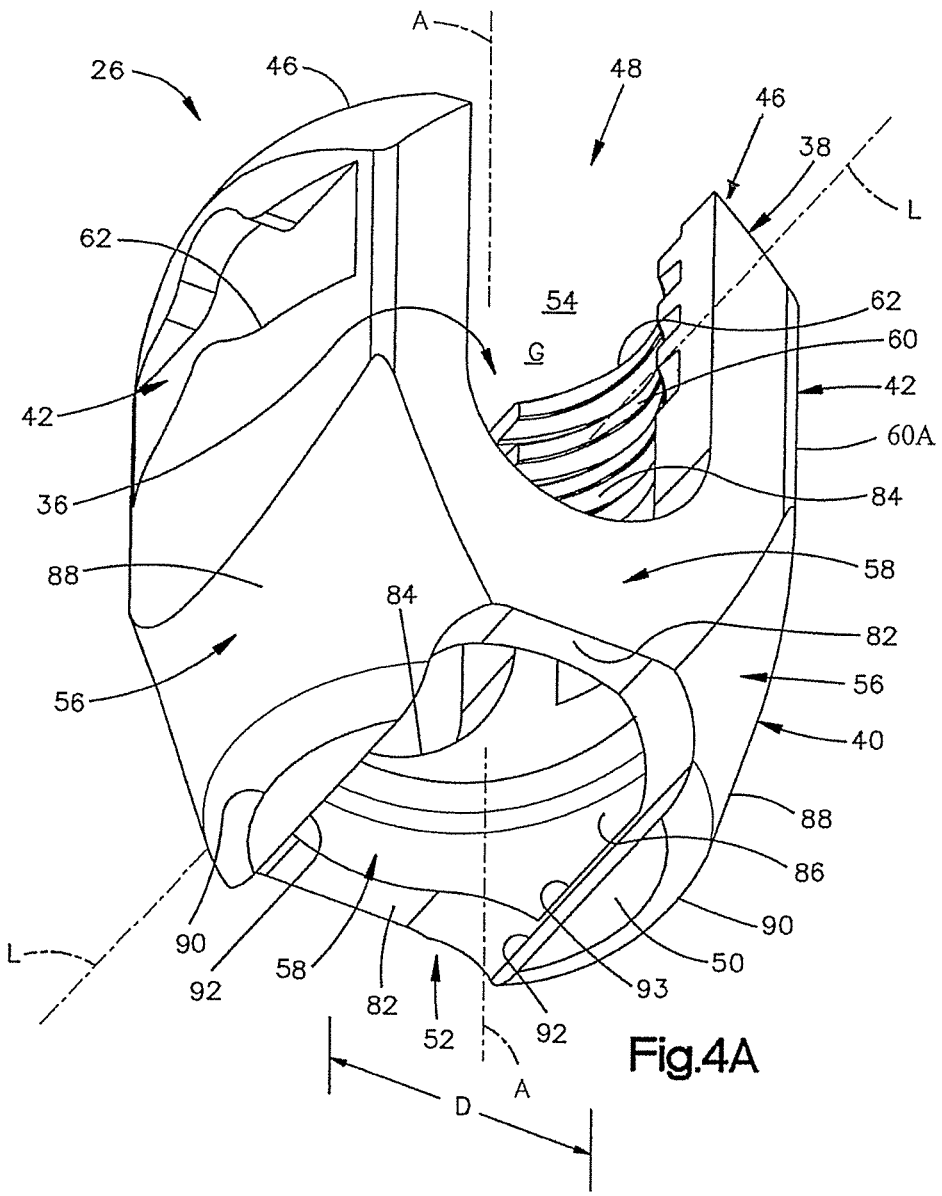
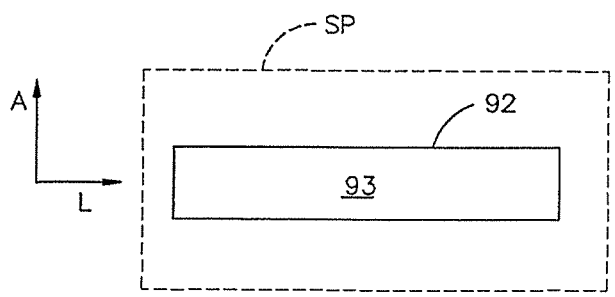
Fig.4A
Fig.4B

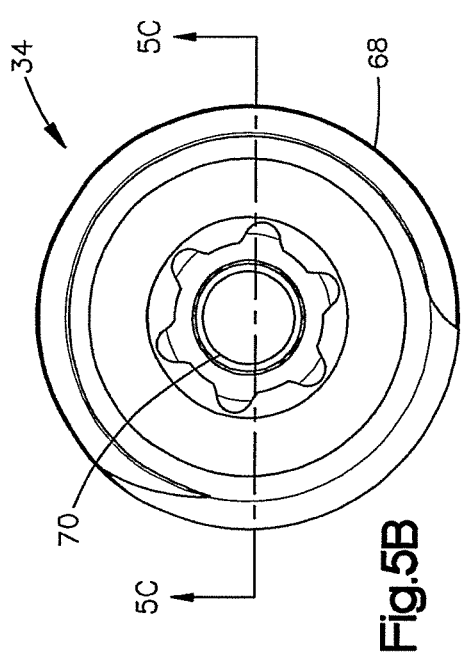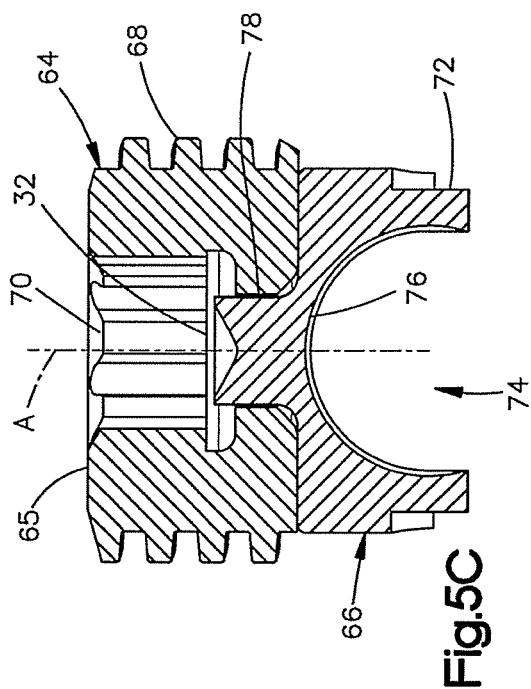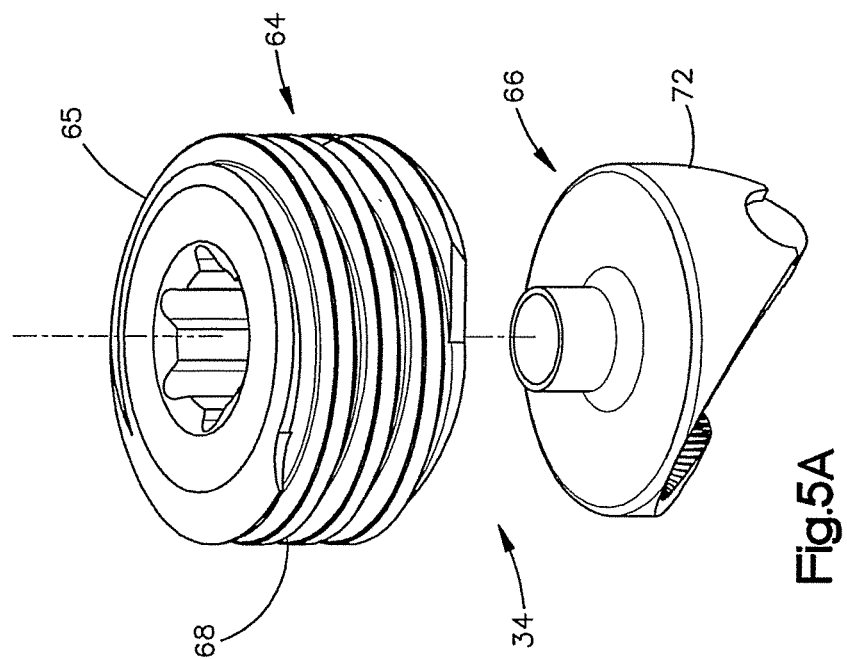

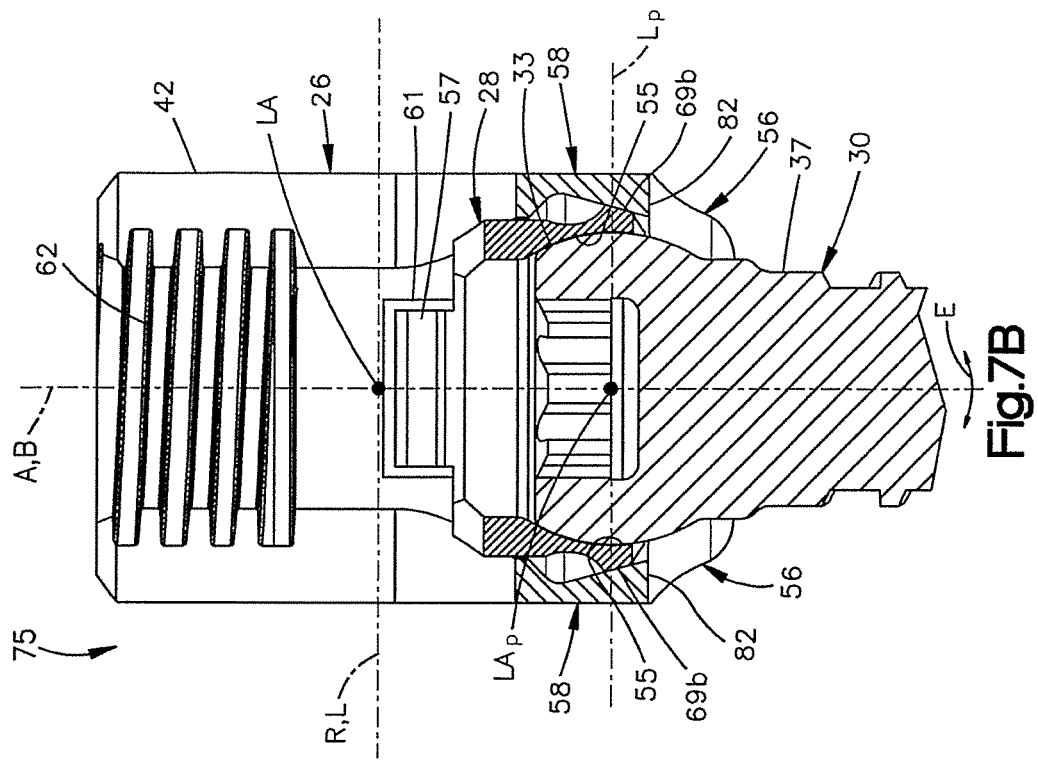
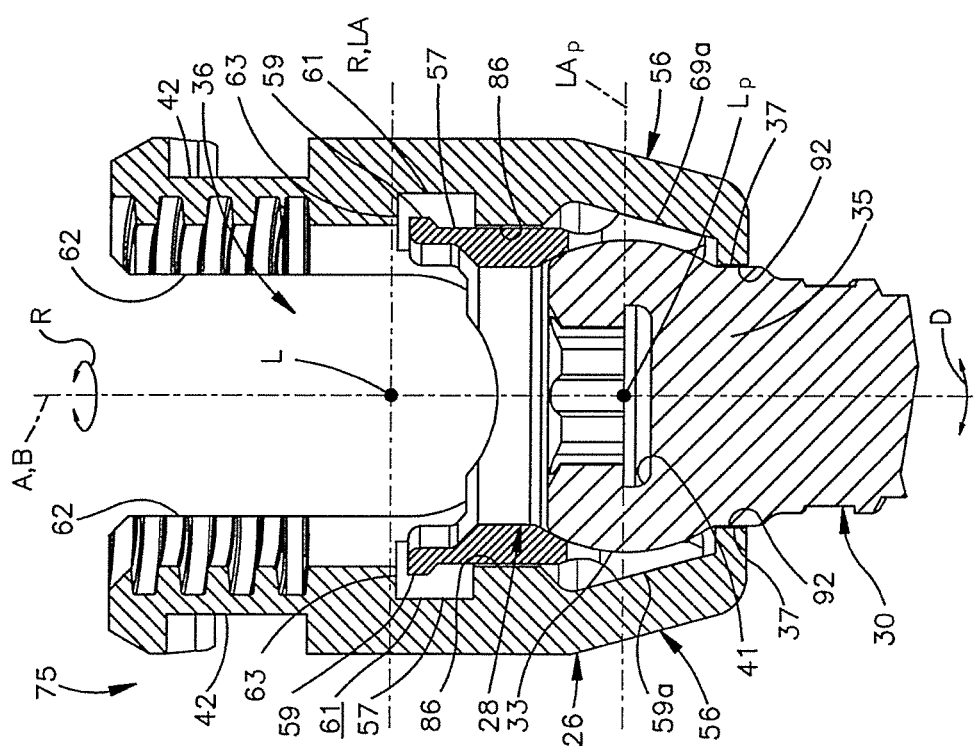

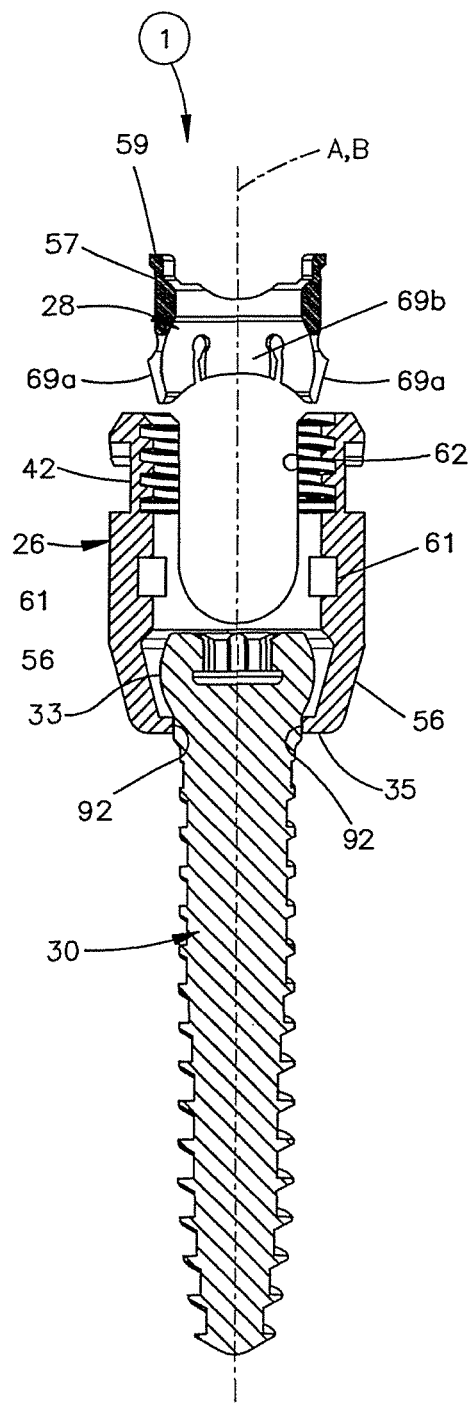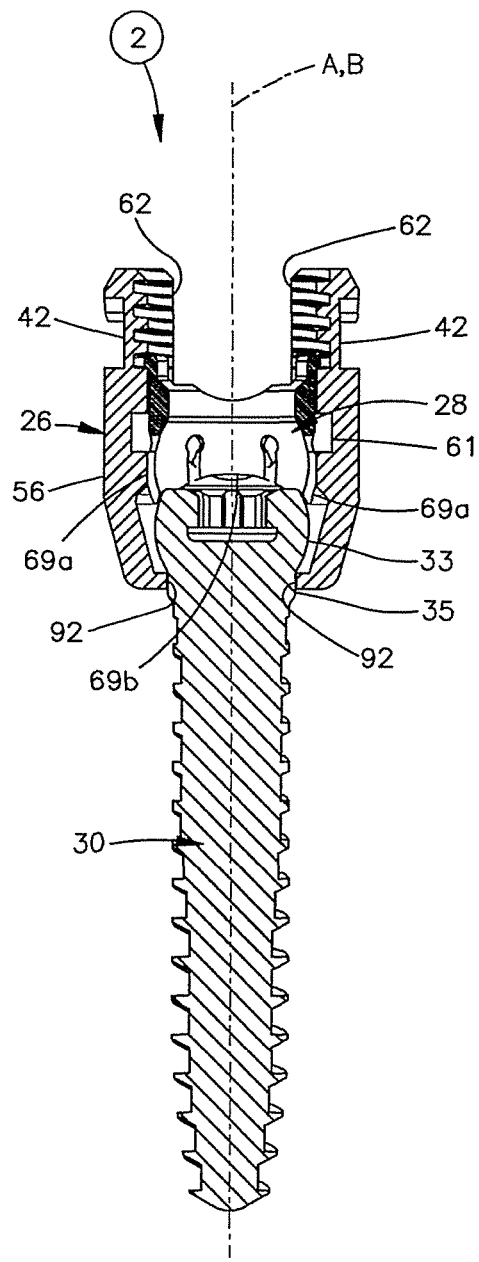
Fig.8A
Fig.8B

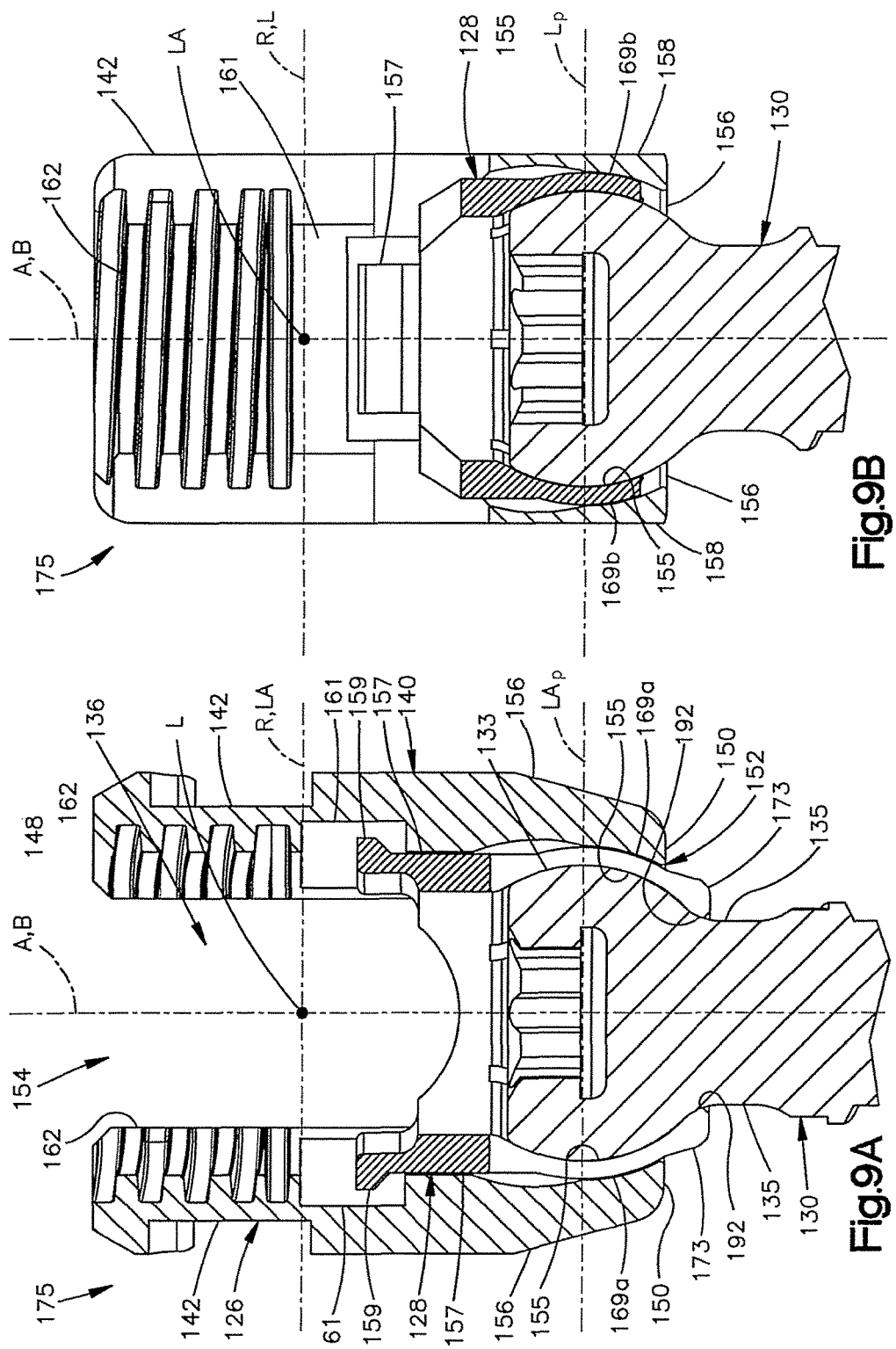

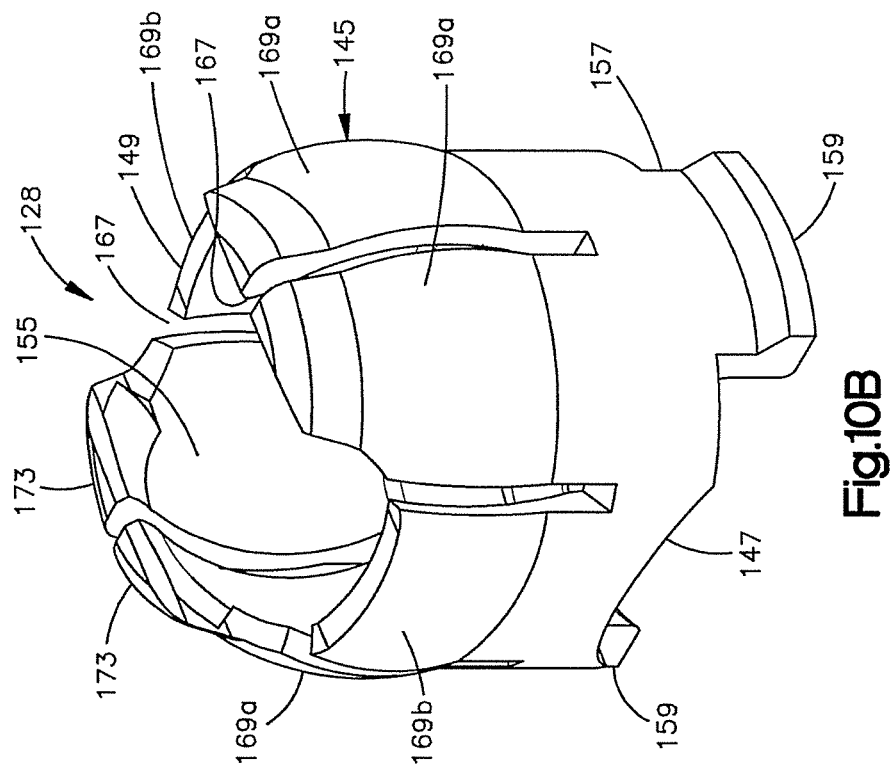
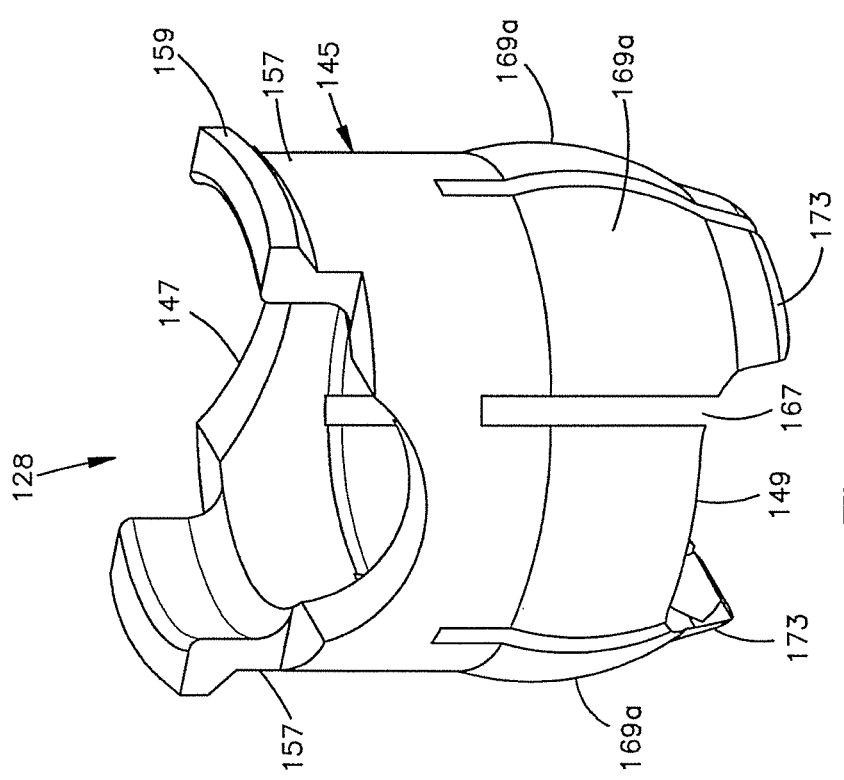

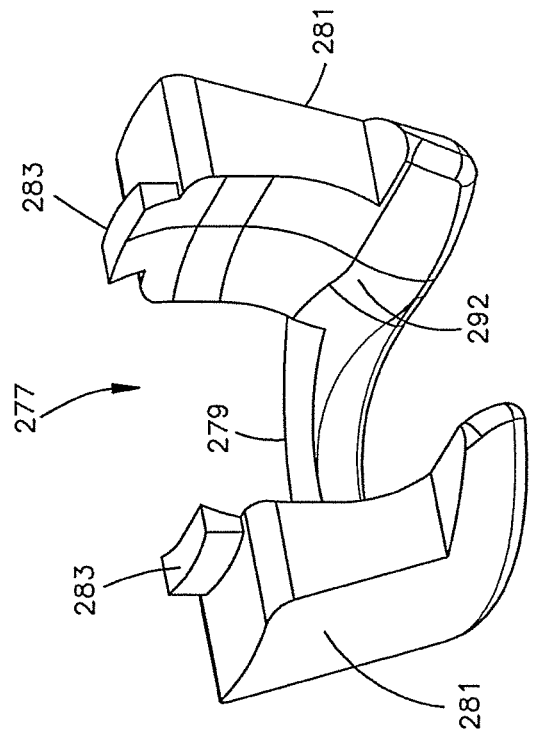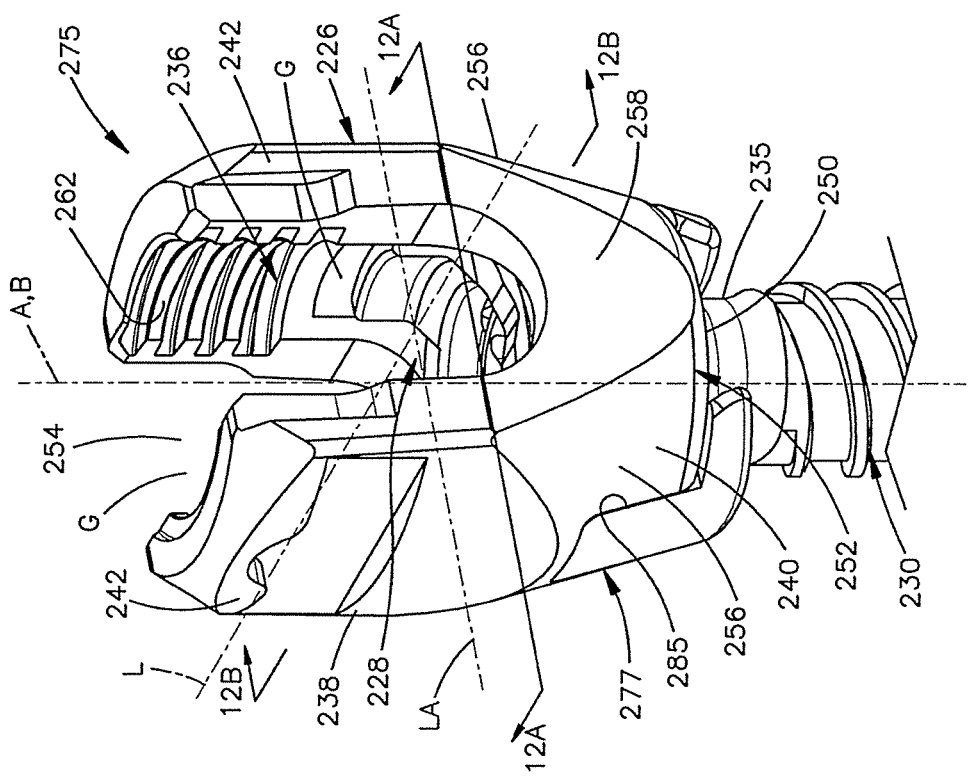

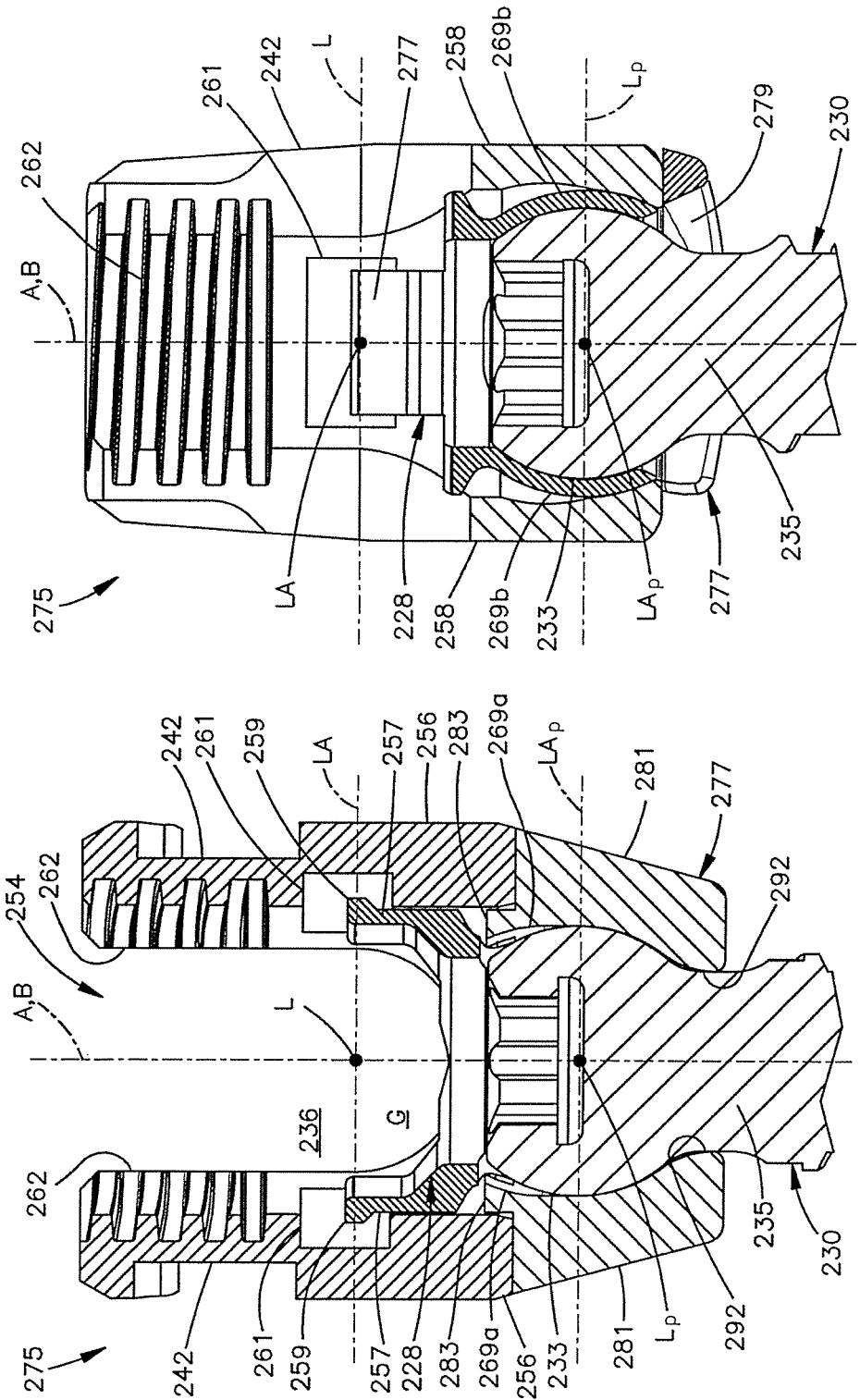

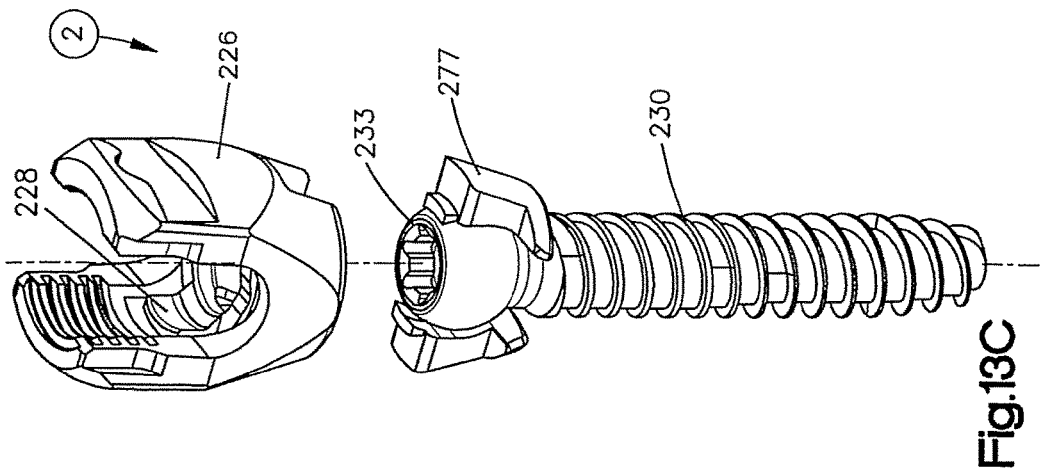
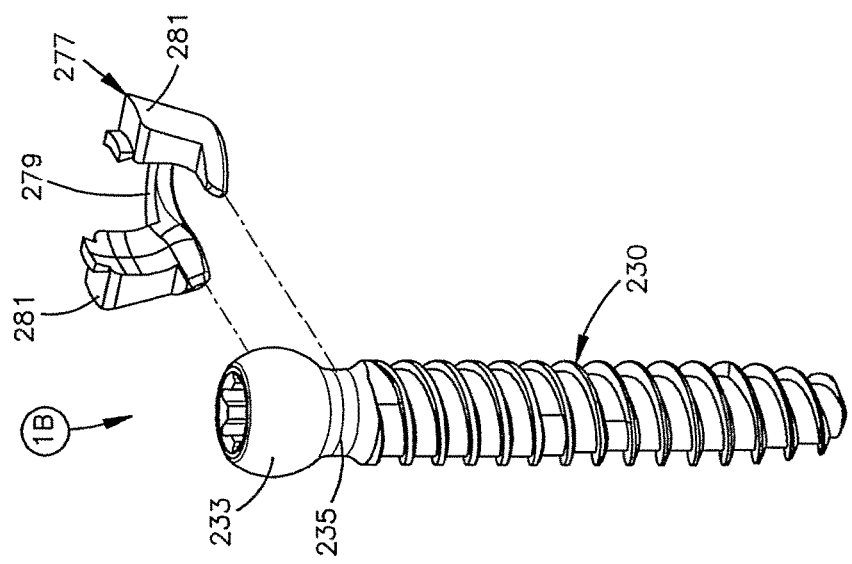
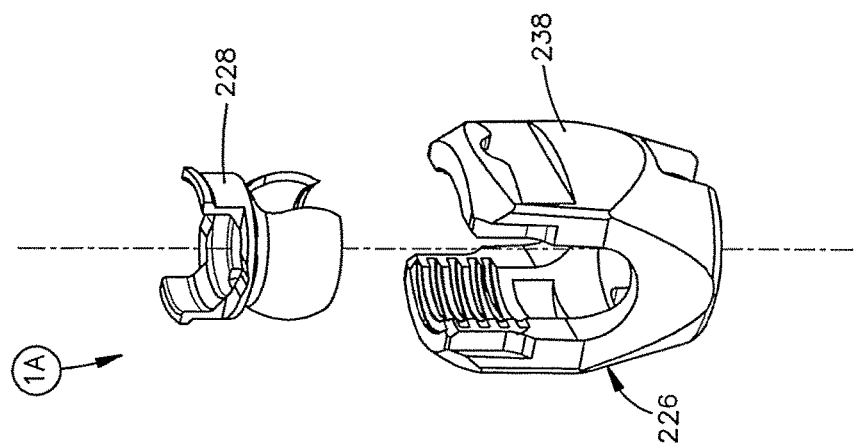

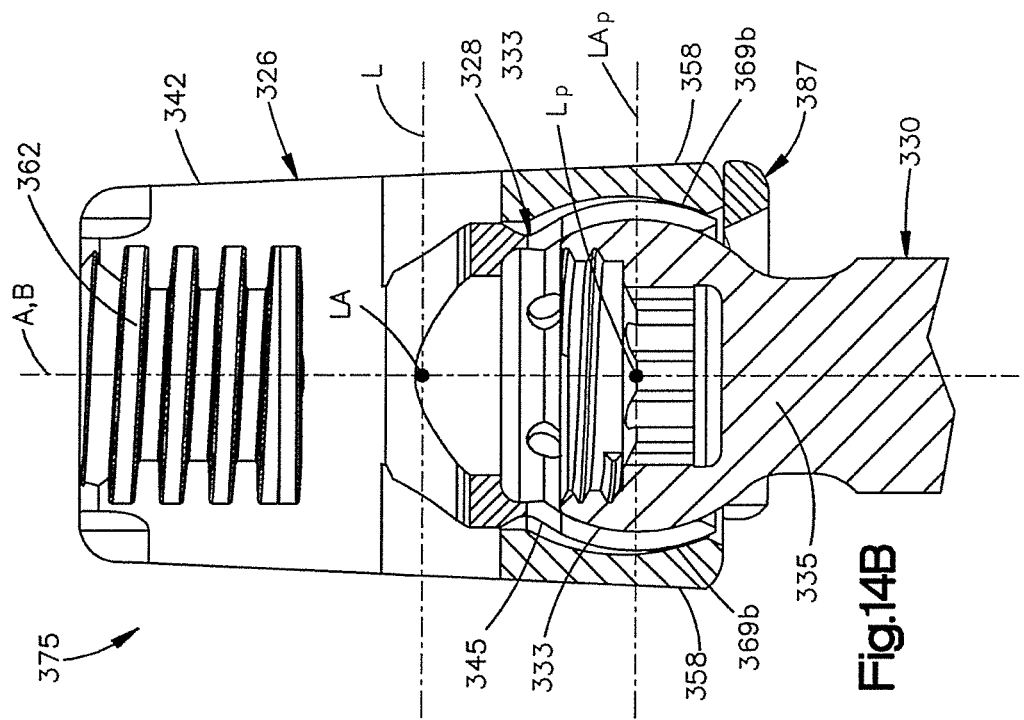
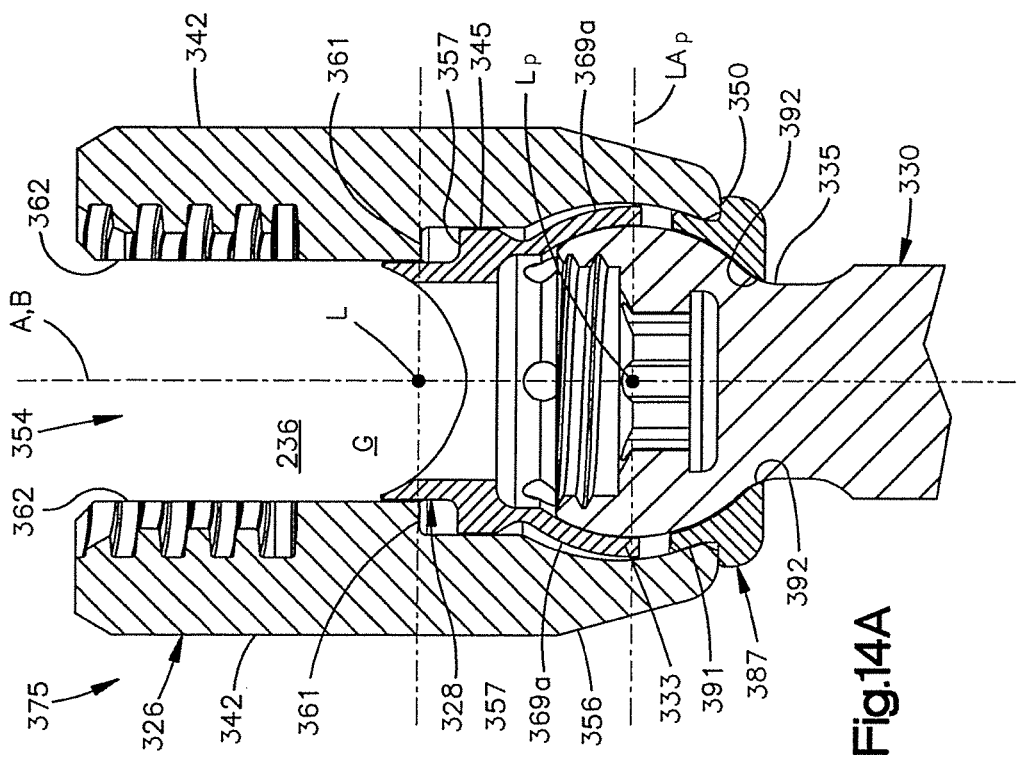

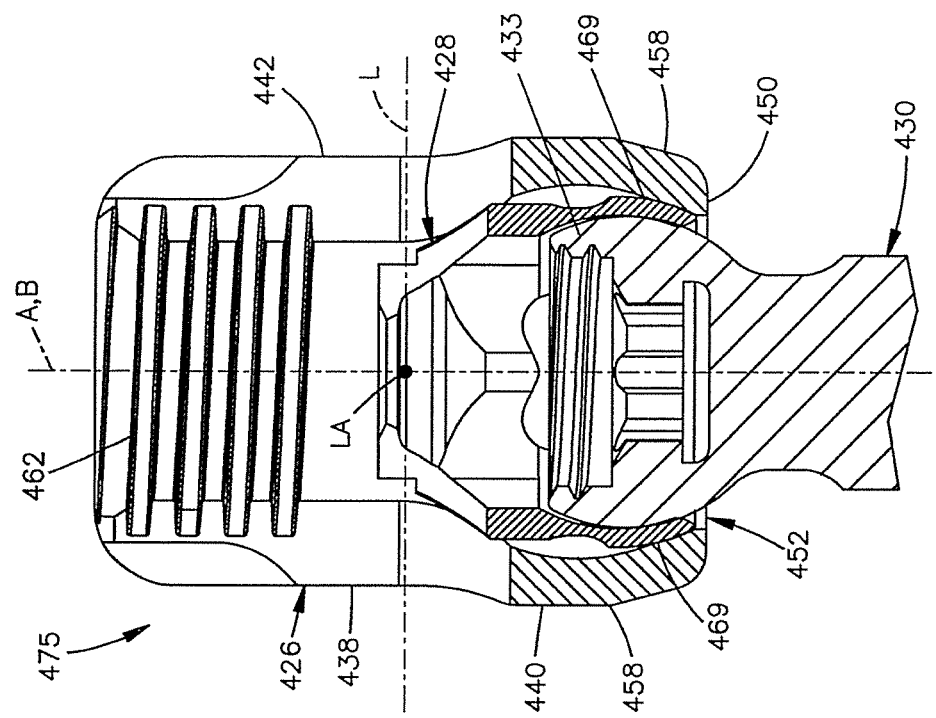
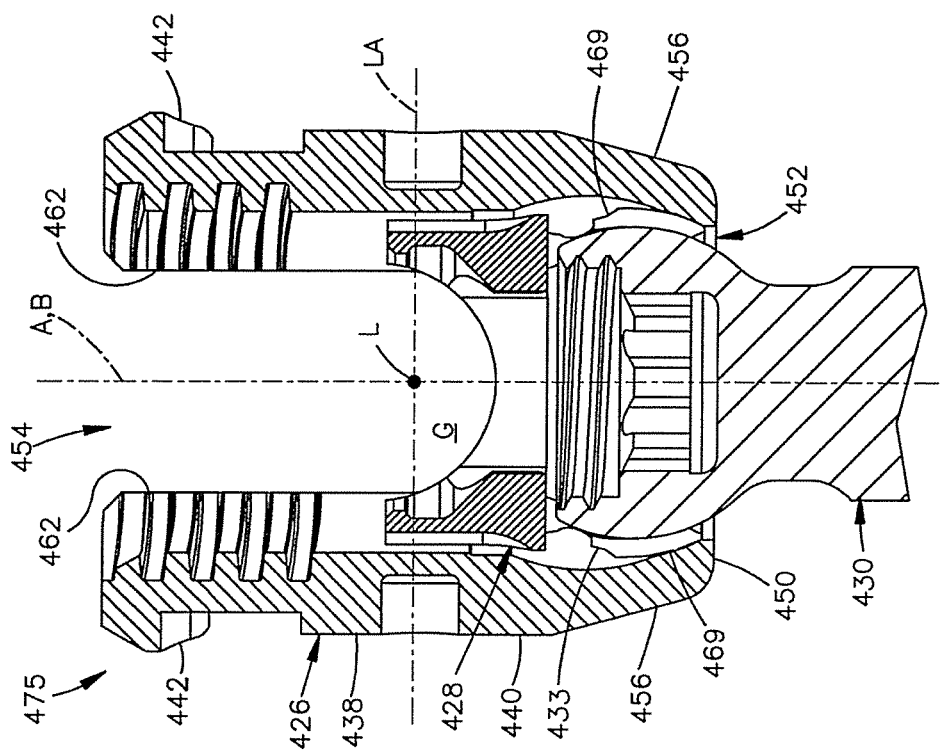

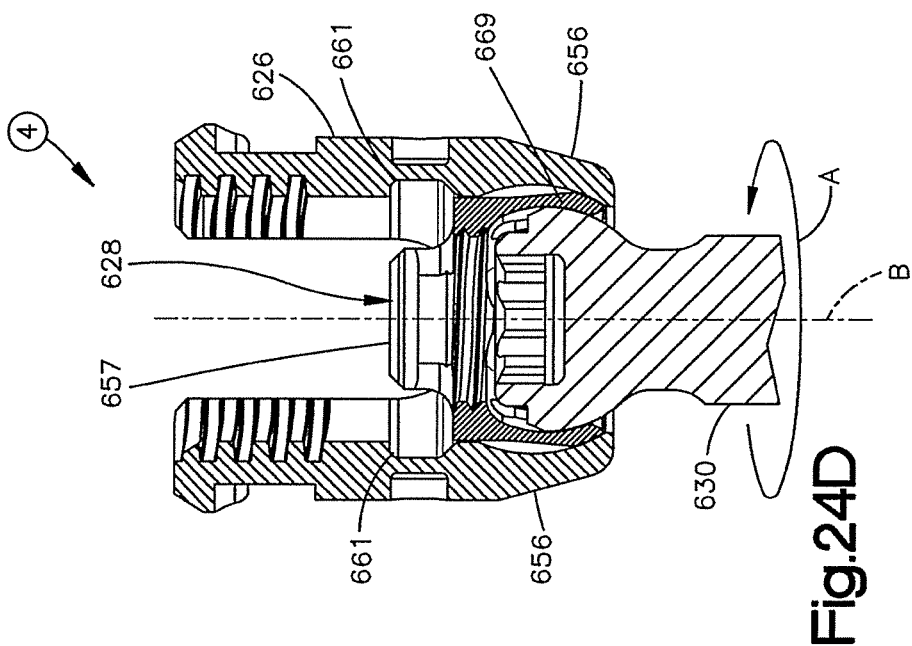
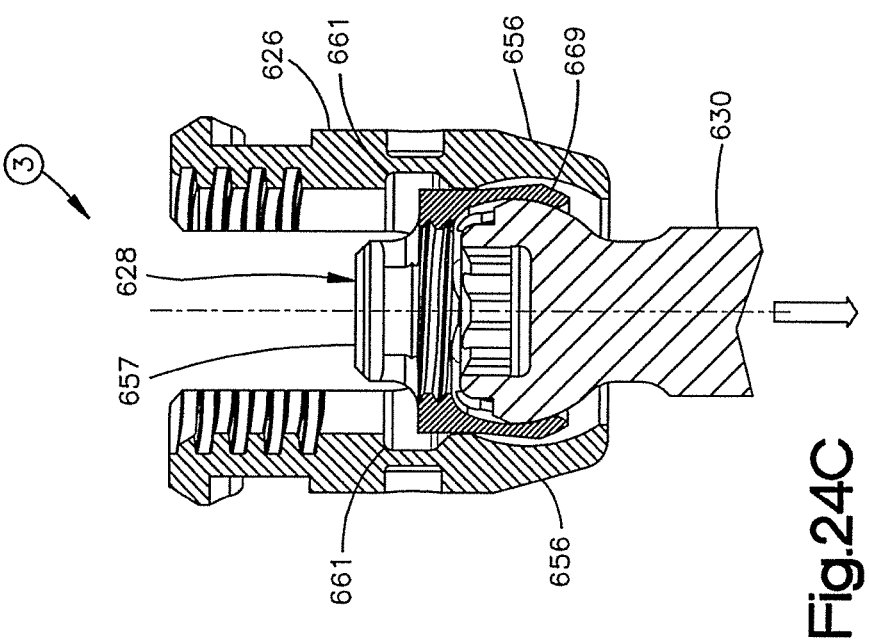
Fig.24C
Fig.24D

UNI-PLANER BONE FIXATION ASSEMBLY

CROSS-REFERENCE TO RELATED APPLICATIONS

This application is a continuation of U.S. patent application Ser. No. 14/143,489, filed Dec. 30, 2013, which is a continuation of U.S. patent application Ser. No. 12/611,286, filed Nov. 3, 2009, which claims the benefit of U.S. Patent Application Ser. No. 61/110,704, filed Nov. 3, 2008, the contents of each of which are hereby incorporated by reference as if set forth in their entirety herein. This is related by subject matter to PCT Patent Application Serial No. PCT/US2008/070670, having an international filing date of Jul. 21, 2008, the contents of which are hereby incorporated by reference as if set forth in their entirety herein.

BACKGROUND

Conventional bone fixation elements, such as pedicle screws, include a bone anchor retained within an anchor seat and captured by a collet. Pedicle screw assemblies include a plurality of pedicle screws joined by a rod that extends through rod slots formed in the pedicle screws. Uni-planar pedicle screws provide one degree of freedom. That is, the bone anchor retained within the anchor seat and, in some systems, the collet, is free to move with respect to the anchor seat in only one plane, e.g., the sagittal plane. Motion of the bone anchor is limited to this sagittal plane in conventional pedicle screws by a pinning or staking process during manufacture of the assemblies to create a pivot in the sagittal plane. As a result, the height of the bone screw is limited by the orientation of the rod slot. Unfortunately, if the rod slot isn't in line with the trajectory of the rod, the anchor seat must be turned, which results in either advancing or withdrawing the screw toward and away from the bone surface.

It is therefore desirable to provide a bone fixation element that allows the screw head to angulate in a desired plane while also allowing the bone anchor to rotate freely with respect to the anchor seat without advancing or withdrawing the screw toward or away from the bone surface.

SUMMARY

In one embodiment, a bone fixation subassembly is configured to receive a fixation rod and a locking cap. The bone fixation subassembly includes an anchor seat and a collet. The anchor seat includes an anchor seat body extending along a central axis and defining an upper end and a lower end. The upper end includes a pair of opposing fixation rod-receiving gaps therebetween that are spaced along a longitudinal axis, and a bore disposed between the rod-receiving gaps. The collet includes a collet body disposed in the anchor seat. The collet body is configured to attach to a bone anchor that extends along an axis of rotation. A bone anchor attached to the collet is permitted to rotate about the axis of rotation relative to the anchor seat, and the bone anchor is further permitted to pivot relative to the anchor seat along a desired plane. The bone anchor is prevented from pivoting in another plane that includes the central axis and is angularly offset with respect to the desired plane.

BRIEF DESCRIPTION OF THE DRAWINGS

The foregoing summary, as well as the following detailed description of the preferred embodiments of the application, will be better understood when read in conjunction with the appended drawings. For the purposes of illustrating the sagittal pedicle screw systems of the present application, there is shown in the drawings preferred embodiments. It should be understood, however, that the application is not limited to the precise arrangements and instrumentalities shown. In the drawings:

FIG. 1B is a perspective view of one of the bone fixation elements illustrated in FIG. 1A constructed in accordance with one embodiment, including an anchor seat, a bone anchor, a collet, and a locking cap;

FIG. 2 is a perspective view of the bone fixation rod illustrated in FIG. 1A;

FIG. 3 is a perspective view of the bone anchor illustrated in FIG. 1B;

FIG. 4A is a perspective view of the anchor seat illustrated in FIG. 1B;

FIG. 4B is an enlarged portion of a guide provided by the anchor seat illustrated in FIG. 4A;

FIG. 5A is an exploded perspective view of the locking cap illustrated in FIG. 1B;

FIG. 5B is a top plan view of the locking cap illustrated in FIG. 5A;

FIG. 5C is a sectional side elevation view of the locking cap illustrated in FIG. 5B;

FIG. 7A is a sectional side elevation view of the bone fixation element illustrated in FIG. 1B taken along line 7A-7A, with the locking cap removed, to illustrate a bone fixation subassembly;

FIG. 7B is a sectional side elevation view of the bone fixation subassembly illustrated in FIG. 7A, and taken along line 7B-7B of FIG. 1B;

FIG. 8A is a schematic view illustrating a method for assembling the bone fixation element illustrated in FIG. 1A;

FIG. 8B is a schematic view illustrating the method for assembling the bone fixation element illustrated in FIG. 1A, and showing the collet being inserted into the axial bore of the bone anchor;

FIG. 9A is a sectional side elevation view of a bone fixation subassembly constructed in accordance with an alternative embodiment, taken from the same orientation as FIG. 7A;

FIG. 9B is a sectional side elevation view of the bone fixation illustrated in FIG. 9A, taken from the same orientation as FIG. 7B;

FIG. 10A is a top perspective view of a collet of the bone fixation subassembly illustrated in FIGS. 9A-B;

FIG. 10B is a bottom perspective view of the collet illustrated in FIG. 10A;

FIG. 11A is a perspective view of a bone fixation subassembly including an anchor seat extension constructed in accordance with an alternative embodiment;

FIG. 11B is a perspective view of the anchor seat extension illustrated in FIG. 11A;

FIG. 12A, is a sectional side elevation view of the bone fixation subassembly illustrated in FIG. 11A, taken along line 12A-12A;

FIG. 12B, is a sectional side elevation view of the bone fixation subassembly illustrated in FIG. 11A, taken along line 12B-12B;

FIG. 13A is a schematic view illustrating a method for assembling the bone fixation subassembly illustrated in FIG. 11;

FIG. 13B is a schematic view illustrating the method for assembling the bone fixation subassembly illustrated in FIG. 11, and showing the anchor seat extension being attached to the bone anchor by clipping the collar over the anchor neck;

FIG. 13C is a schematic view illustrating the method for assembling the bone fixation subassembly illustrated in FIG. 11, and showing the anchor body being brought down onto the anchor head;

FIG. 14A is a sectional side elevation view similar to FIG. 12A, but of a bone fixation subassembly constructed in accordance with another embodiment including a collet extension;

FIG. 14B is a sectional side elevation view similar to FIG. 12A, but of the bone fixation subassembly illustrated in FIG. 14A;

FIG. 19A is a sectional side elevation view of the bone fixation subassembly illustrated in FIG. 18, taken along line 19A-19A;

FIG. 19B is a sectional side elevation view of the bone fixation subassembly illustrated in FIG. 18, taken along line 19B-19B;

FIG. 24C is a schematic view illustrating a method for assembling the bone fixation subassembly illustrated in FIG. 23, and showing a downward force being applied on the anchor relative to the anchor seat to thereby bring the collet to an intermediate insertion position;

FIG. 24D is a schematic view illustrating a method for assembling the bone fixation subassembly illustrated in FIG. 23, and showing the collet being rotated until the flanges are brought into alignment with the recesses;

DETAILED DESCRIPTION

Figure 1A:
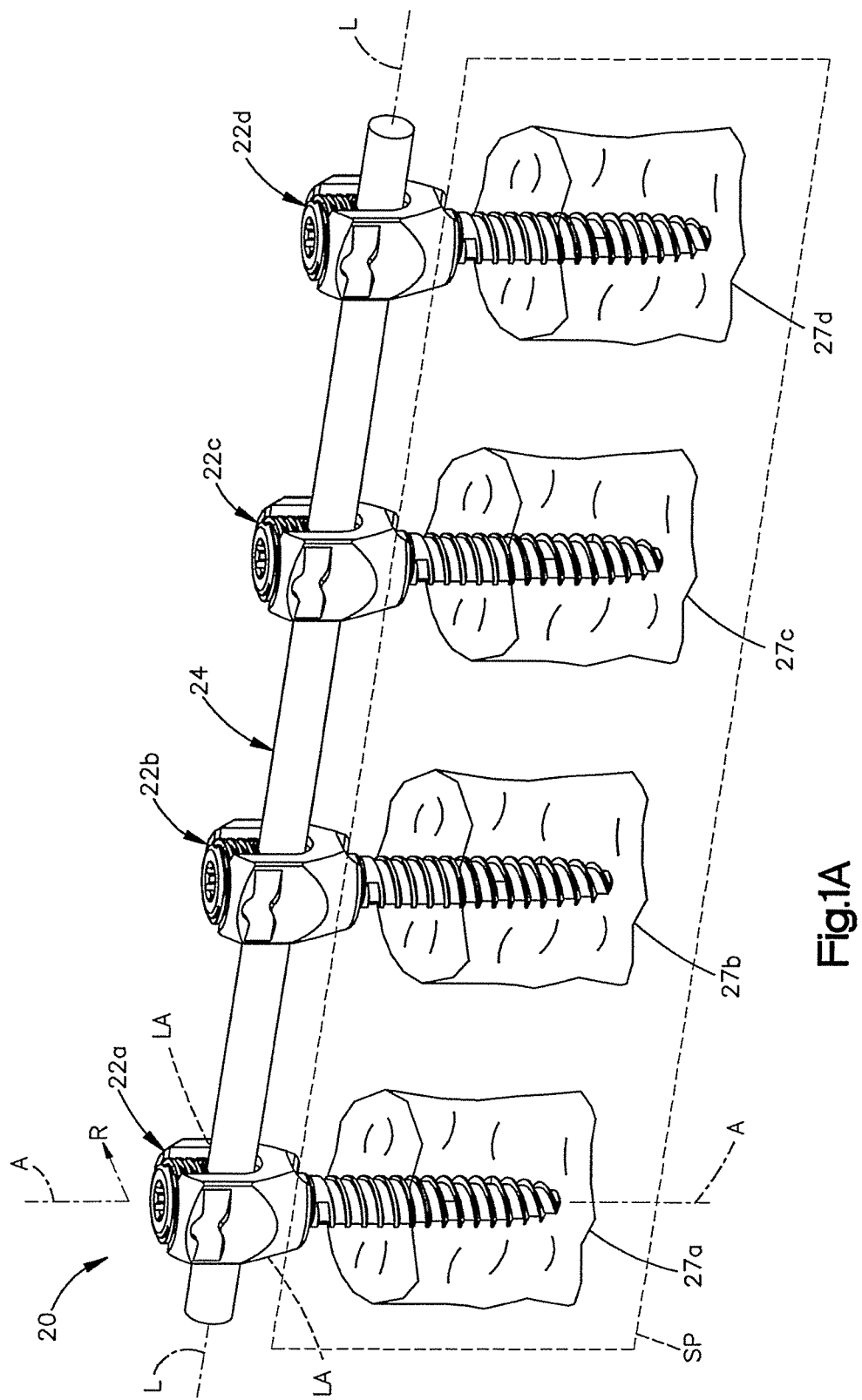
FIG. 1A is a perspective view of a bone fixation assembly constructed in accordance with one embodiment including a plurality of bone fixation elements connected by a bone fixation rod, and illustrated schematically as each being affixed to a vertebra.

Certain terminology may be used in the following description for convenience only and should not be considered as limiting in any way. For instance, a bone fixation assembly 20 includes one or more bone fixation elements 22, and four bone fixation elements 22A-D as illustrated in FIG. 1A. As shown in FIG. 1B, each bone fixation element 22 extends vertically along an axial direction A, and generally horizontally along a radial direction R extends perpendicular to the axial direction A. Thus, the radial direction R includes a longitudinal direction L and a lateral direction LA that extends perpendicular to the longitudinal direction L. It should be appreciated that the directional terms "longitudinal," "lateral," can likewise apply to the bone fixation assembly 20 as extending horizontally, and the directional term "transverse" can refer to a vertical direction. The bone fixation element 22 defines an upper end 21 and a lower end 23, such that the directional terms "upper" and "lower" and derivatives thereof refer to a direction from the lower end 23 towards the upper end 21, and from the upper end 21 towards the lower end 23, respectively.

The words "inward," "outward," "upper," "lower," "distal," and "proximal," refer to directions toward or away from, respectively, the geometric center of the bone fixation assembly 20 and its components. The words, "anterior", "posterior", "superior," "inferior" and related words and/or phrases designate preferred positions and orientations in the human body to which reference is made and are not meant to be limiting. It should further be appreciated that while round structures define diameters as described herein, the round structures could be replaced with alternative (e.g., polygonal) structures which would define alternative cross-sectional dimensions opposed to diameters. The term "diameter" as used herein is intended to include all such alternatives unless otherwise specified. The terminology includes the above-listed words, derivatives thereof and words of similar import.

It should be appreciated that the directional terms are used herein with reference to the orientation of the bone fixation assembly 20 and its components as illustrated, and that the actual orientation of the bone fixation assembly 20 and its components may change during use. For instance, the axial direction is illustrated as extending along a vertical direction, and the radial direction is illustrated as extending along a horizontal direction, however the directions that encompass the various directions may differ during use, depending, for instance, on the desired orientation of the bone fixation assembly 20 during use. Accordingly, the directional terms are used herein merely for the purposes of clarity and convenience only, in a non-limiting manner.

Referring now to FIG. 1A, the bone fixation assembly 20 includes a plurality of bone fixation elements, such as bone fixation elements 22A-D, connected by a fixation rod 24 that extends along a longitudinal axis L. The bone fixation elements 22A-D each include a bone anchor 30 that is implanted (e.g., screwed) into a corresponding vertebra 27A-D. Unless otherwise specified, the bone fixation assembly 20 and its components can be made from titanium-aluminum-niobium alloy (TAN), implant-grade 316L stainless steel, or any suitable alternative implant-grade material.

With continuing reference to FIG. 1A, the bone fixation elements 22A-D will be described as and may be generally implanted in the spine, for instance at the pedicle portion of a lumbar, thoracic, or cervical vertebral body. In this regard, when the bone fixation elements 22A-D are joined by the rod 24, the assembly 20 fixes the relative position of the vertebrae (illustrated schematically at 27A-D). Accordingly, the bone fixation elements 22A-D can be referred to as spine fixation elements or pedicle screw assemblies, the fixation rod 24 can be referred to as a spinal rod, and the bone fixation assembly 20 can be referred to as a spine fixation assembly. However, it should be appreciated that the bone fixation assembly 20 can also be used for fixation of other parts of the body, such as joints, long bones, or bones in the hands, face, feet, extremities, cranium, and the like.

As shown in FIG. 2, the fixation rod 24 is elongate along a longitudinal axis L, and includes a body 25 that is cylindrical or tubular in shape. The longitudinal axis L extends generally in a cranial-caudal direction, or in the sagittal plane, when the bone fixation assembly is affixed to the spine. The rod body 25 may include, but is not limited to, a solid body, a non-solid body, a flexible or dynamic body, or the like, and can assume any alternative shape as desired. It should thus be appreciated that the bone fixation assembly 20 is not limited in use to any particular fixation rod 24.

Referring now to FIG. 1B, the bone fixation elements 22A-D of the bone fixation assembly 20 will now be described with respect to the bone fixation element 22. In particular, the bone fixation element 22 generally includes a bone fixation subassembly 75, and a locking cap 34. The subassembly 75 is illustrated as including a bone anchor seat 26, a collet 28 disposed inside the anchor seat 26, a bone anchor 30 (shown as a threaded bone screw) having a head portion 33 (see FIG. 3) attached to the collet 28. The locking cap 34 is installed in the anchor seat 26 at a location above the collet 28, such that the fixation rod 24 is located in a rod slot 36 that is disposed, and as illustrated defined, between the collet 28 and the locking cap 34. As will be appreciated from the description below, the bone anchor 30 is free to pivot with respect to the anchor seat 26 in a desired plane, which can be the sagittal plane, and can further freely rotate relative to the anchor seat 26. Because pivotal motion of the bone anchor is limited to the desired plane, the bone fixation elements 22 can be referred to as a uni-planar bone fixation element, and the bone fixation assembly can be referred to as a uni-planar bone fixation assembly.

Referring also to FIG. 3, the bone anchor 30 is configured as a bone screw, or pedicle screw, that includes an externally threaded shaft 31 coupled at its upper end to an enlarged curved head 33. The shaft 31 extends axially along a central axis B of rotation, and can define any suitable diameter, length, and thread design so as to engage the underlying bone, such as a vertebra 27. Alternatively, the shaft 31 can be unthreaded so as to define a pin or a nail if desired. Thus, one skilled in the art will appreciate that the bone anchor 30 is not limited to any particular type of shaft 31. The bone anchor 30 may also be cannulated and fenestrated such that openings extend radially outward from a central hollow channel in a cannulated shaft to urge fluid out of the bone anchor 30 during injection or draw fluid into the central hollow channel from the radial sides of the anchor during extraction of material adjacent the anchor if desired.

The bone anchor 30 further includes a vertically extending neck 35 connected between the shaft 31 and the head 33. The neck 35 is illustrated as extending axially in a direction parallel to axis B, and includes an outer neck surface 37 that defines a neck diameter, which is less than the diameter of the head 33.

The head 33 can define a semi-spherical curvature, or can alternatively define any suitable curvature as desired to facilitate rotation with respect to the collet 28 as is described in more detail below. The head 33 defines a pivot location that extends along a lateral pivot axis of rotation $LA_P$ that extends through the head in a direction parallel to the lateral axis LA. The head 33 further defines a pivot location that extends along a longitudinal axis of rotation $L_P$ that extends through the head in a direction parallel to the longitudinal axis L. The head 33 also includes a drive surface 39 configured to receive a corresponding tip of a drive tool, such as a screw driver configured to rotate the bone anchor 30 into engagement with the vertebrae 27 or other underlying bone surface. The drive surface 39 can define a hexagon, a star drive pattern, a Phillips head pattern, a slot for a screw driver, threads configured to receive corresponding threads of a threaded drive post, or any suitable drive tool engaging structure as desired.

Referring now to FIG. 4A, the anchor seat 26 includes an anchor seat body 38 that can be described as a generally cylindrical tubular body extending centrally along an axial axis A that extends generally in the anterior-posterior direction in the sagittal plane when the bone fixation element is implanted in the underlying vertebra. Thus, as known by those having ordinary skill in the art, the longitudinal axis L and the axis A extend substantially in the sagittal plane when the bone fixation assembly 20 is fixed in the vertebrae 27. The body 38 includes a base 40 and a pair of spaced opposing arms 42 extending out (up in illustrated the orientation) from the base 40. The arms 42 can be substantially identically or identically constructed. The arms 42 define corresponding upper ends 46 that are also the upper ends of the body 38, and define an upper opening 48. The base 40 defines a lower end 50 that is also the lower end of the body 38, and defines a lower opening 52. The body 38 defines an axial bore 54 extending from the lower opening 52 to the upper opening 48.

The body 38 includes a pair of spaced opposing support walls 56 and a pair of spaced opposing spacer walls 58 connected between the support walls 56. The support walls 56 can be substantially identically or identically constructed, and the spacer walls 58 can likewise be substantially identically or identically constructed. The arms 42 extend up from respective support walls 56, and can be shaped as desired. As illustrated, the arms 42 are arc-shaped with the axis of the arc passing through the plane of symmetry that bisects the anchor seat 26. Each arm 42 extends circumferentially about its axis less than 180°, such as between 60° and 150°, for instance approximately 90°. In one highly preferred embodiment, each arm 42 extends circumferentially 90.5° about its axis. Accordingly, a gap G extends circumferentially between adjacent circumferentially outer ends of the arms 42. The opposing gaps G are in alignment with the axial bore 54. The arms 42 can be disposed radially opposite each other such that the gaps G, in combination with the aligned portion of the axial bore 54, define a rod-receiving channel 36 that is sized and configured to receive the fixation rod 24 such that the fixation rod 24 extends through the bone fixation element 22. Thus, the gaps G are aligned in the longitudinal direction. The fixation rod 24 can thus extend through the opposing gaps G and the axial bore 54. The arms 42 define radially inner and outer surfaces 60 and 62, respectively. The inner surfaces 60 define threads 60A, and are configured to threadedly receive the locking cap 34, as will now be described.

In particular, referring to FIGS. 5A-C, the locking cap 34 is illustrated as a set screw 64 and a saddle 66 operatively coupled to the set screw 64. The set screw 64 includes a generally cylindrical set screw body 65 having external threads 68 configured to threadedly engage the threads 62 formed on the inner surfaces 60 of the arms 42. In accordance with one embodiment, the threads 68 and 62 can incorporate inclined load flanks forming an angle with respect to the axis A of the bone fixation element 22. The load flanks may converge so that the top surface of the thread and the bottom surface of the thread converge. The angle may be between 0 degrees (0°) and 30 degrees (30°), and in one embodiment can be about five degrees (5°). One skilled in the art will appreciate that the threads may take on any alternative form as desired, including negative load threads, perpendicular threads, buttress threads, or the like.

The externally threaded set screw 64 generally provides flexibility when inserting the fixation rod 24 into the anchor seat body 38 such that the fixation rod 24 need not be completely reduced or seated within the body 38 prior to engagement of the locking cap 34. The set screw 64 is configured to be tightened within the anchor seat 26 against the fixation rod 24. The locking cap 34 may be constructed as desired for this purpose including, but not limited to, an externally threaded cap, a quarter-turn or partial-turn locking cap, a two-piece screw set, or the like.

The set screw 64 is illustrated as including a drive surface 70 provided as an internal recess extending vertically down into the upper end of the screw 64. The drive surface has any suitable shape configured to cooperate with a corresponding drive tool for threadedly securing the set screw 64 onto the anchor seat body 38. The drive surface 70 can define any shape as desired, for instance an external hexagon, a star drive pattern, a Phillips head pattern, a slot for a screw driver, a threading for a correspondingly threaded post, or the like.

With continuing reference to FIGS. 5A-C, the saddle 66 includes a saddle body 72 having a transverse recess 74 extending up into the bottom end of the saddle body 72. The recess 74 can define a round surface that extends about a longitudinally extending axis, such that the recess 74 is configured to receive the fixation rod 24 at a rod-contacting surface 76. The rod-contacting surface 76 can include a desired surface finish that adds roughness, such as, for example, a knurl, bead blasting, grooves, or other textured finish that increases surface roughness and enhances rod push through strength.

The saddle 66 can be coupled to the set screw 64 in any desired manner, including adhesion, mechanical fastening, and the like. In the illustrated embodiment, the saddle 66 includes a stem 78 extending centrally upward from the saddle body 72. The stem 78 is configured to be received in a central bore 32 extending vertically into the lower end of the set screw body 65, and can be fastened within the central bore with a rivet 80 or other like fastener. Accordingly, the saddle 66 is rotatable relative to the set screw 64, such that the saddle 66 can self-align with the fixation rod 24 as the set screw 64 is being rotated with respect to the anchor seat 26, for instance when the locking cap 34 is being tightened against the fixation rod 24.

Referring again to FIG. 4A, and as described above, the anchor seat body 38 includes a pair of spaced opposing support walls 56 and a pair of spaced opposing spacer walls 58 connected between the support walls 56. The arms 42 extend up from respective support walls 56, such that the spacer walls 58 are disposed between the arms 42. Each of the spacer walls 58 defines opposing upper ends 84 and lower ends 82 that can be shaped as desired. The upper ends 84 are round in accordance with the illustrated embodiment, such that the upper ends 84 and the circumferentially outer ends of the arms 42 are adjoined to generally define a U-shape from a horizontal view through the gaps G. Thus, the upper ends 84 define the lower end of the gaps G.

The upper ends 84 can be shaped to conform generally with the outer surface of the fixation rod 24, such that the upper ends 84 receive and engage the fixation rod 24 during use. Alternatively, the upper ends 84 can be spaced slightly below the upper surface of the collet 28, such that the collet 28 supports the fixation rod 24 during use, as will be described in more detail below.

The support walls 56 each define opposing inner and outer surfaces 86 and 88, respectively. The support walls 56 flare inward toward axis A in a downward direction from the arms 42, and terminate at respective lower ends 90. The inner surfaces 86 of each support wall 56 at the lower end 90 define a distance D therebetween that is less than the distance between opposing radially opposing inner surfaces 60 of the arms 42, and greater than the diameter of the head 33 of the bone anchor 30. The inner surfaces 86 flare radially inward toward the central axis A, and toward each other, along a downward direction, and are each connected to bottommost, and innermost, surfaces that define respective longitudinal guide walls 92.

Referring also to FIG. 4B, each guide wall 92 defines respective inner guide surfaces 93 that extend in a desired plane through which the bone anchor 30 is permitted to pivot relative to the anchor seat 26. In the illustrated embodiment, the desired plane is the sagittal plane SP. It should be appreciated in alternative embodiments that the anchor seat 26 can be constructed such that the guide walls 92 extend in any desired alternative plane, such as a plane defined by the medial-lateral and anterior-posterior directions.

Figure 7C:
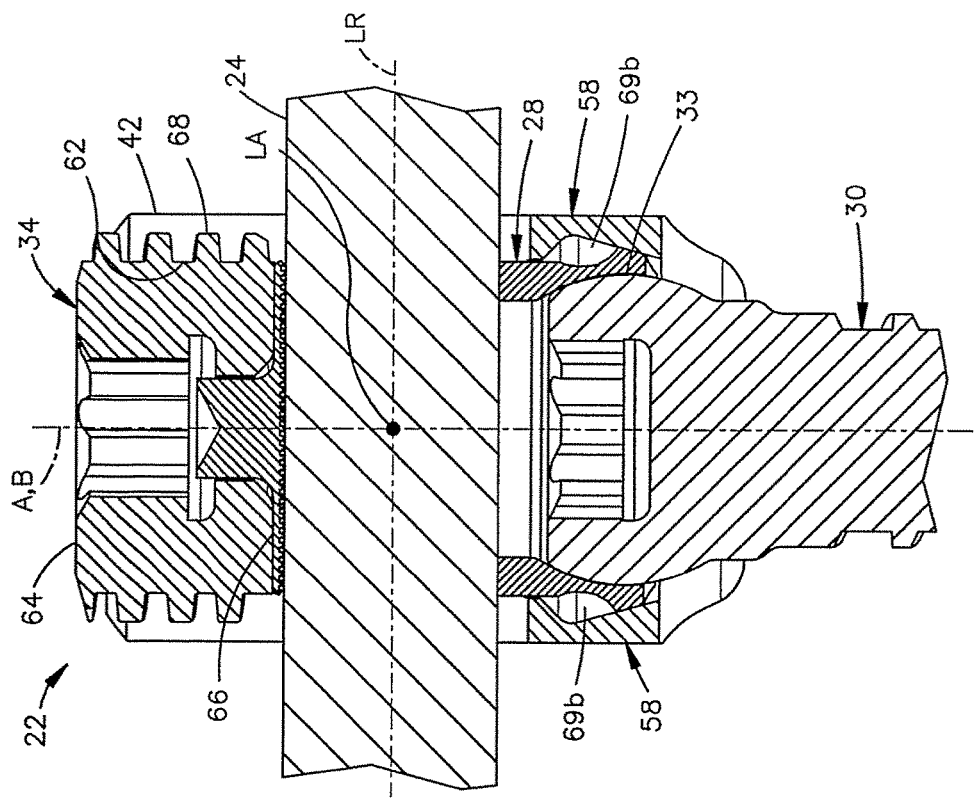
FIG. 7C is a sectional side elevation view similar to FIG. 7A, but showing the bone fixation element including a fixation rod extending through the anchor seat, and a locking cap affixed to the anchor seat.
Figure 7D:
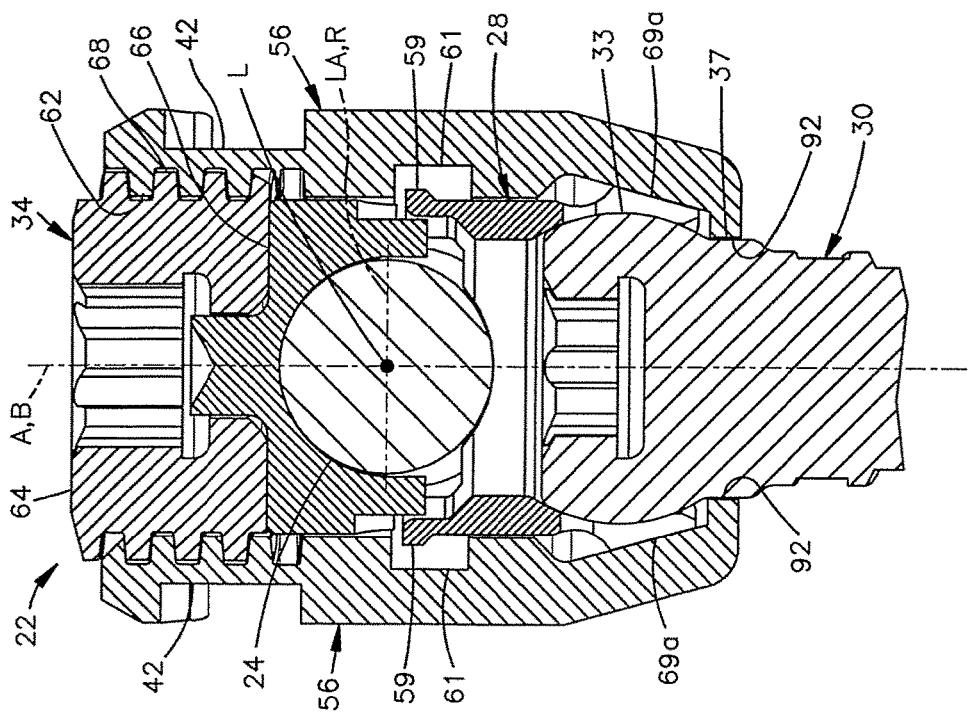
FIG. 7D is a sectional side elevation view similar to FIG. 7B, but showing the bone fixation element illustrated in FIG. 7C.
Figures 8C, 8D:
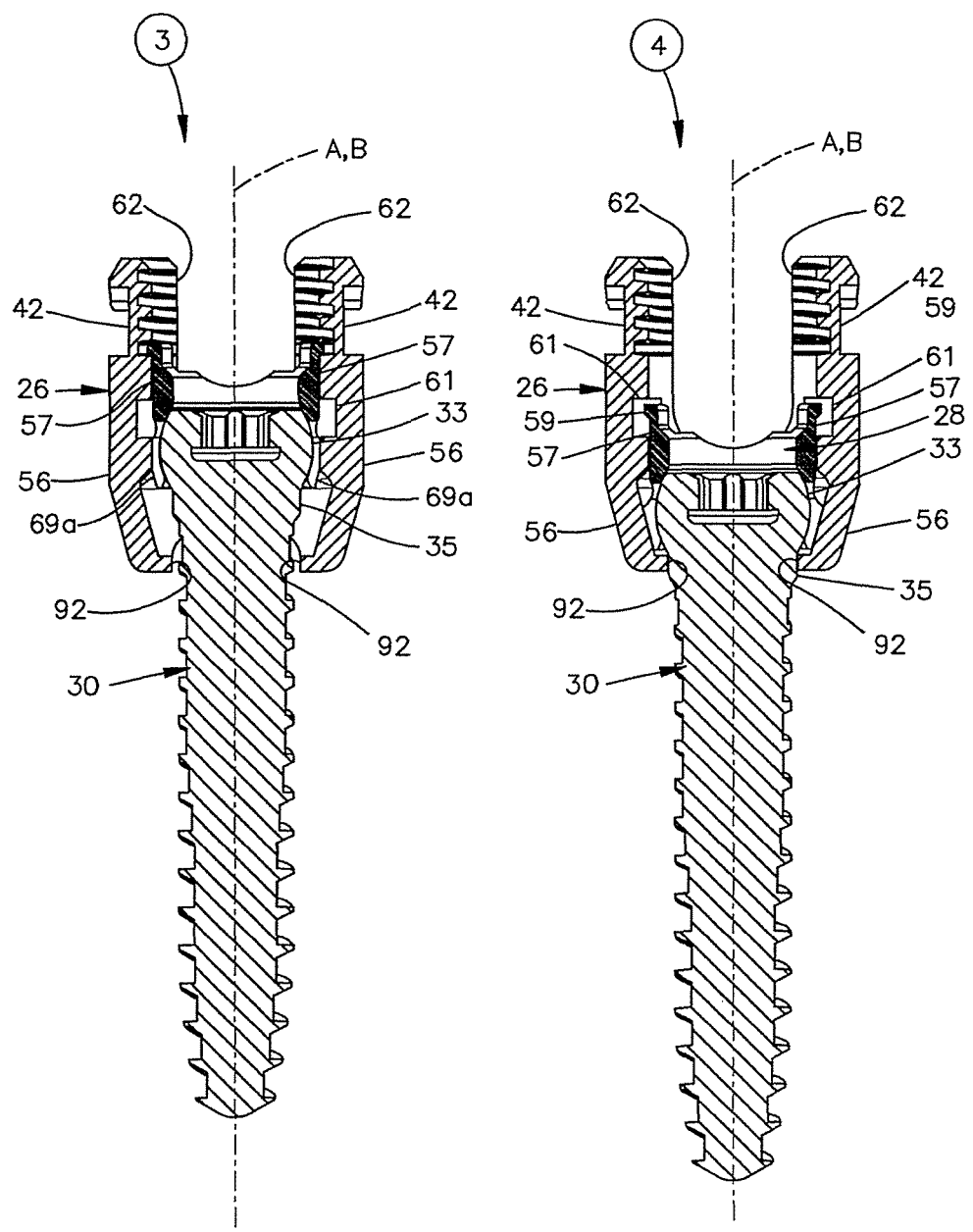
FIG. 8C is a schematic view illustrating the method for assembling the bone fixation element illustrated in FIG. 1A, and showing an upward force being applied to the bone anchor so as to insert the anchor head into the lower end of the collet.
FIG. 8D is a schematic view illustrating the method for assembling the bone fixation element illustrated in FIG. 1A, and showing a downward force being applied to the collet thereby locking the anchor and collet in the anchor seat.

Referring also to FIG. 7A, the opposing guide walls 92 define a distance therebetween that is substantially equal to the diameter of the neck 35, such that the guide walls 92 are configured to abut opposing abutment surfaces of the bone anchor, which are illustrated as opposing sides of the outer neck surface 37 when the bone anchor 30 is disposed in the anchor seat 26. The opposing sides of the outer neck surface 37 are spaced along a lateral axis that is perpendicular to the longitudinal axis L. Accordingly, the guide walls 92 prevent the bone anchor 30 from pivoting along a first direction D toward either guide wall 92 with respect to the anchor seat 26, for instance about the longitudinal pivot axis $L_P$. Thus, the guide walls 92 provide a guide or track that permits the bone anchor 30 to pivot along the guide or track only in a desired plane that is defined by the guide wall 92 (e.g., sagittal plane) and includes the axis A, and prevents the bone anchor 30 from pivoting in any other plane that 1) includes the axis A, and 2) intersects the desired plane. When the anchor 30 pivots in the desired (e.g., sagittal) plane, the axis of rotation B becomes angularly offset with respect to the central axis A of the subassembly 75.

Alternatively, the guide walls 92 can be spaced apart a distance greater than the diameter of the neck 35, but disposed within close proximity of the bone anchor 30, so as to limit pivotal movement of the bone anchor 30 relative to the anchor seat 34 in the first direction D in a plane that is perpendicular to the desired (e.g., sagittal plane), for instance about the longitudinal pivot axis L. The bone anchor 30 can pivot about the longitudinal pivot axis $L_P$ through a range of angles defined by the central anchor axis B and the central anchor seat axis A that is less than 10°, for instance less than 5°, such as 0°. The distance between the opposing guide walls 92 is less than the diameter of the head 33 of the bone anchor 30, while the inner surfaces 86 define a distance therebetween that is slightly greater than the diameter of the anchor head 33.

Referring now to FIGS. 4 and 7B, the lower ends 82 of the spacer walls 58 are connected between the outer ends of the opposing support walls 56, and extend in a direction substantially perpendicular to the guide walls and perpendicular to the longitudinal axis L. Furthermore, the lower ends 82 are upwardly displaced with respect to the guide walls 92. Accordingly, the lower ends 82 are positioned to permit the bone anchor 30 to pivot in a second direction E about the lateral pivot axis $LA_P$ along a second plane (e.g., the sagittal plane) relative to the anchor seat 26 until the neck 35 of the bone anchor 30 abuts one of the lower ends 82. In this regard, the lower ends 82 can be referred to as stops. Because the lower ends 82 are displaced above the guide walls 92, the bone anchor can pivot more in the second direction E than in the first direction D. For instance, as illustrated, the bone anchor 30 can pivot such that the central axis B of the bone anchor can be angularly offset with respect to the central axis A of the anchor seat 26 through a range of angles +/− between 0° and 90° with respect to the vertical, such as between 5° and 45°, including between 15° and 35°, for instance 25° in the sagittal plane before the neck 35 abuts the lower ends 82. The neck 35 of the anchor 30 can ride along the guide wall 92 as it pivots in the sagittal plane SP.

Figure 6:
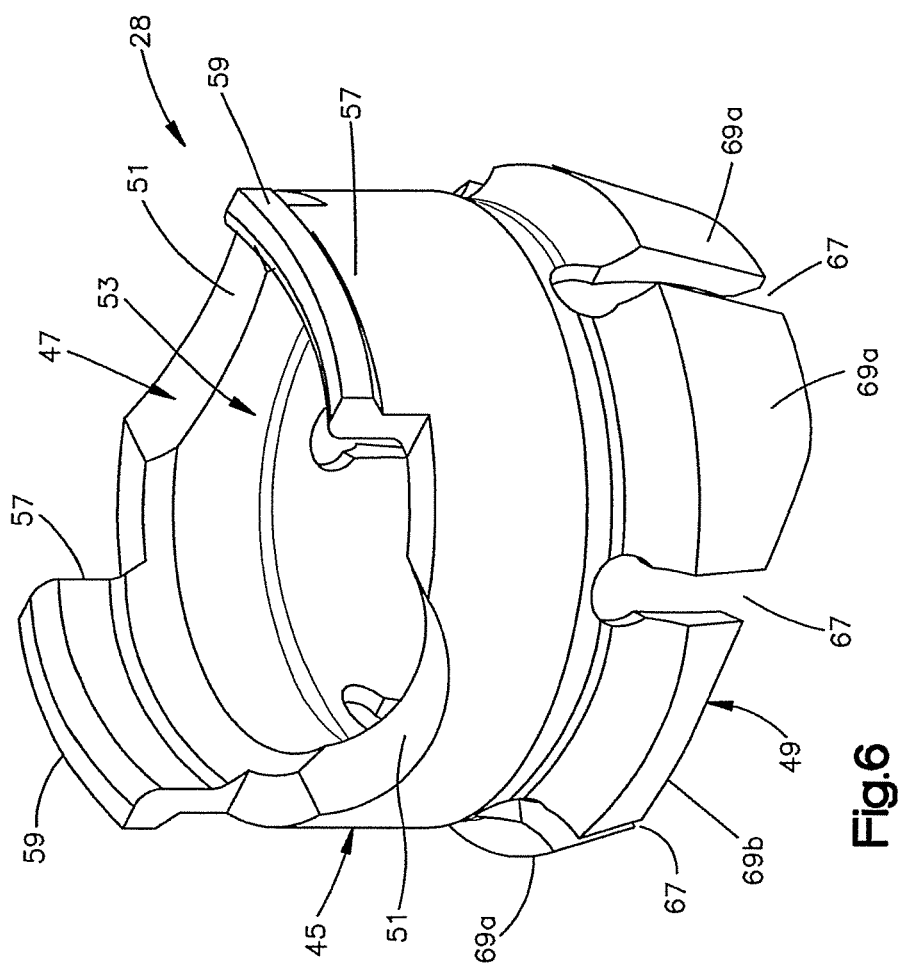
FIG. 6 is a perspective view of the collet illustrated in FIG. 1B.

Referring now to FIG. 6, the collet 28 includes a collet body 45 that defines a first or upper end 47 sized and configured to contact or support at least a portion of the fixation rod 24 when the rod is received within the rod-receiving channel 36, and a second or lower end 49 sized and configured to contact or otherwise engage, directly or indirectly, a portion of the bone anchor head 33. The collet body 45 is annular, and thus defines an axial bore 53 extending between and through the upper and lower ends 47 and 49. The axial bore 53 is aligned with the axial bore 54 when the collet 28 is installed in the anchor seat 26.

Referring to FIGS. 6 and 7A-B, the upper end 47 defines radially opposing upwardly facing seat portions 51 having a curvature or semi-spherical shape corresponding to the outer surface of the fixation rod 24, and is therefore configured to receive or otherwise support at least a portion (e.g., a lower portion) of the rod 24. The lower end 49 defines an inner surface 55 defining a curvature or semi-spherical shape corresponding to the outer surface of the anchor head 33, and is therefore configured to receive or otherwise engage at least a portion of the head 33, so that the head can rotate with respect to the collet 28 and the anchor seat 26, and can further pivot with respect to the collet 28 as permitted by the anchor seat 26. Because the bone anchor 30 can freely rotate about its axis of rotation B relative to the anchor seat 26, and thus the anchor seat 26 can likewise rotate about the bone anchor 30, the rod-receiving channel 36 can be aligned with the fixation rod 24 without advancing or withdrawing the bone anchor 30 in or out of the underlying bone. Thus, the bone anchor 30 can maintain a constant insertion depth in the underlying bone (e.g., vertebra 27) while adjusting the orientation of the rod-receiving channel 36.

The collet 28 further includes a pair of flanges 57 extending up from the upper end 47 of the collet body 45 at a location radially between the seat portions 51. A locking lip 59 extends radially out from each flange 57. As best shown in FIG. 7A, the anchor seat 26 defines a pair of opposing recesses 61 formed radially in the opposing inner surfaces 86 of the support walls 56 at a location below the threaded inner surfaces 60 of the arms 42. During operation, the collet 28 can be inserted down into the anchor seat 26, thereby causing the flanges 57 to flex inwardly past the threaded inner surfaces 60, until the lips 59 clear the upper ends 63 of the recesses 61, at which point the flanges 57 snap back out so that the lips 59 are disposed in the recesses 61. Interference between the lips 59 and the upper ends 63 prevent the collet 28 from backing out through the upper end of the anchor seat 26. The recesses 61 further define a circumferential length substantially equal to that of the flanges 57 and locking lips 59, such that the collet 28 is rotationally fixed with respect to the anchor seat 26 in a position whereby the upper surface 47 is aligned with the fixation rod 24 when the fixation rod 24 is inserted into the anchor seat 26.

The lower end 49 of the collet 28 defines an outer diameter that is greater than the inner distance between the guide walls 92. Accordingly, the collet 28 is unable to pass axially down through the lower end of the anchor body 26. The lower end 49 includes one or more slots 67 (illustrated as a plurality of slots) extending radially therethrough so as to define opposing pluralities of fingers 69A and 69B. When the collet 28 is disposed in the anchor seat 26 such that the lips 59 are disposed in the respective recesses 61, the fingers 69A are axially aligned with the guide walls 92, and the fingers 69B are axially aligned with the lower ends 82 of the spacer walls 58. Thus, as shown in FIGS. 7A-B, when the collet 28 and anchor 30 are installed in the anchor seat 26, the fingers 69A and 69B radially expand to conform with the outer surface of the anchor head 33 and the inner surfaces of the support walls 56 and spacer walls 58, respectively, as illustrated in FIGS. 7A-B. The inner diameters defined by the opposing fingers 69A and 69B are less than the outer diameter of the anchor head 33 to prevent the anchor 30 from being removed from the anchor seat 26 in an axially downward direction.

The lower ends of the fingers 69A terminate at a location above the guide walls 92, and the lower ends of the fingers 69B terminate at a location above the lower ends 82. Accordingly, the fingers 69A and 69B do not interfere with the engagement between the anchor neck 35 and the guide walls 92 and lower ends 82, and thus do not interfere with the permissible movement of the bone anchors 30 relative to the anchor seat 26. Alternatively, one or both of the pluralities of fingers 69A-B could extend below the anchor seat 26, and thus abut the anchor 30 in the manner described above with respect to the guide 92 and stop surface 82 so as to direct movement of the bone anchor 30 in a desired direction (e.g., pivot in the sagittal plane).

Referring now to FIGS. 8A-8D, a method for assembling a bone fixation subassembly 75 includes at step 1, inserting the bone anchor 30 vertically down through the axial bore 54, such that the shaft 31 extends through the lower opening 52 of the lower end 50 of the anchor seat 26. Next, at step 2, the collet 28 is inserted into the axial bore 54 to a location whereby the locking lips 59 can engage the lowermost threads 62 of the inner surface 60 of the arms 42. Next, at step 3, an upward force can be applied to the bone anchor 30 so as to insert the anchor head 33 into the lower end 49 of the collet 28. The locking lips 59 of the collet 28 brace against the anchor seat 26 inside the threads 62 to prevent the upward force applied by the screw 28 from causing the collet 28 to back out of the upper opening of the anchor seat 26. At step 4, a downward force is applied to the collet 28, thereby inserting the locking lips 59 into the recesses 61 in the manner described above, and locking the anchor 30 and collet 28 in the anchor seat 26.

It should thus be appreciated that the subassembly 75 can include the collet 28 installed in the anchor seat 26, and the bone anchor 30 installed in the collet 28. In alternative embodiments, a subassembly can be provided include the collet installed in the anchor seat without a bone anchor installed in the collet. In these embodiments, the bone anchor can be implanted into underlying bone before the anchor head is inserted into the collet. The anchor 30 can comprise a pin or nail, or a screw as desired. It should be appreciated that the bone fixation subassembly 75 and the alternative bone fixation subassemblies described herein can likewise be referred to as spine fixation subassemblies when, for instance, they are configured for implantation into one or more vertebrae for vertebral fixation.

During use, because the bone anchor 30 is rotatable with respect to the collet 28 and the anchor seat 26, a driving tool can engage the drive surface 39 of the head 33 so as to insert the threaded shaft 31 into the underlying bone, as shown in FIG. 1A. Next, as shown in FIGS. 7A-D, the anchor seat 26 can be rotated about axis A in the direction of Arrow R about the full 360° range of angles so as to align the rod-receiving channel 36 with the longitudinal axis of the fixation rod 24. Once the bone anchor 30 has reached a desired depth in the underlying vertebra, the fixation rod 24 can be inserted into the subassembly 75. In particular, the fixation rod 24 is inserted into the axial bore 54 either horizontally through the gaps G, or vertically down into the axial bore 54. It should be appreciated that the fixation rod 24 will be seated in the upper end 47 of the collet 28.

With continuing reference to FIGS. 7A-D, once the rod 24 is installed in the subassembly 75, the locking cap 34 can be attached to the subassembly 75 so as to fully assembly the anchor assembly 22. In this regard, it should be appreciated that the subassembly 75 can further include the fixation rod 24 and/or the locking cap 34. In the illustrated embodiment, the external threads 68 of the set screw 64 are rotated within the inner threads 62 of the anchor seat arms 42, thereby causing the set screw and saddle 66 to move axially down in the axial bore 54. As the saddle 66 approaches the fixation rod 24, the saddle 66 is rotated with respect to the set screw 64 so as to bring the rod-contacting surface 76 into alignment with the fixation rod 24. Once the saddle 66 is aligned with the fixation rod 24, the set screw 64 is continuously threadedly inserted into the bone anchor 26, such that the locking cap 34 can be tightened against the rod 24, thereby applying a downward axial force to the rod 24. The locking cap 34 can be said to be in an initial position when installed in the locking cap 34 but before applying an axial force against the fixation rod 24. The axial force applied to the rod 24 by the locking cap 34 is transmitted to the collet 28, which causes the fingers 69A to ride along the inner surfaces 86 of the support wall 56, and fingers 69B to ride along the radially inner surfaces of the spacer walls 58.

As the fingers 69A ride along the inner surfaces 86, they become radially inwardly displaced due to the inward flare of the inner surfaces 86, thereby radially biasing, or radially compressing, the fingers 69A against the anchor head 33. Likewise, as the fingers 69B ride axially down along the radially inner surfaces of the spacer walls 58, the fingers 69B become disposed between the anchor head 33 and the spacer walls 58, thereby radially compressing the fingers 69B against the anchor head 33. Increasing radial compression of the fingers 69A-B against the anchor head 33 causes frictional forces between the fingers 69A-B and the anchor head 33 that resist both rotation of the anchor 30 about the axis A relative to the anchor seat 26, collet 28, and fixation rod 24, and also resist pivoting of the anchor, for instance in the sagittal plane. When the locking cap is fully tightened to a locked position, the resulting frictional forces prevent the anchor 30 from movement relative to the anchor seat 26, collet 28, and fixation rod 24. Thus, the locking cap 34 is configured to transmit a locking force onto the collet 28 and bone anchor 30 to fix or lock the position of the bone anchor 30 relative to the anchor seat 26 and fixation rod 24. Furthermore, when the locking cap 34 is in the locked position, the fixation rod 24 is captured between the saddle 66 and the upper surface of the collet 28 such that the anchor seat 26 is prevented from movement relative to the fixation rod 24.

It should be appreciated that any time after the bone anchor 30 installed in the anchor seat 26 and before the bone anchor 30 is locked in place, the bone anchor 30 can be pivoted in the sagittal plane SP about the lateral pivot axis $LA_P$ in the manner described above, while the bone anchor 30 is prevented from pivoting in all other planes. Because the guide walls 92 prevent the bone anchor 30 from pivoting about an axis that is angularly offset with respect to the lateral pivot axis $LA_P$ in the illustrated embodiment, the surgeon is assured that the anchor 30 can only pivot in the sagittal plane SP, and will not cause the vertebrae 27 to become misaligned due to movement of the bone anchor 30 in a direction other than in the sagittal plane. Accordingly, the bone fixation assembly 20 incorporating the bone fixation elements 22 has particular utility in addressing spinal misalignments such as the rotational component of a scoliosis deformity.

In one particular method, the locking cap 34 can be tightened against the rod to an intermediate position that sufficiently radially compresses the fingers 69A-B against the bone anchor 30 that prevents the bone anchor 30 from freely pivoting in the sagittal plane, for instance under gravitational forces, while allowing a surgeon to pivotally adjust the angular position of the bone anchor 30 in from an initial position in a desired plane to a desired position in the desired plane by applying a force to the bone anchor 30 that overcomes the friction between the bone anchor 30 and the fingers 69A-B. In the illustrated embodiment, the desired plane is the sagittal plane Once the bone anchor 30 is in the desired angular position in the sagittal plane, the locking cap 34 can be further tightened to a locked position whereby the bone anchor 30 is locked in place in the desired angular position in the desired plane. It should be appreciated that the end cap 34 can be unthreaded from the locked position into the intermediate position or the initial position if it is desired to further adjust the angular position of the bone anchor 30.

It should be appreciated that the above-described method steps can be performed for each bone fixation element of the bone fixation assembly 20 as desired. Furthermore, the method steps described above need not be performed in the order described, and it should be appreciated that that one or more of the steps can be omitted if desired. It should be further appreciated that while the guide walls 92 prevent the bone anchor 30 from pivoting in a first plane that intersects the sagittal plane relative to the anchor seat 26 and fixation rod 24, the guide walls 92 could alternatively be slightly spaced with respect to the neck 35, such that the anchor 30 can pivot about a first plane that intersects the second sagittal plane within an angular range that is less than the angular range that the anchor 30 can pivot in the sagittal plane.

Referring to FIGS. 1-8 generally, one or more bone fixation assemblies 20 can be provided as one or more bone fixation elements 22 provided as a bone fixation kit. The kit can include at least one of the following components: one or more bone anchors 30, one or more locking caps 34, one or more collets 28, one or more fixation rods 24, one or more anchor seats 26, and/or one or more preassembled bone fixation subassemblies 75, including a bone anchor 30 and collet 28 pre-installed in the anchor seat 26 in the manner described above. Thus, the surgeon can implant the bone anchor 30 of a plurality of subassemblies in an underlying bone, such as a vertebra, and the anchor seats of the subassemblies can be coupled to a fixation rod 24 in the manner described above. It should further be appreciated that the components included in the kit may vary by at least one characteristic. For example, the components included in the kit can vary in size and shape, and/or they can be constructed in accordance with alternative embodiments as described herein, or they could be identically constructed with the same size and shape. For instance, fixation rods 24 and bone anchors 30 can be provided having different diameters and lengths, and the bone anchors 30 can be provided as screws and nails or pins. Alternatively, several kits can be provided, each individual kit including components corresponding to a particular size, and shape, and embodiment, wherein the size, shape, and/or embodiment of the components of the kits can vary from kit to kit.

While the bone fixation element 22 has been illustrated and described in accordance with one embodiment, it should be appreciated that bone fixation elements, a bone fixation assembly incorporating the bone fixation elements, and bone fixation kits can be constructed in accordance with several alternative embodiments.

For instance, referring to FIGS. 9-10, a bone fixation subassembly 175 constructed in accordance with an alternative embodiment is illustrated including reference numerals corresponding to like elements of the bone fixation subassembly 75 incremented by 100. Thus, the bone fixation subassembly 175 can be constructed as described with respect to the bone fixation subassembly 75 except as otherwise noted. It should be appreciated that one or more up to all of the bone fixation elements of the bone fixation assembly 20 can include the bone fixation elements 22 or alternative bone fixation elements as described herein, one or more of which can include the bone fixation subassembly 75, the bone fixation subassembly 175, or any alternative bone fixation subassembly as described herein.

The bone fixation subassembly 175 includes an anchor seat 126, and a collet 128 preinstalled in the anchor seat 126. The subassembly 175 can further include a bone anchor 30 preinstalled in the collet 128, which in turn is preinstalled in the anchor seat 126. Alternatively, the subassembly 175 can include the collet 128 preinstalled in the anchor seat 126, and the bone anchor 30 can be later installed as desired.

The anchor seat 126 includes an anchor seat body 138 extending centrally along the central axis A. The body 138 includes a base 140 and a pair of spaced opposing arms 142 extending up from the base 140. The base 140 defines a lower end 150 that is also the lower end of the body 138, and defines a lower opening 152. The body 138 defines an axial bore 154 extending from the lower opening 152 to the upper opening 148.

The arms 142 extend up from respective support walls 156, and the opposing spacer walls 158 are connected between the support walls 156. The arms 142 define internal threads 162 that are configured to engage the external threads 68 of the locking cap 34 as described above. The arms 142 further define gaps G therebetween that are configured to receive the fixation rod 24 as described above. The support walls 156 flare radially inward toward axis A in a downward direction from the arms 142 toward the lower end 150. The lower ends 150, in combination with the collet 128, limit pivotal movement of the bone anchor 30 to a single plane, such as the sagittal plane, as described above. The bone anchor 30 can also rotate about its central axial axis B relative to the collet 128 and anchor seat 126 in the manner described above.

The collet 128 includes a collet body 145 that defines a first or upper end 147 sized and configured to contact or support at least a portion of the fixation rod 24 when the rod is received within the rod-receiving channel 136, and a second or lower end 149 sized and configured to contact or otherwise engage, directly or indirectly, a portion of the bone anchor head 33. The upper and lower ends 147 and 149 are constructed as described above, except the collet body 145 includes a finger extension 173 defining the bottom end of each of the fingers 169A.

Accordingly, when the collet 128 is installed in the anchor seat 126 to provide the preassembled bone fixation subassembly 175, the finger extensions 173 extend through the lower opening 152 of the base 140. The fingers 169A and finger extensions 173 define inner surfaces 155 that in combination define a curvature or semi-spherical shape corresponding to the outer surface of the anchor head 33, and is therefore configured to receive or otherwise engage at least a portion of the head 33. The lower ends of the fingers 169B terminate at a location displaced above the lower ends of the extensions 173, and are disposed above the lower opening 152 of the base 140 when the collet 128 is installed in the anchor seat 126.

The bone fixation subassembly 175 is constructed by inserting the collet 128 down through the top of the anchor seat 126 until the locking lips 59 extend in the corresponding recesses 161. The fingers 169A and extensions 173, along with the fingers 169B, are placed over the head 33 of the bone anchor 30, and a downward force is applied until the fingers 169A-B and extensions 173 expand radially outward to capture the head 33 of the bone anchor 30 therein. The threaded shaft 31 of the bone anchor 30 may already be implanted into bone prior to popping the collet 128 over the head 33 of the bone anchor 30. It should be appreciated that the diameter of the anchor shaft 31 is not limited by the diameter of the opening 152 of the base 140. Thus, the diameter of the anchor shaft 31 can be greater than the opening 152 of the base 140. Alternatively, the diameter of the anchor shaft 31 can be smaller than that of the opening 152, such that the bone anchor 30 can be inserted down through the upper opening of the anchor seat 126 and installed in the collet 128 in the manner described above with respect to the bone fixation element 22.

The radially inner ends of the lower ends of the finger extensions 173 define guide walls 192 that are spaced apart a distance substantially equal to the cross-sectional dimension of the anchor neck 35. The guide walls 192 therefore abut the neck 35 when the head 33 is captured in the collet 128. Accordingly, the guide walls 192 permit the anchor 33 to pivot only in a desired plane that is parallel to the guide walls 192, or about the lateral pivot axis $LA_P$ (e.g., the sagittal plane). The permitted angulation in the sagittal plane is limited by contact between the neck 35 and the lower ends of the spacer walls 158 in the manner described above with respect to the bone fixation element 22. Once the bone anchor 30 has been installed in the subassembly 175, the bone anchor 30 is free to rotate with respect to the collet 128 and the anchor seat 126 about the central axis B as described above, which can be coincident with the central axis A of the anchor seat 126, or angularly offset in the sagittal plane. Once the gaps G are aligned with the longitudinal axis L of the fixation rod 24, the fixation rod 24 and locking cap 34 can be installed in the subassembly 175 in the manner described above.

Figure 11C:
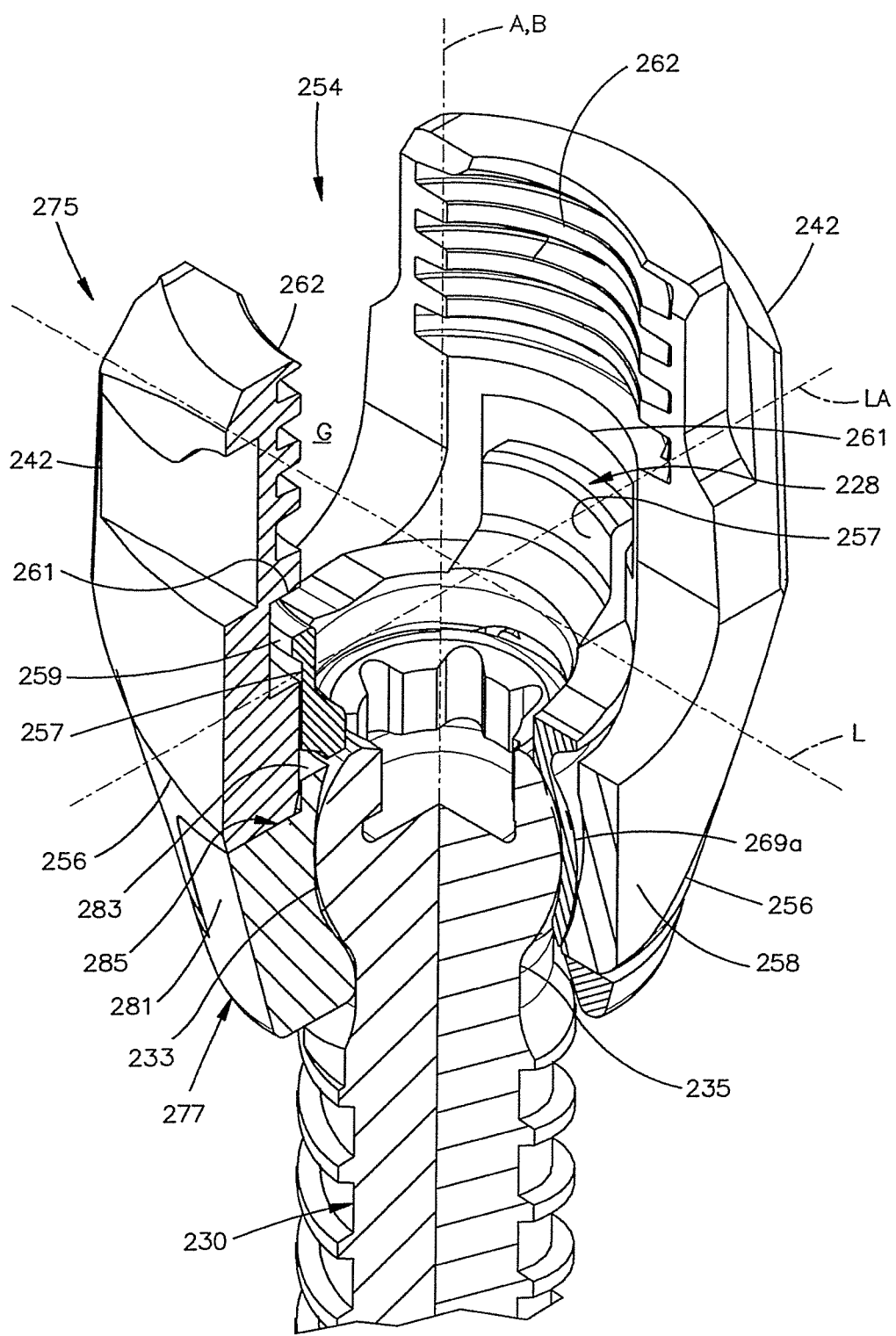
FIG. 11C is a perspective view of the bone fixation subassembly illustrated in FIG. 11A, with a potion cut away.
Figure 16A:
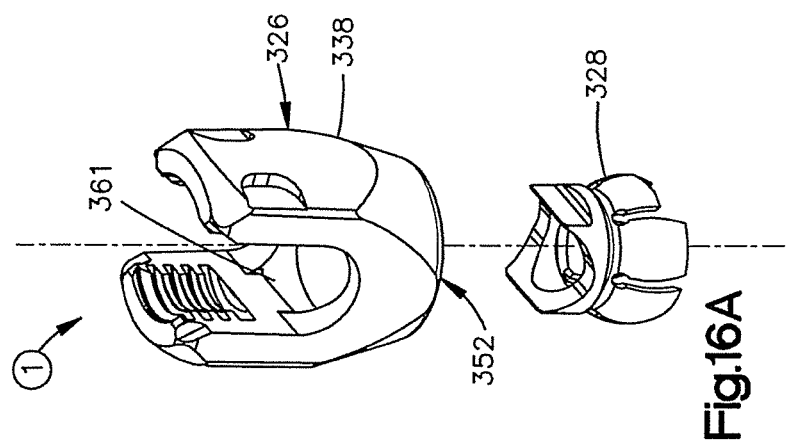
FIG. 16A is a schematic view illustrating a method for assembling the bone fixation subassembly illustrated in FIGS. 14A-B.

Referring now to FIGS. 11-13, a bone fixation subassembly 275 constructed in accordance with an alternative embodiment is illustrated including reference numerals corresponding to like elements of the bone fixation subassembly 75 incremented by 200. Thus, the bone fixation subassembly 275 can be constructed as described above with respect to one or both of the bone fixation subassemblies except as otherwise described. It should be appreciated that one or more up to all of the bone fixation elements of the bone fixation assembly 20 can include the bone fixation elements 22 or alternative bone fixation elements as described herein, one or more of which can include the bone fixation subassembly 275 as will now be described.

The bone fixation subassembly 275 includes an anchor seat 226, and a collet 228 preinstalled in the anchor seat 226. The subassembly 275 can further include a bone anchor 230 preinstalled in the collet 228, which in turn is preinstalled in the anchor seat 226. Alternatively, the subassembly can include the collet 228 preinstalled in the anchor seat 226, such that the bone anchor 230 can be later installed as desired. For instance, the bone anchor 230 can be installed into the subassembly 275 interoperatively (e.g., after the bone anchor 630 has been affixed in a vertebrae).

The anchor seat 226 includes an anchor seat body 238 extending centrally along the central axis A. The body 238 includes a base 240 and a pair of spaced opposing arms 242 extending up from the base 240. The base 240 defines a lower end 250 that is also the lower end of the body 238, and defines a lower opening 252. The body 238 defines an axial bore 254 extending from the lower opening 252 to the upper opening 248. The arms 242 extend up from respective support walls 256, and the opposing spacer walls 258 are connected between the support walls 256. The arms 242 define internal threads 262 that are configured to engage the external threads 68 of the locking cap 34 as described above. The arms 242 further define gaps G therebetween that are configured to receive the fixation rod 24 as described above.

The anchor seat 226 includes an anchor seat extension 277 that is separate from the anchor seat body 238. The extension 277 is configured to fasten to the bone anchor 230 prior to attaching the bone anchor 230 to the collet 228. As will be appreciated below, the extension 277 is provided as a clip that can be snapped onto the neck 235 of the bone anchor 230. The anchor seat extension 277 includes a circumferentially extending collar 279 and a pair of opposing posts 281 extending out (or vertically up, in the illustrated embodiment, from the collar 279. The collar 279 extends circumferentially greater than 180° but less than 360°, and defines an inner diameter substantially equal to the outer diameter of the anchor neck 237. A pair of tabs 283 extend up from the radially inner ends of the posts 281.

The anchor seat body 238 includes a recess 285 extending in the support walls 256 and one of the spacer walls 258 sized to receive the anchor seat extension 277. The recess 285 is keyed to receive the posts 281 in the support walls 256, such that the circumferential collar extends along one longitudinal end of the collar body but not the other longitudinal end. The outer diameter of the anchor seat extension 277 is substantially equal to the outer diameter of the lower end 250 of the anchor seat body 238, such that the outer circumferential surface of the extension 277 is flush with the outer circumferential surface of the anchor seat body 238 when the extension 277 is disposed in the recess 285. The outer diameter defined by the tabs 283 is substantially equal to the inner diameter of the support walls 256.

As shown in FIGS. 13A-13C, the subassembly 275 is constructed at step 1A by installing the collet 228 in the anchor seat 226 in the manner described above. Separately, at step 1B, the anchor seat extension 277 is attached to the bone anchor 230 by clipping the collar 279 over the anchor neck 235. Next, at step 2, the anchor body 238 is brought down onto the anchor head 233, which causes the anchor seat extension 277 to be inserted into the recess 285. The recess 285 is keyed such that the extension posts 281 are aligned with the arms 242. As the anchor body 238 is brought down onto the anchor head 233, the collet fingers 169B radially expand over the anchor head 233, and pop onto the head 233. The collet fingers 169B are disposed circumferentially between the extension posts 281, and the collet fingers 169A are shorter than the fingers 169B as shown in FIGS. 12A-B.

In one embodiment, the subassembly 275 is constructed after the completion of step 1A, and the bone anchor 230 and anchor extension 277 can be installed into the subassembly 275 at a later time, for instance before or after the bone anchor 230 has been implanted in a bone, such as a vertebra. In another embodiment, the subassembly 275 is constructed after the completion of step 2, whereby the bone anchor 230 is attached to the collet 228. It should further be appreciated that step 1A can be completed prior to step 1B or that step 1B can be completed prior to step 1A.

Once the bone anchor 230 has been installed in the anchor seat 226, the anchor 230 is free to rotate relative to the anchor seat 226 about the axis of rotation B in the manner described above. The bottom surface of the posts 281 abut the neck 233, and therefore provide a laterally spaced guide members, or a laterally extending guide, 292 that allows the anchor 230 to pivot in the sagittal plane, while preventing the anchor 230 from pivoting in any other angle that intersects the sagittal plane. When the anchor 230 pivots in the sagittal plane, the axis of rotation B is angularly offset with respect to the central axis A of the subassembly 275. The extension 277 does not extend entirely around the anchor neck 235, and thus defines a gap that is disposed on one longitudinal side of the anchor 230. Thus, the anchor 230 is free to pivot toward that longitudinal side in the sagittal plane until the anchor 230 abuts the lower end of the respective spacer wall 238, which provides a stop for the anchor 230. The collar 279 extends along the opposing longitudinal side of the anchor 230, and can be vertically flush with or above the bottom surface of the corresponding spacer wall 238 such that the spacer wall provides a stop with respect to angular movement of the anchor 230 in the sagittal plane. Alternatively, the collar 279 could be disposed below the bottom surface of the corresponding spacer wall 238 such that the collar 279 provides a stop with respect to angular movement of the anchor 230 in the sagittal plane. Thus, the collar 279 can limit pivotal movement in one direction in the pivotal plane. Alternatively still, the radially inner surface of the collar 279 could be radially outwardly displaced with respect to the radial inner surface of the posts 281, such that the collar 279 does not abut the neck 235 and thus permits pivotal movement in the sagittal plane toward the collar 279.

The collar 279 can be disposed at the inferior end of the anchor seat 226 when the bone fixation element is implanted, such that the anchor 230 can pivot along a greater angular range toward the superior end in the sagittal plane than toward the inferior end. Alternatively, the collar 279 can be disposed at the superior end of the anchor seat 226 when the bone fixation element is implanted, such that the anchor 230 can pivot along a greater angular range toward the superior end in the sagittal plane than toward the inferior end.

Once the anchor seat 226 has been aligned with the fixation rod 24, and the position of the bone anchor has been located in the sagittal plane as desired, the locking cap 34 can be locked in the subassembly 275 in the manner described above.

Figure 15:
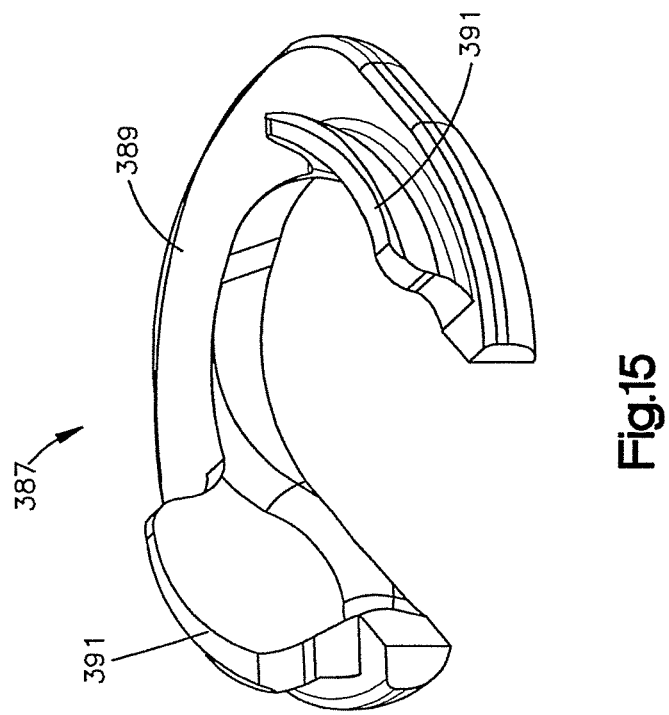
FIG. 15 is a perspective view of the collet extension illustrated in FIG. 14A.
Figure 16D:
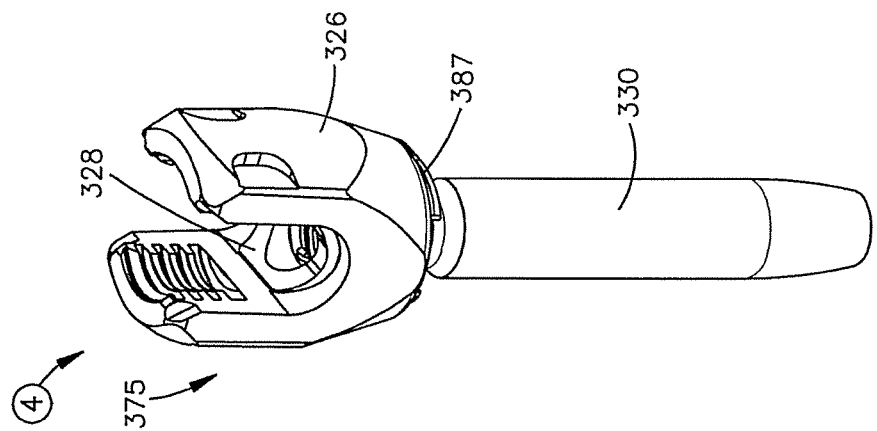
FIG. 16D is a schematic view illustrating a method for assembling the bone fixation subassembly illustrated in FIGS. 14A-B, and showing the bone anchor and collet extension attached to the anchor seat and collet.
Figure 16C:
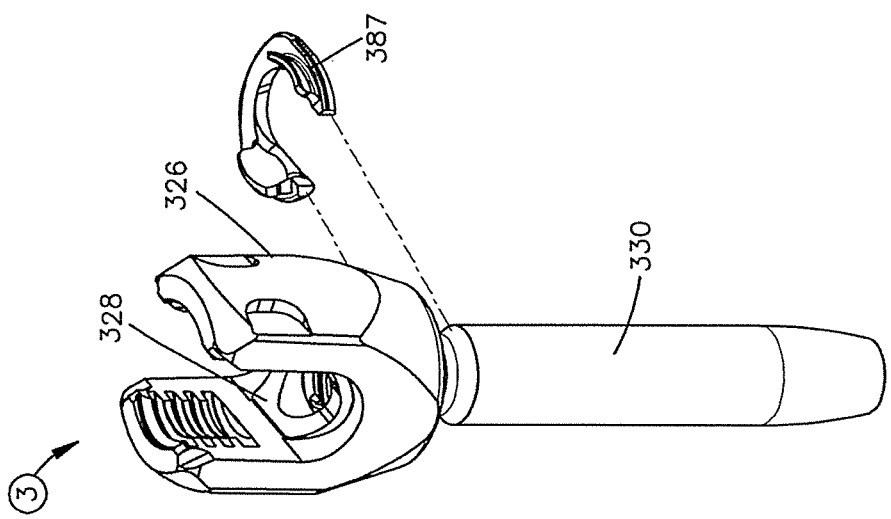
FIG. 16C is a schematic view illustrating the method for assembling the bone fixation subassembly illustrated in FIGS. 14A-B, and showing the collet extension being clipped onto the bone anchor.
Figure 16B:
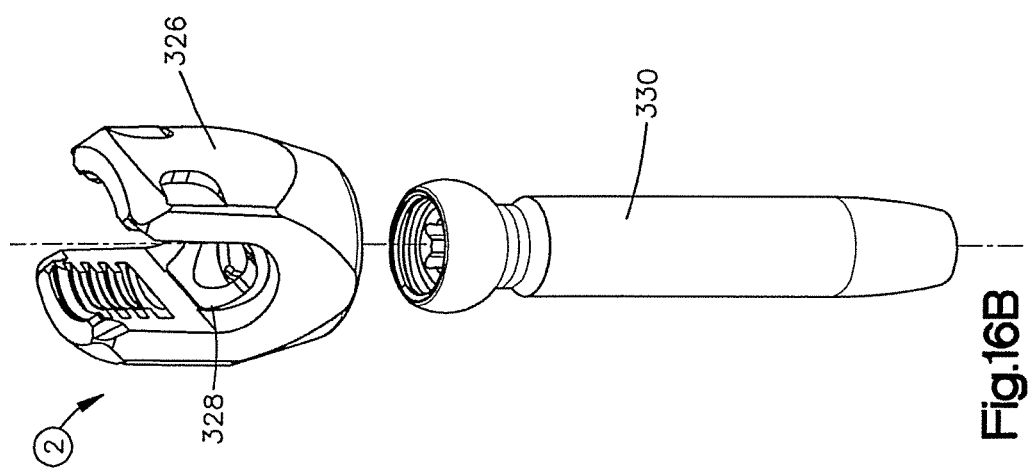
FIG. 16B is a schematic view illustrating the method for assembling the bone fixation subassembly illustrated in FIGS. 14A-B.
Figure 17:
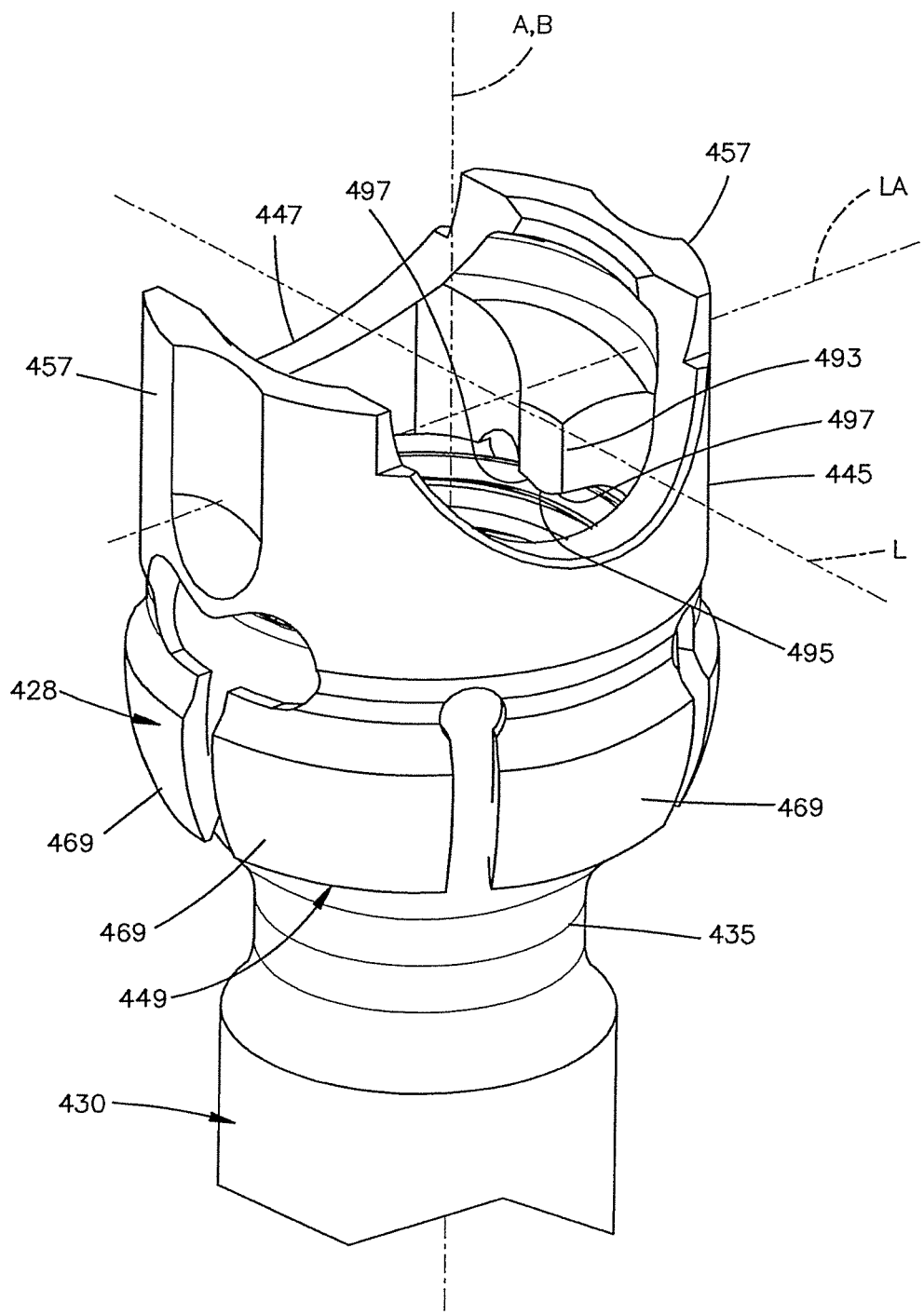
FIG. 17 is a perspective view of a bone anchor installed in a collet in accordance with another alternative embodiment.
Figure 18:
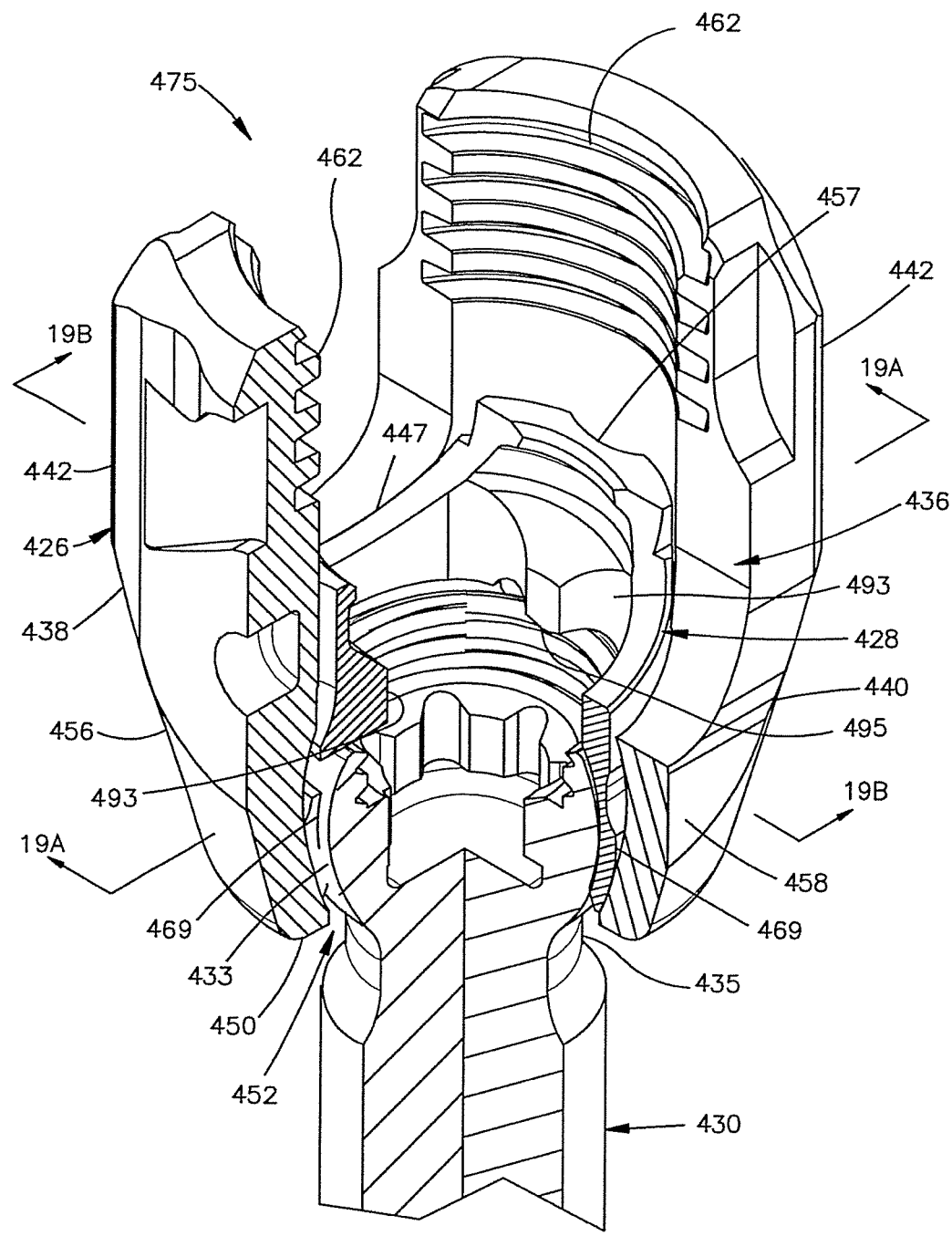
FIG. 18 is a perspective view a bone fixation subassembly constructed in accordance with another embodiment, including the anchor and collet of FIG. 17 installed in an anchor seat, with a portion cut away.

Referring now to FIGS. 14-16, a bone fixation subassembly 375 constructed in accordance with an alternative embodiment is illustrated including reference numerals corresponding to like elements of the bone fixation subassembly 75 incremented by 300. Thus, the bone fixation subassembly 375 can be constructed as described with respect to one or all of the bone fixation subassemblies described above, except as otherwise noted. It should be appreciated that one or more up to all of the bone fixation elements of the bone fixation assembly 20 can include the bone fixation elements 22 or alternative bone fixation elements as described herein, one or more of which can include the bone fixation subassembly 375 as will now be described.

The bone fixation subassembly 375 includes an anchor seat 326, and a collet 328 preinstalled in the anchor seat 326. The subassembly 375 can further include a bone anchor 330 preinstalled in the collet 328, which in turn is preinstalled in the anchor seat 326. Alternatively, the subassembly 375 be provided with the collet 328 preinstalled in the anchor seat 326, such that the bone anchor 330 can be later installed as desired.

The anchor seat 326 includes an anchor seat body 338 extending centrally along the central axis A. The body 338 includes a base 340 and a pair of spaced opposing arms 342 extending up from the base 340. The base 340 defines a lower end 350 that is also the lower end of the body 338, and defines a lower opening 352. The body 338 defines an axial bore 354 extending from the lower opening 352 to the upper opening 348. The arms 342 extend up from respective support walls 356, and the opposing spacer walls 358 are connected between the support walls 356. The arms 342 define gaps G therebetween that are configured to receive the fixation rod 24 as described above. The arms 342 further define internal threads 362 that are configured to engage the external threads 68 of the locking cap 34 as described above.

The collet 328 includes a collet extension 387 that is separate from the collet body 345. The extension 387 is configured to fasten to the bone anchor 330 after the bone anchor 330 has been attached to the collet 328. As will be appreciated below, the extension 387 is provided as a clip that can be snapped onto the neck 335 of the bone anchor 330. While the bone anchor 330 is illustrated as a nail or a pin, it should be appreciated that the anchor 330 could alternatively comprise a screw. The collet extension 387 includes a circumferential collar 389 and a pair of opposing posts 391 extending out (or vertically up in the illustrated orientation) from the collar 389. The posts 391 also flare radially outward along a vertically upward direction of travel. The collar 389 extends circumferentially greater than 180° but less than 360°, defines an inner diameter substantially equal to the inner diameter of the collet body 345, and an outer diameter substantially equal to the outer diameter of the collet body 345.

The collet body 345 is keyed to receive the collet extension 387 in a predetermined orientation. In particular, the fingers 369A that are aligned with the arms 342 are shorter than the remaining fingers 369B. Accordingly, the collet extension 387 can be inserted into the anchor seat 326 such that the posts 391 are circumferentially aligned with, and located between, the fingers 369B. The circumferential collar extends along one longitudinal end of the collar body but not the other longitudinal end.

The subassembly 375 is constructed using a method that begins at step 1) wherein the collet 328 is installed in the anchor seat 326 by inserting the collet 328 vertically upward into the lower opening 352 of the anchor seat body 338, in the manner described above. In one embodiment, the kit can include the subassembly 375 as including the anchor seat 326 and the installed collet 328. Next, at step 2, the anchor body 338 is brought down onto the anchor head 333 (or the anchor head 333 is brought up into the anchor body 338), thereby causing the collet fingers 169A-B to expand radially over the head 333 and snap down over the head 333 to secure the anchor therein. At step 3, the collet extension 387 is clipped around the neck 335, such that the posts 391 extend into a gap between the lower ends of adjacent fingers 369A. Thus, the collet body 345 is keyed such that the posts 391 are vertically aligned with the arms 342. The subassembly 375 is thus provided at step 4.

Thus, FIGS. 16A-16D illustrates the subassembly as including the anchor seat 326 and the collet 328 installed in the anchor seat 326, the collet extension 387 clipped onto the bone anchor 330, and the bone anchor 330 and collet extension 387 attached to the anchor seat 326 and collet 328. In an alternative embodiment, the subassembly 375 can include the anchor seat and the collet 328 without the anchor 330 and extension 387 installed. The anchor 330 can be implanted into the underlying bone (e.g., vertebra) before or after the collet extension 387 is clipped onto the neck, and prior to or after the anchor 330 is attached to the collet 328. In this regard it should be appreciated that the anchor 330 is freely rotatable within the collet 328 and extension 387 with respect to the anchor seat 326.

The bottom surface of the posts 381 abut the neck 333, and therefore provide a laterally extending guide 392 that allows the anchor 330 to pivot in the sagittal plane, while preventing the anchor 330 from pivoting in any other angle that intersects the sagittal plane. The extension 377 does not extend entirely around the anchor neck 335, and thus defines a gap that is disposed on one longitudinal side of the anchor 330. Thus, the anchor 330 is free to pivot toward that longitudinal side in the sagittal plane until the anchor 330 abuts the lower end of the respective spacer wall 338, which provides a stop for the anchor 330 in the sagittal plane. The collar 379 extends along the opposing longitudinal side of the anchor 330, and can be vertically flush with or above the bottom surface of the corresponding spacer wall 338 such that the spacer wall provides a stop with respect to angular movement of the anchor 330 in the sagittal plane. Alternatively, the collar 379 could be disposed below the bottom surface of the corresponding spacer wall 338 such that the collar 379 provides a stop with respect to angular movement of the anchor 330 in the sagittal plane. Thus, the collar 379 can limit pivotal movement in one direction in the pivotal plane. Alternatively still, the radially inner surface of the collar 379 could be radially outwardly displaced with respect to the radial inner surface of the posts 381, such that the collar 379 does not abut the neck 335 and thus permits pivotal movement in the sagittal plane toward the collar 379.

The collar 379 can be disposed at the inferior end of the anchor seat 326 when the bone fixation element is implanted, such that the anchor 330 can pivot along a greater angular range toward the superior end in the sagittal plane than toward the inferior end. Alternatively, the collar 379 can be disposed at the superior end of the anchor seat 326 when the bone fixation element is implanted, such that the anchor 330 can pivot along a greater angular range toward the superior end in the sagittal plane than toward the inferior end.

Once the anchor seat 326 has been aligned with the fixation rod 24, and the position of the bone anchor 330 has been located in the sagittal plane as desired, the locking cap 34 can be locked in the subassembly 375 in the manner described above.

Referring now to FIGS. 17-20, a bone fixation subassembly 475 constructed in accordance with an alternative embodiment is illustrated including reference numerals corresponding to like elements of the bone fixation subassembly 75 incremented by 400. Thus, the bone fixation subassembly 475 can be constructed as described with respect to one or all of the bone fixation subassemblies, except as otherwise noted. It should be appreciated that one or more up to all of the bone fixation elements of the bone fixation assembly 20 can include the bone fixation elements 22 or alternative bone fixation elements as described herein, one or more of which can include the bone fixation subassembly 475 as will now be described.

The bone fixation subassembly 475 includes an anchor seat 426, and a collet 428 preinstalled in the anchor seat 426. The subassembly 475 can further include a bone anchor 430 that can be preinstalled in the collet 428 as part of the subassembly 475 provide in the kit, or the bone anchor 430 can be provided separately, and later installed in the subassembly 475, for instance before or after being implanted in an underlying bone. The anchor can comprise a pin or nail, or a screw as desired.

The anchor seat 426 includes an anchor seat body 438 extending centrally along the central axis A. The body 438 includes a base 440 and a pair of spaced opposing arms 442 extending up from the base 440. The base 440 defines a lower end 450 that is also the lower end of the body 438, and defines a lower opening 452. The body 438 defines an axial bore 454 extending from the lower opening 452 to the upper opening 448. The arms 442 extend up from respective support walls 456, and the opposing spacer walls 458 are connected between the support walls 456. The arms 442 define gaps G therebetween that are configured to receive the fixation rod 24 as described above. The arms 442 further define internal threads 462 that are configured to engage the external threads 68 of the locking cap 34 as described above.

The collet 428 includes a collet body 445 that defines a first or upper end 447 sized and configured to contact or support at least a portion of the fixation rod 24 when the rod is received within the rod-receiving channel 436, and a second or lower end 449 sized and configured to contact or otherwise engage, directly or indirectly, a portion of the bone anchor head 33. The upper and lower ends 447 and 449 are generally constructed as described above, with respect to the collet 28, except the collet body includes fingers 469 of the same vertical length. Of course, it should be appreciated that one or more of the fingers 469 can extend down a greater or lesser difference than one or more of the other fingers.

The collet 428 further includes a pair of radially opposing protrusions 493 projecting radially inward from the upper ends of the collet flanges 457. When collet 428 is installed in the anchor seat 426, the flanges 457 are located in the recesses 461 such that the protrusion 493 is disposed radially centrally with respect to the arms 442 when the collet 428 is installed in the anchor seat. Each protrusion 493 defines a lower vertex 495 and upwardly angled walls 497 extending longitudinally out from the vertex 495. When anchor head 333 is in the collet fingers 469, the vertex 495 abuts the upper end of the anchor head 433, which can be flat in a radial direction perpendicular to the axis of rotation B.

Figure 20:
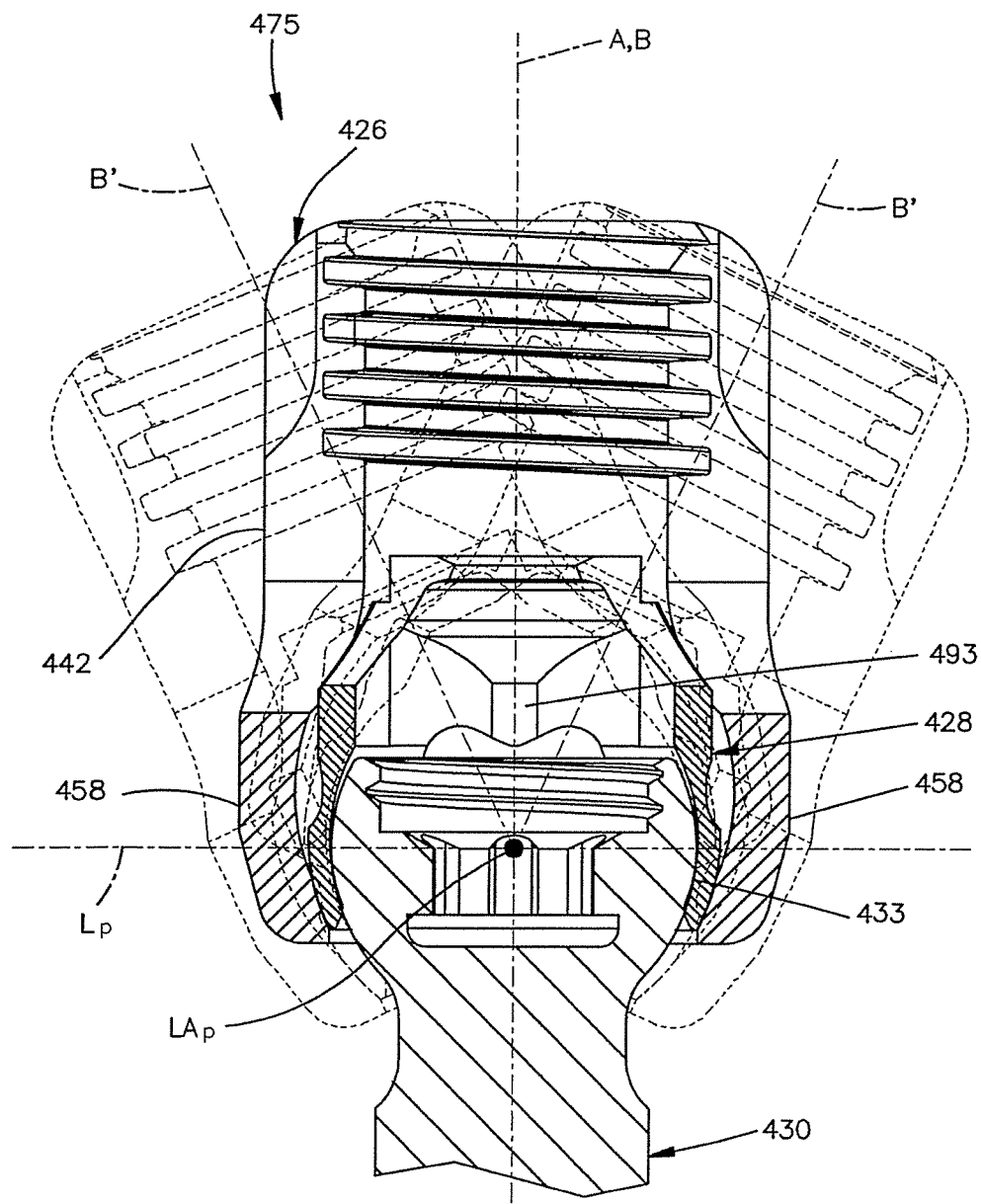
FIG. 20 is a sectional side elevation view similar the bone fixation subassembly of FIG. 19B, showing pivotal movement of the anchor seat relative to the bone anchor in the sagittal plane.

As illustrated in FIG. 20, the protrusion 493 permits the anchor 430 to pivot in a desired plane (e.g., the sagittal plane) relative to the collet 428 and anchor seat 426, while interference between the vertex 495 and the anchor head 433 prevents the anchor 430 from pivoting in any plane that intersects the sagittal plane. In particular, the anchor 430 can pivot in the desired plane through an angular range defined by the axis A and pivoted axes of rotation B' of the bone anchor 430. Thus, the protrusions 493 provide a guide that permits the anchor 430 to pivot in the desired plane while preventing pivotal movement of the bone anchor in all other planes that intersect the sagittal plane. The anchor 430 can freely rotate about its axis B with respect to the collet 428 and the anchor 426 in the manner described above.

The bone fixation subassembly 475 is constructed by inserting the collet 428 down through the top of the anchor seat 426 until the flanges 457 are locked in the corresponding recesses 461. The fingers 469A are placed over the head 33 of the bone anchor 30, and a downward force is applied against the anchor 430 until the fingers 169 expand radially outward to capture the head 433 of the bone anchor 430 therein. The threaded shaft 431 of the bone anchor 430 may already be implanted into bone prior to popping the collet 428 over the anchor head 433.

Once the anchor seat 426 has been aligned with the fixation rod 24, and the position of the bone anchor 430 has been located in the sagittal plane as desired, the locking cap 34 can be locked in the subassembly 475 in the manner described above.

Figure 21A:
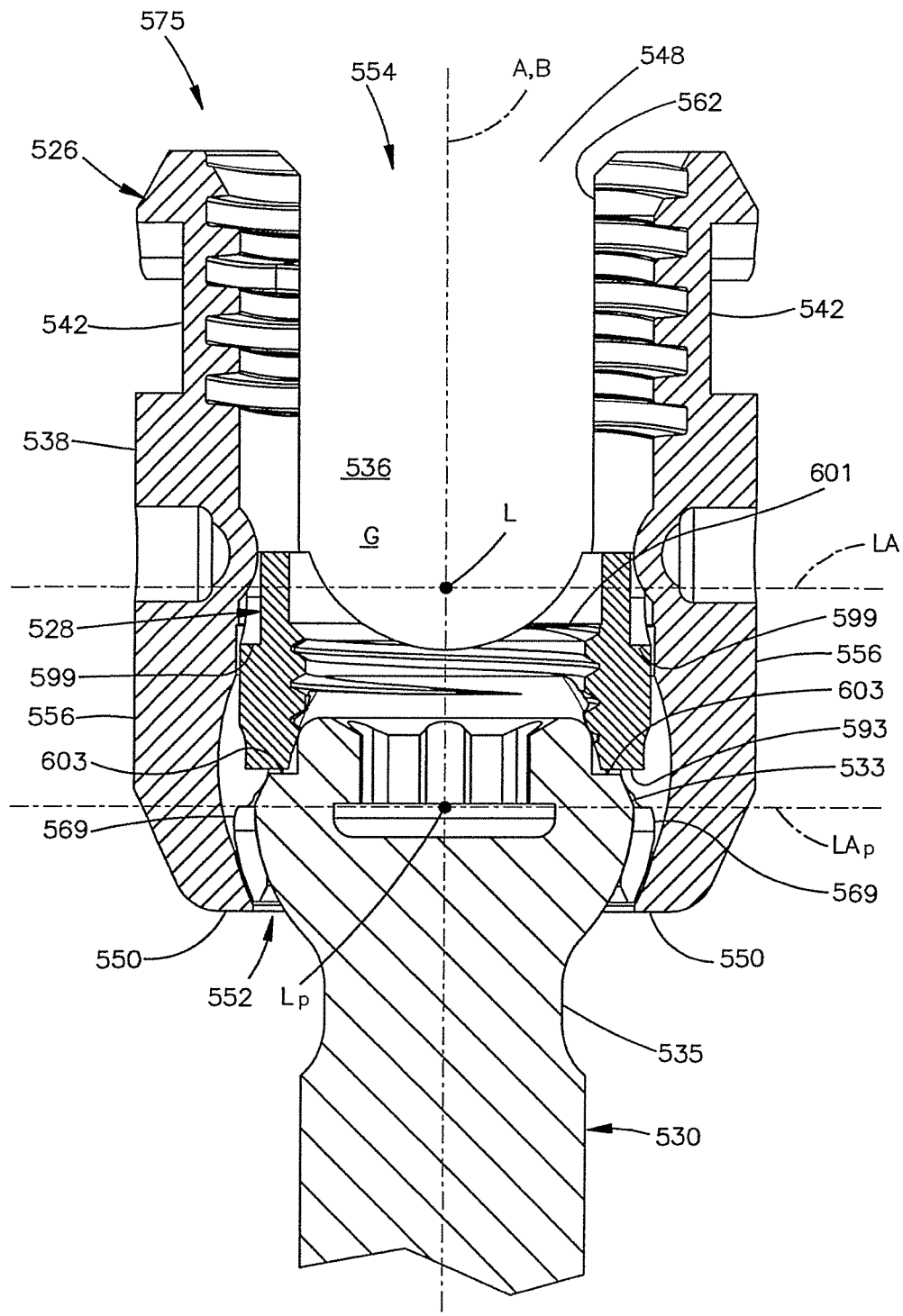
FIG. 21A is a sectional side elevation view similar to FIG. 19A, but of a bone fixation subassembly constructed in accordance with another alternative embodiment.
Figure 21B:
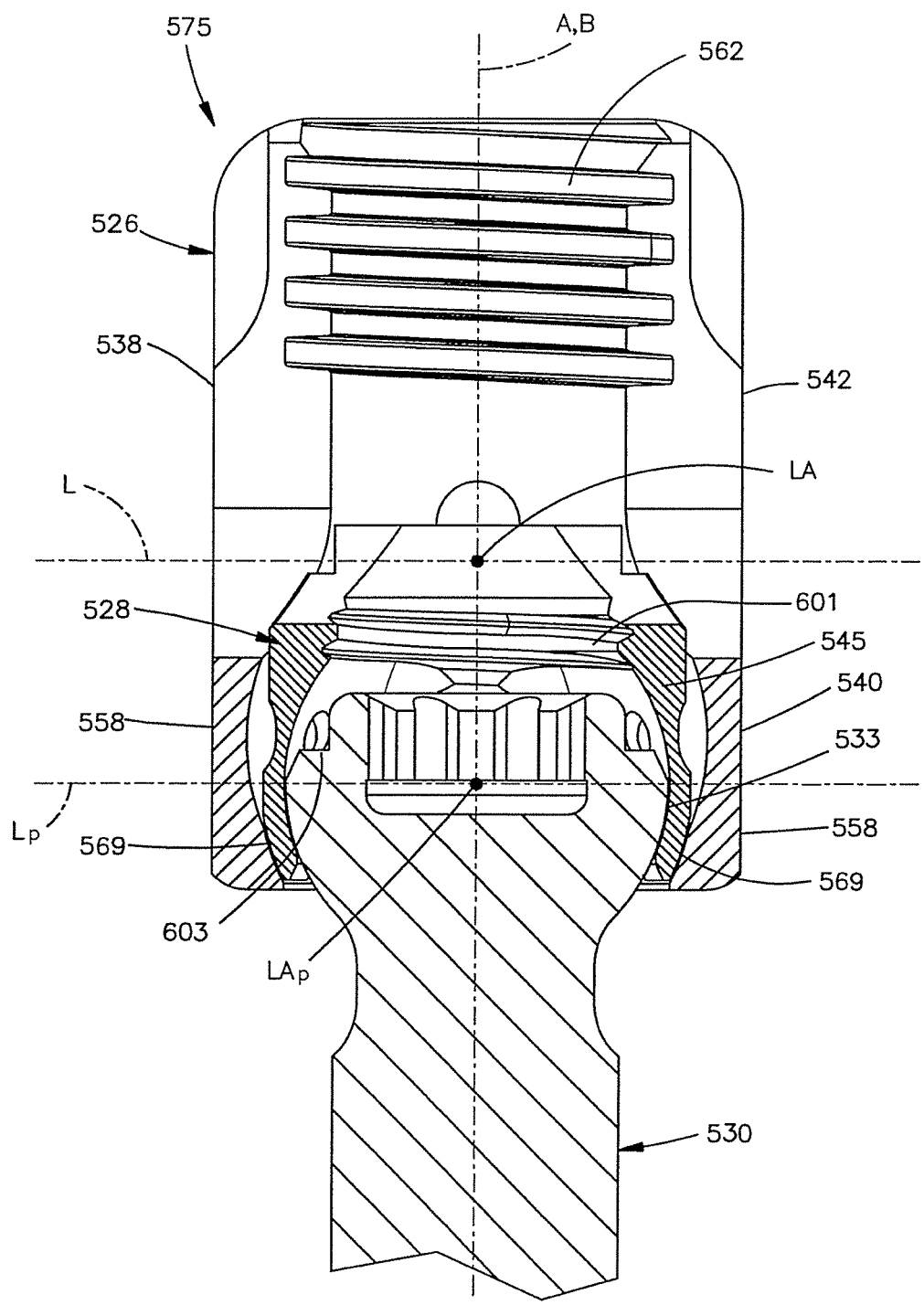
FIG. 21B is a sectional side elevation view similar to FIG. 19B, but of the bone fixation subassembly illustrated in FIG. 21A.
Figure 22:
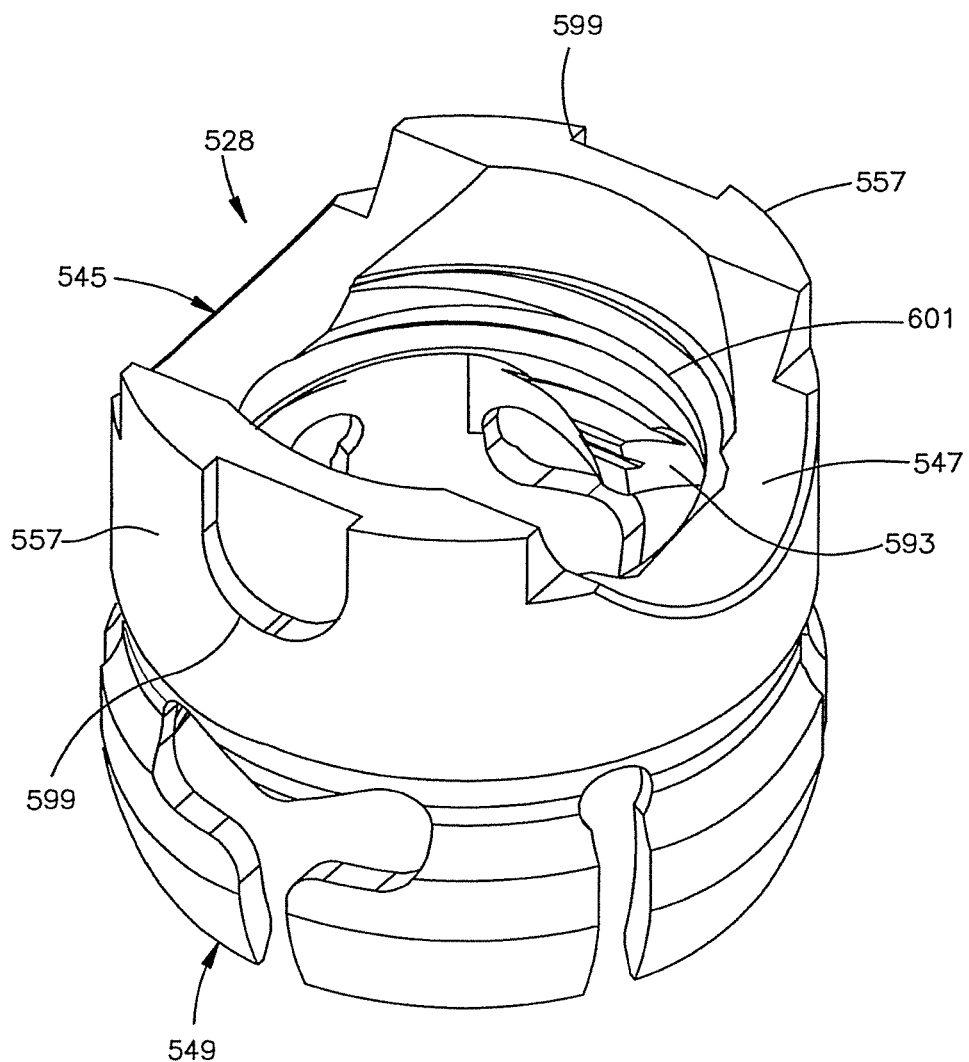
FIG. 22 is a perspective view of a collet of the bone fixation subassembly illustrated in FIG. 21A.

Referring now to FIGS. 21-22, a bone fixation subassembly 575 constructed in accordance with an alternative embodiment is illustrated including reference numerals corresponding to like elements of the bone fixation subassembly 75 incremented by 500. Thus, the bone fixation subassembly 575 can be constructed as described above with respect to one or all of the bone fixation subassemblies, except as otherwise noted. It should be appreciated that one or more up to all of the bone fixation elements of the bone fixation assembly 20 can include the bone fixation elements 22 or alternative bone fixation elements as described herein, one or more of which can include the bone fixation subassembly 575 as will now be described.

The bone fixation subassembly 575 includes an anchor seat 526, and a collet 528 preinstalled in the anchor seat 526. The subassembly 575 can further include a bone anchor 530 that can be preinstalled in the collet 528 as part of the subassembly 575 provide in the kit, or the bone anchor 530 can be provided separately, and later installed in the subassembly 575, for instance before or after being implanted in an underlying bone. The anchor 530 is illustrated as a pin or nail, though the anchor 530 could alternatively be constructed as a screw.

The anchor seat 526 includes an anchor seat body 538 extending centrally along the central axis A. The body 538 includes a base 540 and a pair of spaced opposing arms 542 extending up from the base 540. The base 540 defines a lower end 550 that is also the lower end of the body 538, and defines a lower opening 552. The body 538 defines an axial bore 554 extending from the lower opening 552 to the upper opening 548. The arms 542 extend up from respective support walls 556, and the opposing spacer walls 558 are connected between the support walls 556. The arms 542 define gaps G therebetween that are configured to receive the fixation rod 24 as described above. The arms 542 further define internal threads 562 that are configured to engage the external threads 68 of the locking cap 34 as described above.

The collet 528 includes a collet body 545 that defines a first or upper end 547 sized and configured to contact or support at least a portion of the fixation rod 24 when the rod is received within the rod-receiving channel 536, and a second or lower end 549 sized and configured to contact or otherwise engage, directly or indirectly, a portion of the bone anchor head 33. The upper and lower ends 547 and 549 are generally constructed as described above, with respect to the collet 428, except the collet body defines a U-shaped recess 599 extending radially inward into the radially outer surface of each flange 557. The recess 599 is configured to engage mating structure of the anchor seat 226 that prevents the collet 528 from inadvertently backing out of the anchor seat 226 during use.

The collet 528 further includes an interior threaded surface 601 disposed axially above the protrusion 593, which can receive corresponding threads of an insertion tool when assembling the subassembly 575. The protrusion, however, extends radially inward with respect to the protrusion 493, such that it engages the upper surface of a flat ledge 603 extending circumferentially about the anchor head 533. It should thus be appreciated that the flat ledge 603 defines a pair of opposing abutment surfaces that extend along a lateral axis that extends perpendicular to the longitudinal axis L defined by the opposing gaps G. The anchor 530 can therefore pivot in a desired (e.g., sagittal) plane about the protrusion 593 as described above. Additionally, as described above, the bone anchor 530 is free to rotate within the collet 528 relative to the anchor seat 526 as described above.

The bone fixation subassembly 575 is constructed by inserting the collet 528 down through the top of the anchor seat 526 until the flanges 557 are locked in the corresponding recesses 561. The fingers 569 are placed over the head 33 of the bone anchor 30, and a downward force is applied against the anchor 530 until the fingers 169 expand radially outward to capture the head 533 of the bone anchor 530 therein. The threaded shaft 531 of the bone anchor 530 may already be implanted into bone prior to popping the collet 528 over the anchor head 533. Alternatively, the bone anchor 530 can be installed in the collet 528, and subsequently implanted into underlying bone. The internal threading 601 of the collet 528 allows for the use of a special driver instrument having an engagement feature, e.g., a T25 feature, which can mate with the screwdriver to further stabilize the bone anchor 530 as it is implanted into the underlying bone.

Once the anchor seat 526 has been aligned with the fixation rod 24, and the position of the bone anchor 530 has been located in the sagittal plane as desired, the locking cap 34 can be locked in the subassembly 575 in the manner described above.

Figure 23:
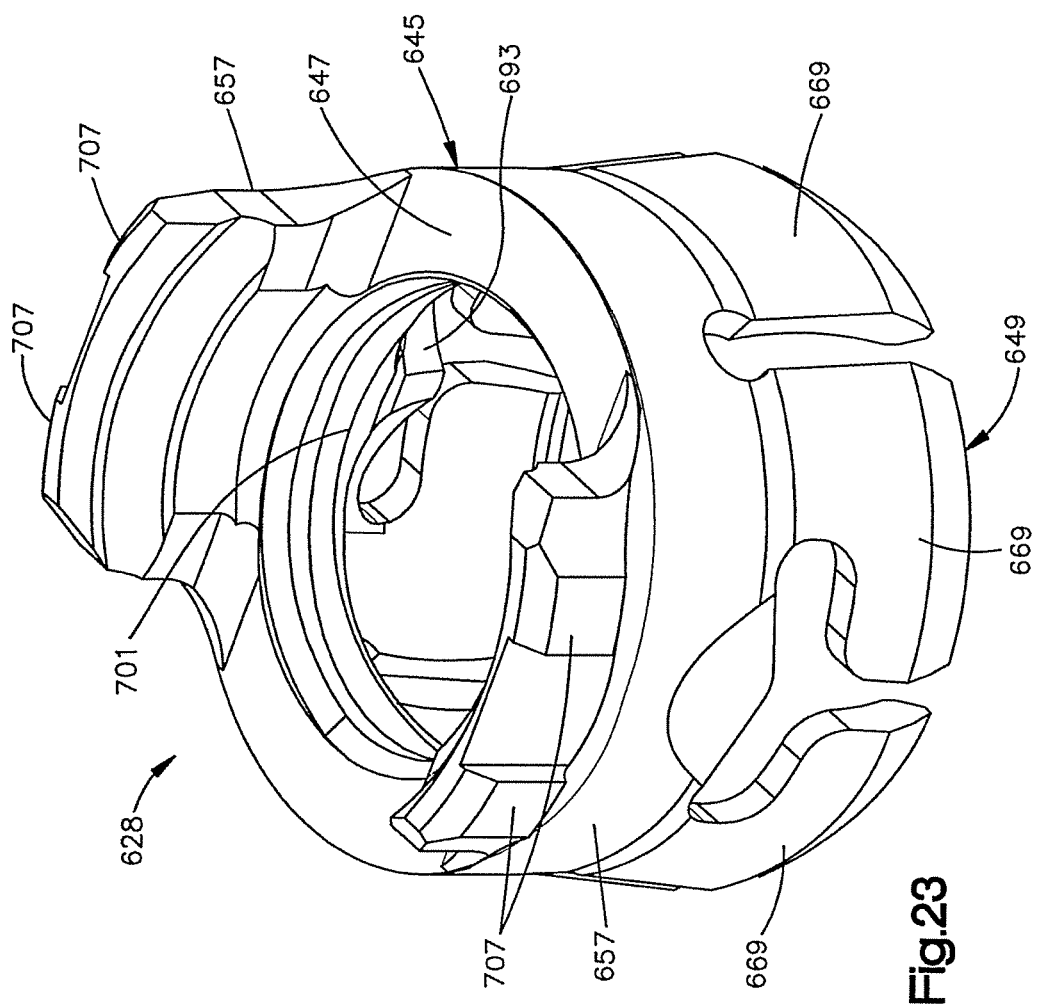
FIG. 23 is a perspective view of a collet of a bone fixation subassembly constructed in accordance with another embodiment.
Figure 24A:
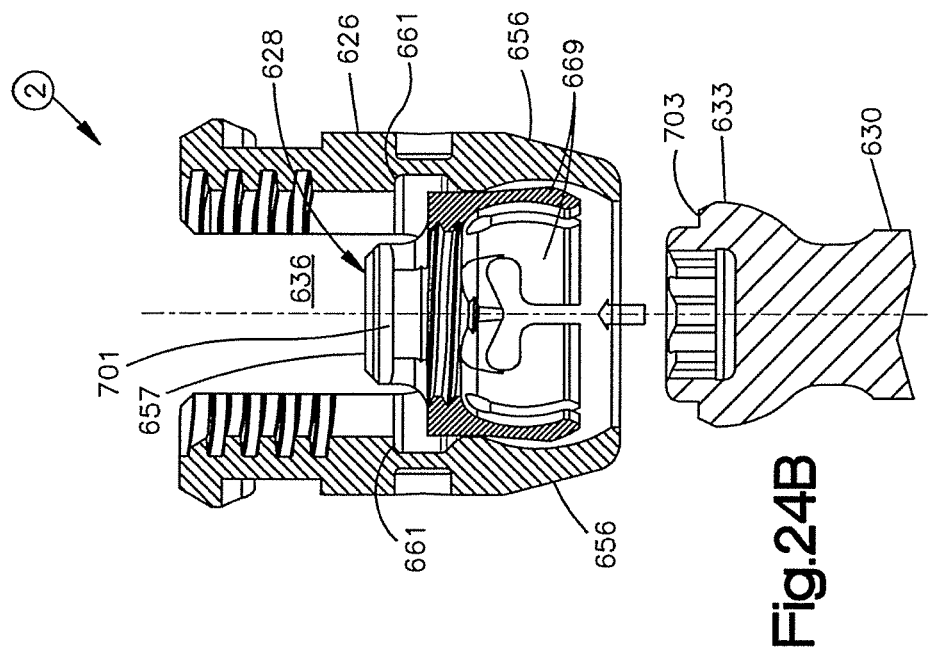
FIG. 24A is a schematic view illustrating a method for assembling the bone fixation subassembly illustrated in FIG. 23.
Figure 24B:
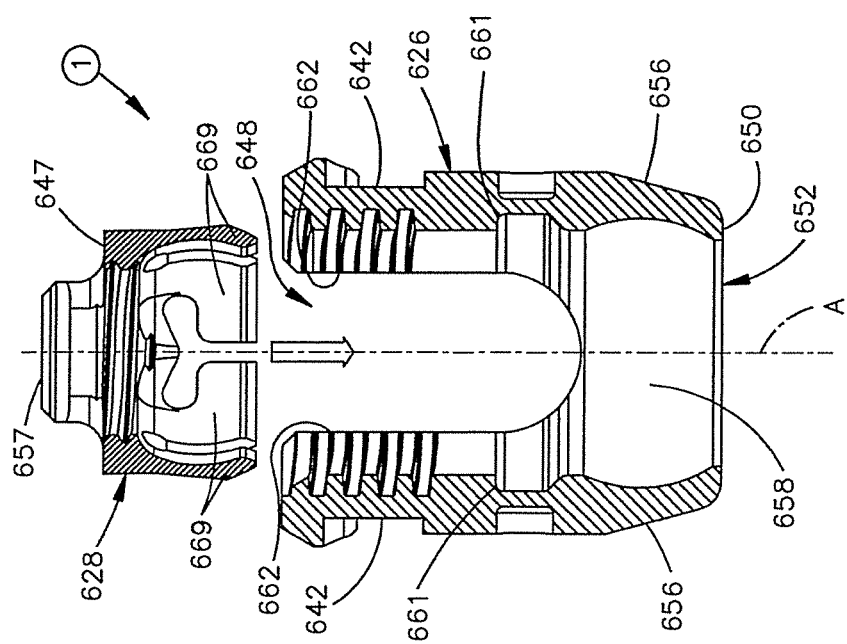
FIG. 24B is a schematic view illustrating the method for assembling the bone fixation subassembly illustrated in FIG. 23, and showing the bone anchor being inserted into the lower end of the anchor seat thereby popping the collet over the anchor head so as to attach the anchor to the collet.
Figure 24E:
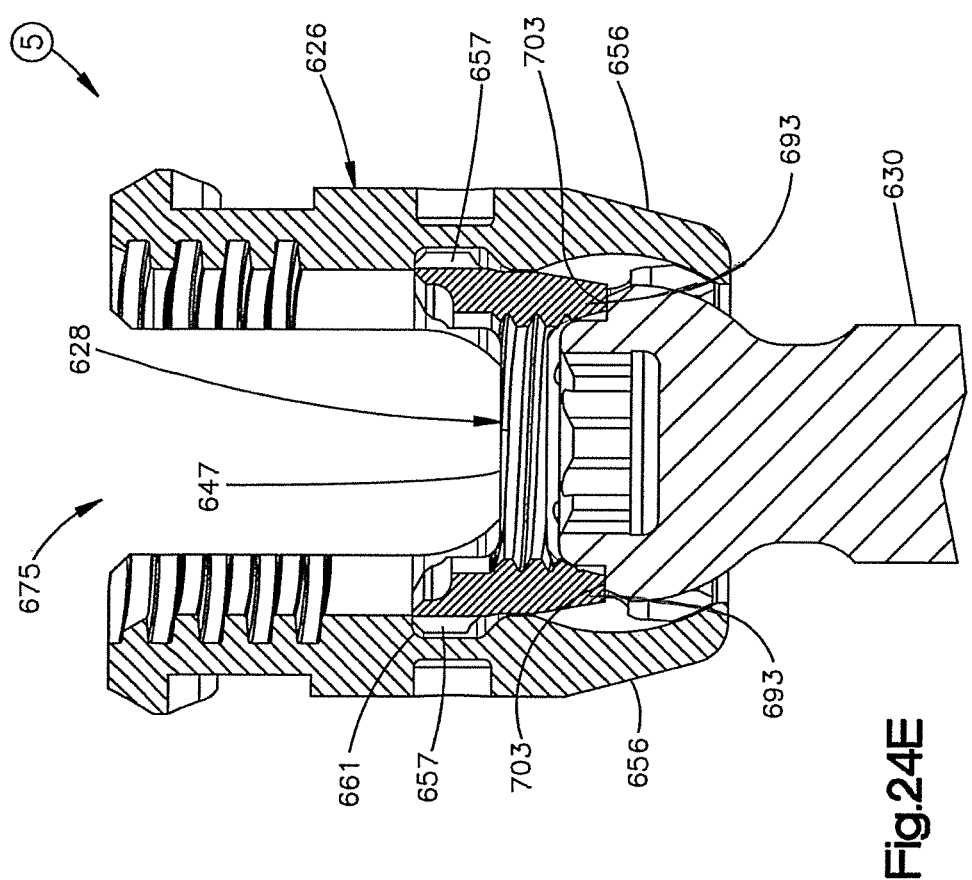
FIG. 24E is a schematic view illustrating a method for assembling the bone fixation subassembly illustrated in FIG. 23, and showing the collet positioned radially such that the dimples are disposed in the gaps so that the collet is unable to freely rotate or pivot relative to the anchor seat.
Figure 25:
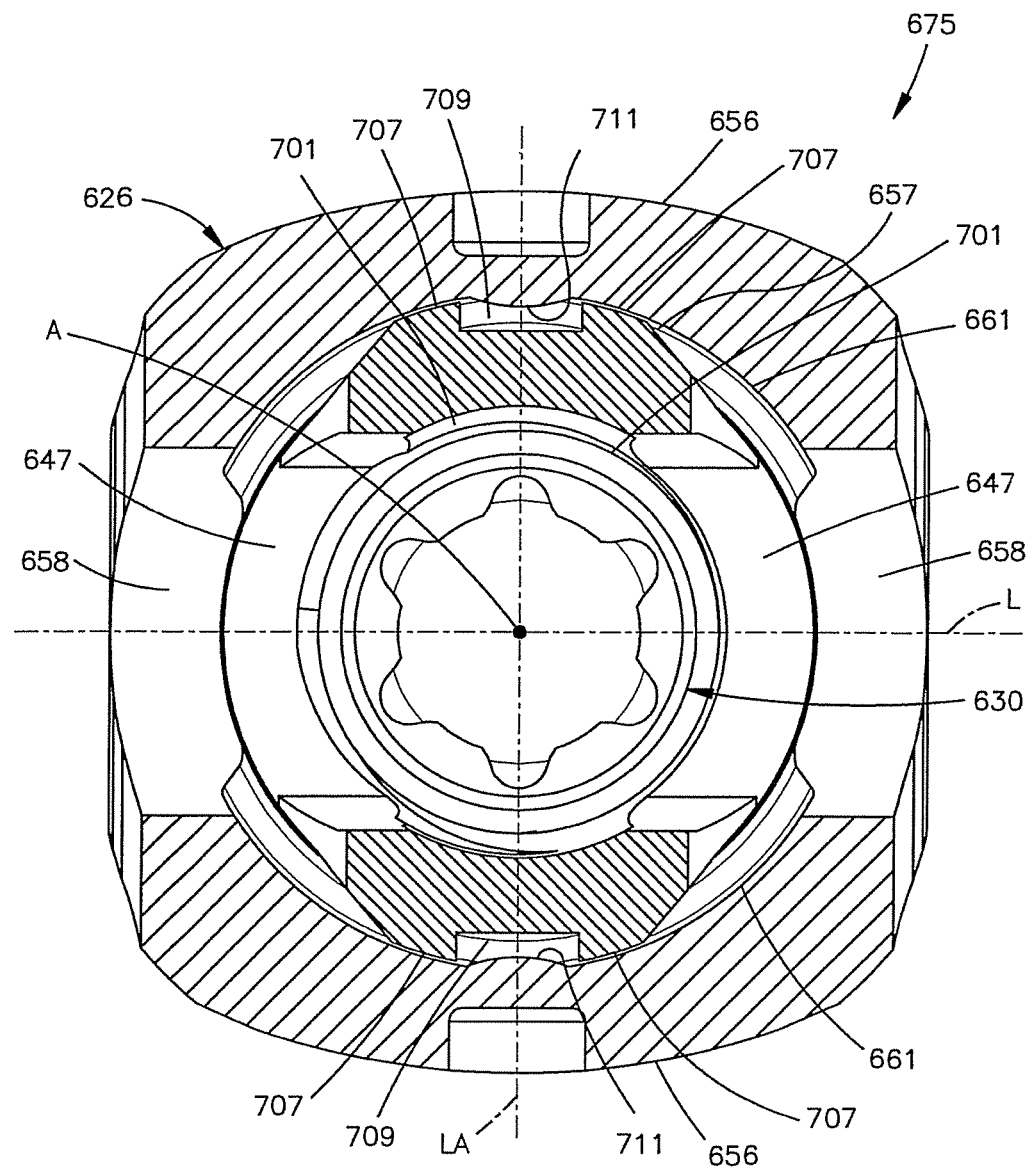
FIG. 25 is a sectional top plan view of the bone fixation subassembly illustrated at step 5 of FIG. 24E.

Referring now to FIGS. 23-25, a bone fixation subassembly 675 constructed in accordance with an alternative embodiment is illustrated including reference numerals corresponding to like elements of the bone fixation subassembly 75 incremented by 600. Thus, the bone fixation subassembly 675 can be constructed as described above with respect to one or all of the bone fixation subassemblies, except as otherwise noted. It should be appreciated that one or more up to all of the bone fixation elements of the bone fixation assembly 20 can include the bone fixation elements 22 or alternative bone fixation elements as described herein, one or more of which can include the bone fixation subassembly 675 as will now be described.

The bone fixation subassembly 675 includes an anchor seat 626, and a collet 628 preinstalled in the anchor seat 626. The subassembly 675 can further include a bone anchor 630 that can be preinstalled in the collet 628 as part of the subassembly 675 provide in the kit, or the bone anchor 630 can be provided separately, and later installed in the subassembly 675, for instance before or after being implanted in an underlying bone. The anchor 630 is illustrated as a pin or nail, though the anchor 530 could alternatively be constructed as a screw.

The anchor seat 626 extends centrally along the central axis A, and includes a pair of spaced opposing arms 642 extending up from respective support walls 656. The opposing spacer walls 658 are connected between the support walls 656. The anchor seat 626 defines a lower end 650 that defines a lower opening 652. An axial bore 654 extends from the lower opening 652 to the upper opening 648. The arms 642 define gaps G therebetween that are configured to receive the fixation rod 24 as described above. The arms 642 further define internal threads 662 that are configured to engage the external threads 68 of the locking cap 34 in the manner described above.

The collet 628 includes a collet body 645 that defines a first or upper end 647 sized and configured to contact or support at least a portion of the fixation rod 24 when the rod is received within the rod-receiving channel 636, and a second or lower end 649 sized and configured to contact or otherwise engage, directly or indirectly, a portion of the bone anchor head 33. The upper and lower ends 647 and 649 are generally constructed as described above, with respect to the collet 528, except each flange 657 includes a pair of opposing vertical ribs 707 spaced apart a distance by a gap 709. The outer circumferential edges of the ribs 707 are spaced apart substantially the same distance as the circumferential edges of the recess 661 formed in the inner surface of the support walls 656. As a result, when the collet 628 is inserted into the anchor seat 626, the ribs 707 become disposed in the recess 661. The collet 628 further includes an inner threaded surface 701, and protrusions 693 disposed below the threaded surface 701. The protrusions 693 define a guide that allows the bone anchor 30 to pivot relative to the anchor seat in the sagittal plane, in the manner described above.

The bone anchor 630 includes a pair of opposing flat ledges 703 extending circumferentially around the anchor head 633 in the manner described above. The remainder of the anchor head 633 can be round in the manner described above. Thus, the ledges 703 are configured to abut the lower end of the protrusions 693 when the collet 628, anchor 630, and fixation rod 24 are installed in the anchor seat 626, as will now be described with respect to FIGS. 24-25.

As illustrated in FIGS. 24A-24E, the bone fixation subassembly 675 is constructed by inserting the collet 628 down through the top of the anchor seat 626 to an initial insertion position at step 1, until the flanges 657 are disposed in the corresponding recesses 661 in the manner described above. When the collet 628 is in the initial insertion position, the upper end 647 of the collet can be aligned with the gaps G. Next, at step 2, the bone anchor 630 is inserted into the lower end 652 of the anchor seat 626, thereby popping the fingers 669 over the anchor head 633 so as to attach the anchor 630 to the collet 628. Interference between the fingers 669 and the upper end of the support walls 656 prevents the collet 628 from backing out of the anchor seat 626 in response to the upwardly directed force applied by the anchor 630. The bone anchor 630 can be inserted into the anchor seat 626 and collet 628 when assembling the subassembly 675, or after the subassembly 675 has been assembled, for instance interoperatively (e.g., after the bone anchor 630 has been affixed in a vertebrae). In the position illustrated in FIG. 2, the upper ends 647 of the collet 628 are angularly offset with respect to the rod-receiving channel 636. As illustrated, the upper ends 647 are oriented perpendicular with respect to the channel 636.

Once the anchor head 633 is captured in the fingers 669, a downward force is applied on the anchor 630 relative to the anchor seat 626 at step 3, which brings the collet 628 to an intermediate insertion position, whereby the fingers 669 bear against the support walls 656 and spacer walls 658. In the intermediate insertion position the lower ends of the fingers 669 are aligned with the lower ends of the support walls 656 and spacer walls 658. As the collet 628 moves to the intermediate insertion position, the flanges 657 flare radially inward out of engagement with the recesses 661, and bear against the radially inner surfaces of the support walls 656.

It should be appreciated that in the intermediate insertion position, the flanges 657 of the collet 628 are disposed in the rod-receiving channel 636, and thus positioned to interfere with the fixation rod 24 when the fixation rod is inserted. Because the flanges 657 are not disposed in the recess 661, the collet 628, and thus the bone anchor 633, is unimpeded with respect to pivotal movement about any radial axis about a 360° range with respect to the anchor seat 626, and therefore along any corresponding plane as desired, including the sagittal plane and any other plane angularly offset with respect to the sagittal plane. The anchor 630 is further able to freely rotate about its central axis B relative to the collet 628 and the anchor seat 626.

At step 4, the collet 628 is rotated in the direction of Arrow A about axis A, until the flanges 657 are brought into alignment with the corresponding recesses 661. As shown in FIG. 25, the anchor seat 626 includes a retention dimple 711 extending radially inward from each support wall 656 at a location circumferentially centrally disposed in the corresponding recess 661. As the collet 628 is rotated in the direction of Arrow A, one of each pair of ribs 707 cams over the dimple 711. Until each dimple 711 is disposed in the corresponding gap 709. Interference between the dimple 711 and the ribs 707 therefore resists rotation of the collet 628 relative to the anchor seat 626. As shown in step 5 of FIG. 24E, once the collet 628 is positioned radially such that the dimples 711 are disposed in the gaps 709, the collet 628 is unable to freely rotate or pivot relative to the anchor seat 626. Because the protrusions 693 are aligned with, and abut, the ledges 703 of the anchor 630, the protrusions 693 provide a guide that prevents pivotal movement of the anchor 630 relative to the anchor seat 626 in all planes other than the sagittal plane as described above. Furthermore, when the dimples 711 are disposed in the gaps 709, the upper ends 647 of the collet 626 are aligned with the rod-receiving channel 636, thereby providing a seat for the fixation rod 24 in the manner described above.

In certain embodiments, when the dimples 711 are disposed in the gaps 709, interference between the dimples 711 and the flanges 707 prevent inadvertent rotation of the collet 628 relative to the anchor seat 626 that would bring the flange out of the recess 661. However, deliberate rotation of the collet 628 about axis A relative to the anchor seat, for instance with a tool that engages the internal threads 701, can cause the flange 657 to flex radially inward as the ribs 707 cam over the dimples 711. Once the flange 657 flexes inward, the dimple 711 is no longer disposed in the gap 709. As the collet 628 is further rotated, the flange 657 rotates to a position circumferentially between recesses 661, whereby the collet 628 and bone anchor 630 can freely pivot and rotate relative to the anchor seat 626 as described above.

In this manner, in instances where the bone anchor 630 is inserted into the underlying vertebra, and the subassembly 675 including the anchor seat 626 and collet 628 are attached to the bone anchor 630 interoperatively, a surgical instrument could rotate the collet 628 between its locked position whereby the dimples 711 are disposed in the gaps 709 and its unlocked position whereby the flanges 657 are disposed outside of the recesses 661.

When the collet 628 is in the unlocked position, the bone anchor 630 is permitted to pivot both in the sagittal plane and in any other plane angularly offset with respect to the sagittal plane about a 360° range. When the collet 628 is in the locked position, the bone anchor 630 is permitted to pivot only in the sagittal plane relative to the anchor seat 626. Once the anchor seat 626 has been aligned with the fixation rod 24, and the position of the bone anchor 630 has been located as desired, the locking cap 34 can be locked in the subassembly 675 in the manner described above.

It should be appreciated that the illustrations and discussions of the embodiments shown in the figures are for exemplary purposes only, and should not be construed limiting the disclosure. One skilled in the art will appreciate that the present disclosure contemplates various embodiments. It should be further appreciated that the features and structures described and illustrated in accordance one embodiment can apply to all embodiments as described herein, unless otherwise precluded. For instance, while the collet provides a guide in certain embodiments and the anchor seat comprises a guide in other embodiments, it should be appreciated that the above-described features of the collet could be combined with those of the anchor seat such that at least one, or both, of the collet and anchor seat provide a guide that prevents angular movement of the bone anchor is all planes other than the desired plane. It should be understood that the concepts described above with the above-described embodiments may be employed alone or in combination with any of the other embodiments described above.

What is claimed is:

1. An anchor seat for a bone anchor, the anchor seat comprising:
   a pair of arms that define an upper end of the anchor seat and that are spaced from one another along a first direction so as to define a rod receiving channel that extends between the arms of the pair along a second direction, perpendicular to the first direction; and
   a base that defines a lower end of the anchor seat and that is monolithic with the pair of arms such that the pair of arms extend from the base along a third direction, perpendicular to both the first and second directions, the anchor seat defining a bore that extends from the upper end and entirely through the lower end along a central axis that extends in the third direction, the base including a pair of opposed guide walls spaced apart from one another along the first direction so as to define a lower opening between the pair of guide walls, and the base being configured to receive a head of the bone anchor therein such that the bone anchor extends through the lower opening,
   wherein the pair of guide walls are configured to directly engage opposing abutment surfaces of the bone anchor so as to permit the bone anchor to pivot along a select plane that extends in the second and third directions, and prevents the bone anchor from pivoting in any plane other than the select plane.

2. The anchor seat of claim 1, wherein the guide walls define respective inner guide surfaces that face one another along the second direction so as to define the lower opening.

3. The anchor seat of claim 2, wherein inner guide surfaces extend along respective planes that extend along the second and third directions.

4. The anchor seat of claim 2, wherein the lower end defines at least one lower end surface that extends in a direction substantially perpendicular to the inner guide surfaces, the at least one lower end surface providing a stop that limits pivoting of the bone anchor along the select plane.

5. The bone fixation subassembly of claim 4, wherein the at least one lower end surface includes a pair of spaced lower end surfaces that extend in a direction substantially perpendicular to the guide surfaces, the lower end surfaces providing stops that limit pivoting of the bone anchor along the select plane on either side of the central axis.

6. The anchor seat of claim 1, wherein the pair of guide walls are configured so as to permit the bone anchor to pivot in the select plane on opposite sides of the central axis.

7. The anchor seat of claim 1, wherein the pair of guide walls define a distance therebetween that is substantially equal to a distance between the opposing abutment surfaces of the bone anchor.

8. A bone anchor assembly, comprising:
   an anchor seat for a bone anchor, the anchor seat comprising:
      a pair of arms that define an upper end of the anchor seat and that are spaced from one another along a first direction so as to define a rod receiving channel that extends between the arms of the pair along a second direction, perpendicular to the first direction; and
      a base that defines a lower end of the anchor seat and that is monolithic with the pair of arms such that the pair of arms extend from the base along a third direction, perpendicular to both the first and second directions, the anchor seat defining a bore that extends through the anchor seat from the upper end to the lower end along a central axis that extends in the third direction, the base including a pair of opposed guide walls spaced apart from one another along the first direction so as to define a lower opening between the pair of guide walls, the lower opening being configured to receive the bone anchor,
      wherein the pair of guide walls include a pair of opposing inner surfaces that are configured to engage opposing abutment surfaces of the bone anchor so as to permit the bone anchor to pivot along a select plane that extends in the second and third directions, and so as to prevent the bone anchor from pivoting in any plane other than the select plane; and
   a collet including a collet body configured to be disposed in the anchor seat, the collet body defining an upper end and an expandable lower end, the expandable lower end configured to receive a head of the bone anchor,
   wherein the bone anchor assembly is configured such that the inner surfaces of the opposing guide walls do not contact the collet when the bone anchor is received in the collet and the collet is seated in the anchor seat.

9. The bone anchor assembly of claim 8, wherein the anchor seat and collet are configured such that, when the collet is disposed in the anchor seat, the collet is rotationally and pivotally fixed relative to the anchor seat.

10. The bone anchor assembly of claim 8, wherein the collet defines a pair of seat portions at the upper end of the collet, the seat portions being spaced apart from one another along the second direction and being configured to receive a fixation rod.

11. The bone fixation subassembly of claim 8, wherein the collet body defines an upper end, and an expandable lower end spaced from the upper end, and wherein a plurality of slots extend through the expandable lower end such that the expandable lower end defines a first plurality of fingers separated by slots and a second plurality of fingers opposite the first plurality of fingers.

12. A bone fixation subassembly configured to receive a fixation rod and a locking cap, the bone fixation subassembly comprising:
   an anchor seat including an anchor seat body that defines an upper end and a lower end that are spaced from one another along a central axis of the anchor seat body, the upper end defining a pair of opposing fixation rod-receiving gaps that are spaced from one another along a longitudinal axis, and the anchor seat defining a bore that extends from the upper end and entirely through the lower end along the central axis, the bore being disposed between the rod-receiving gaps; and
   a collet including a collet body configured to be disposed in the bore of the anchor seat, the collet body configured to attach to a head of a bone anchor that has a central axis, wherein a plurality of slots extend through an expandable lower end of the collet such that the expandable lower end defines a first plurality of fingers and a second plurality of fingers opposite the first plurality of fingers,
   wherein the anchor seat is configured to receive the head of the bone anchor and the collet therein such that the head of the bone anchor is attached to the collet and the bone anchor extends out the lower end of the anchor seat, and such that the bone anchor is permitted to pivot relative to the collet in a select plane such that the central axis of the bone anchor can extend on opposed sides of the central axis of the anchor seat within the select plane and is prevented from pivoting in any plane other than the select plane, and wherein the bone fixation subassembly comprises a guide configured to abut opposing abutment surfaces of the bone anchor that are separated along an axis that is perpendicular to the longitudinal axis, so as to direct pivotal movement of the bone anchor in the select plane.

13. The bone fixation subassembly of claim 12, wherein the bone anchor is permitted to pivot only along the select plane about an axis that extends along a direction that is perpendicular to the longitudinal axis.

14. The bone fixation subassembly of claim 12, comprising the bone anchor, wherein the bone anchor has an anchor head that includes a pair of opposing flat surfaces, and the guide is configured to abut the opposing flat surfaces so as to direct pivotal movement of the bone anchor in the select plane and prevent the bone anchor from pivoting in any plane other than the select plane.

15. A bone fixation subassembly configured to receive a fixation rod and a locking cap, the bone fixation subassembly comprising:

an anchor seat including an anchor seat body that defines an upper end and a lower end that are spaced from one another along a central axis of the anchor seat body, the upper end defining a pair of opposing fixation rod-receiving gaps that are spaced from one another along a longitudinal axis, and the anchor seat defining a bore that extends from the upper end and entirely through the lower end along the central axis, the bore being disposed between the rod-receiving gaps, wherein the lower end of the anchor seat body defines a pair of inner guide surfaces that define a guide that is configured to engage an abutment surface of the bone anchor so as to direct pivotal movement of the bone anchor in the select plane; and a collet including a collet body configured to be disposed in the bore of the anchor seat, the collet body configured to attach to a head of a bone anchor that has a central axis, wherein a plurality of slots extend through an expandable lower end of the collet such that the expandable lower end defines a first plurality of fingers and a second plurality of fingers opposite the first plurality of fingers, wherein the anchor seat is configured to receive the head of the bone anchor and the collet therein such that the head of the bone anchor is attached to the collet and the bone anchor extends out the lower end of the anchor seat, and such that the bone anchor is permitted to pivot relative to the collet in a select plane such that the central axis of the bone anchor can extend on opposed sides of the central axis of the anchor seat within the select plane and is prevented from pivoting in any plane other than the select plane.

16. The bone fixation subassembly of claim 15, wherein the inner guide surfaces face one another along a direction that is perpendicular to both the longitudinal axis and the central axis.

17. The bone fixation subassembly of claim 15, wherein the lower end defines at least one lower end surface that extends in a direction substantially perpendicular to the guide surfaces, the at least one lower end surface providing a stop that limits pivoting of the bone anchor along the select plane.

* * * * *